(12) United States Patent
Hoff et al.

(10) Patent No.: US 11,898,172 B2
(45) Date of Patent: Feb. 13, 2024

(54) 3-HYDROXYBUTYRYL-COA DEHYDROGENASE VARIANTS AND METHODS OF USE

(71) Applicant: Genomatica, Inc., San Diego, CA (US)

(72) Inventors: Kevin Hoff, San Diego, CA (US); Cara Ann Tracewell, Solana Beach, CA (US); Kui Chan, Los Angeles, CA (US); Michael Kuchinskas, Franklin, MA (US); Harish Nagarajan, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 12 days.

(21) Appl. No.: 16/498,336

(22) PCT Filed: Mar. 29, 2018

(86) PCT No.: PCT/US2018/025086
§ 371 (c)(1),
(2) Date: Sep. 26, 2019

(87) PCT Pub. No.: WO2018/183640
PCT Pub. Date: Oct. 4, 2018

(65) Prior Publication Data
US 2020/0087634 A1 Mar. 19, 2020

Related U.S. Application Data

(60) Provisional application No. 62/480,208, filed on Mar. 31, 2017.

(51) Int. Cl.
*C12N 9/04* (2006.01)
*C12N 9/10* (2006.01)
*C12P 7/18* (2006.01)
*C12P 7/24* (2006.01)
*C12P 7/52* (2006.01)
*C12P 19/32* (2006.01)

(52) U.S. Cl.
CPC ......... *C12N 9/0006* (2013.01); *C12N 9/1029* (2013.01); *C12P 7/18* (2013.01); *C12P 7/24* (2013.01); *C12P 7/52* (2013.01); *C12P 19/32* (2013.01); *C12Y 101/01157* (2013.01); *C12Y 203/01009* (2013.01)

(58) Field of Classification Search
CPC ....... C12N 9/0006; C12N 9/1029; C12P 7/18; C12P 7/24; C12P 7/52; C12P 19/32; C12P 7/42; C12P 11/00; C12Y 101/01157; C12Y 203/01009; C12Y 101/01036
See application file for complete search history.

(56) References Cited

U.S. PATENT DOCUMENTS

| | | | |
|---|---|---|---|
| 7,127,379 B2 | 10/2006 | Palsson et al. |
| 9,017,983 B2 | 4/2015 | Burgard et al. |
| 2002/0012939 A1 | 1/2002 | Palsson |
| 2002/0168654 A1 | 11/2002 | Maranas et al. |
| 2003/0059792 A1 | 3/2003 | Palsson et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2009/0047719 A1 | 2/2009 | Burgard et al. |
| 2013/0066035 A1 | 3/2013 | Burgard et al. |
| 2015/0164855 A1 | 6/2015 | Clarke et al. |

FOREIGN PATENT DOCUMENTS

| | | |
|---|---|---|
| WO | WO 2002/055995 | 7/2002 |
| WO | WO 2003/106998 | 12/2003 |
| WO | WO 2006/043555 | 4/2006 |
| WO | WO 2006-043555 A1 * | 4/2006 |
| WO | WO 2009/094485 | 7/2009 |
| WO | WO 2010/127319 | 11/2010 |
| WO | WO 2011/156794 | 12/2011 |
| WO | WO 2013/036764 | 3/2013 |
| WO | WO 2014/190251 | 11/2014 |
| WO | WO 2018/183628 | 10/2018 |
| WO | WO 2018/183664 | 10/2018 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Altschul et al., "Basic Local Alignment Search Tool," *J. Mol. Biol.* 215:403-410 (1990).
Bergquist et al., "Degenerate oligonucleotide gene shuffling (DOGS) and random drift mutagenesis (RNDN): two complementary techniques for enzyme evolution," *Biomol. Eng.*, 22:63-72 (2005).
Bergquist et al., "Degenerate oligonucleotide gene shuffling," *Methods Mol. Biol.*, 352:191-204 (2007).
Burgard et al., "Minimal reaction sets for *Escherichia coli* metabolism under different growth requirements and uptake environments," *Biotechnol. Prog.*, 17:791-797 (2001).

(Continued)

*Primary Examiner* — Iqbal H Chowdhury
(74) *Attorney, Agent, or Firm* — Greenberg Traurig LLP

(57) ABSTRACT

The present disclosure provides thiolases and polypeptide variants of 3-hydroxybutyryl-CoA dehydrogenase, nucleic acids encoding the same, vectors comprising the nucleic acids, and cells comprising the polypeptide variants and/or thiolase, the nucleic acids, and/or the vectors. The present disclosure also provides methods of making and using the same, including methods for culturing cells, and for the production of various products, including 3-hydroxybutyryl-CoA (3-HB-CoA), 3-hydroxybutyraldehyde (3-HBal), 3-hydroxybutyrate (3-HB), 1,3-butanediol (1,3-BDO), and esters and amides thereof, and products made from any of these.

54 Claims, 26 Drawing Sheets

Specification includes a Sequence Listing.

(56) References Cited

OTHER PUBLICATIONS

Burgard et al., "OptKnock: A Bilevel Programming Framework for Identifying Gene Knockout Strategies for Microbial Strain Optimization," *Biotechnol. Bioeng.*, 84(6):647-657 (2003).
Coco et al., "DNA shuffling method for generating highly recombined genes and evolved enzymes," *Nat. Biotechnol.*, 19(4):354-359 (2001).
Colonna et al., "Synthesis and radiocarbon evidence of terephthalate polyesters completely prepared from renewable resources," *Green Chem.*, 13:3543-2548 (2011).
Cosmetic Ingredient Review Board, "Final Report on the Safety Assessment of Butylene Glycol, Hexylene Glycol, Ethoxy diglycol, and Dipropylene Glycol," *J. American College Toxicology*, 4(5)223-248 (1985).
Currie et al., "Authentication and dating of biomass components of industrial materials; links to sustainable technology," *Nucl. Instr. Methods Phys. Res. B*, 172:281-287 (2000).
Drake ed., *Acetogenesis*, Chapman and Hall, New York, NY, pp. 3-60 (1994).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucleic Acids Res.*, 32(19):e145 (2004).
GenBank Accession No. CCF95918, "Acetoacetyl-CoA reductase [Ralstonia solanacearum K60-1]," Feb. 20, 2012.
GenBank Accession No. SAL82526, "acetyacetyl-CoA reductase [Caballeronia choica]," Apr. 15, 2016.
GenBank Accession No. WP_009606749, "acetoacetyl-CoA reductase [Xanthomonas translucens]," Jun. 6, 2013.
GenBank Accession No. AGN95877, "chain dehydrogenase/reductase SDR [Achromobacter sp. JA81]," Jun. 19, 2013.
GenBank Accession No. AAB65780, "acetoacetyl-CoA reductase [Alcaligenes sp. SH-69]," Aug. 5, 1997.
GenBank Accession No. ETH84293, "acetoacetyl-CoA reductase [Bordetella pertussis STO1-CHOC-0017]," Dec. 13, 2013.
GenBank Accession No. SAK89949, "acetyacetyl-CoA reductase [Caballeronia arationis]," Nov. 22, 2016.
GenBank Accession No. AMP00485, "acetoacetyl-CoA reductase [Collimonas arenae]," Mar. 9, 2016.
Geneseq Accession No. AEH29045, "R. eutropha 3-keto acyl-CoA reductase mutant SEQ ID No. 2," Jun. 29, 2006.
Geneseq Accession No. AEH29048, "R. eutropha 3-keto acyl-CoA reductase mutant SEQ ID No. 5," Jun. 29, 2006.
Geneseq Accession No. AZQ30041, "R. eutrophus phaA gene encoded acetoacetyl-CoA thiolase/synthase, SEQ 16," Feb. 2, 2012.
Geneseq Accession No. AZQ30043, "Rastonia eutrophus 3-hydroxybutyryl-CoA dehydrogenase, SEQ ID 18," Feb. 2, 2012.
Gibbs et al., "Degenerate oligonucleotide gene shuffling (DOGS): a method for enhancing the frequency of recombination with family shuffling," *Gene*, 271:13-20 (2001).
Hayes et al., "Combining computational and experimental screening for rapid optimization of protein properties," *Proc. Natl. Acad. Sci. U.S.A.*, 99(25):15926-15931 (2002).
Hibbert et al., "Directed evolution of biocatalytic processes," *Biomol. Eng.*, 22:11-19 (2005).
Hoffmeister et al., "Mitochondrial trans-2-Enoyl-CoA Reductase of Wax Ester Fermentation from Euglena gracilis Defines a New Family of Enzymes Involved in Lipid Synthesis," *J. Biol. Chem.*, 280(6):4329-4338 (2005).
Houghten, "General method for the rapid solid-phase synthesis of large numbers of peptides: specificity of antigen-antibody interaction at the level of individual amino acids," *Proc. Natl. Acad. Sci., USA*, 82:5131-5135 (1985).
Huisman et al., "Enzyme Evolution for Chemical Process Applications," *Biocatalysis in the Pharmaceutical and Biotechnology Industries*, R N. Patel (ed.), CRC Press, Boca Raton, FL, Chapter 30, pp. 717-742 (2007).
Jeon et al., "Biosynthesis of poly(3-hydroxybutyrate-co-3-hydroxyhexanoate) (P(HB-co-HHx)) from butyrate using engineered Ralstonia eutropha," *Appl. Microbiol. Biotechnol.*, 98(12):5461-5469 (2014).
Karlen et al., "Absolute determination of the activity of two C14 dating standards," *Arkiv Geofysik*, 4:465-471 (1968).
Kretz et al., "Gene site saturation mutagenesis: a comprehensive mutagenesis approach," *Methods Enzymol.*, 388:3-11 (2004).
Lee et al., "A new approach to directed gene evolution by recombined extension on truncated templates (RETT)," *J. Molec. Catalysis*, 26:119-129 (2003).
Lin et al., "Fed-Batch Culture of a Metabolically Engineered *Escherichia coli* Strain Designed for High-Level Succinate Production and Yield Under Aerobic Conditions," *Biotechnol. Bioeng.*, 90:775-779 (2005).
Low et al., "Mimicking somatic hypermutation: affinity maturation of antibodies displayed on bacteriophage using a bacterial mutator strain," *J. Mol. Biol.*, 260(3):359-368 (1996).
Lutz et al., "Creating multiple-crossover DNA libraries independent of sequence identity," *Proc. Natl. Acad. Sci. U.S.A.*, 98(20):11248-11253 (2001).
Lutz et al., "Rapid generation of incremental truncation libraries for protein engineering using α-phosphothioate nucleotides," *Nucleic Acids Res.*, 15:29(4):e16 (2001).
Mann, "An International Reference Material for Radiocarbon Dating," *Radiocarbon*, 25(2):519-527 (1983).
Motsumoto et al., "Directed evolution and structural analysis of NADPH-dependent Acetoacetyl Coenzyme A (Acetoacetyl-CoA) reductase from Ralstonia eutropha reveals two mutations responsible for enhanced kinetics," *Appl. Environ. Microbiol.*, 79(19):6134-6139 (2013).
Muller et al., "Nucleotide exchange and excision technology (NExT) DNA shuffling: a robust method for DNA fragmentation and directed evolution," *Nucleic Acids Res.*, 33:e117 (2005).
Ness et al., "Synthetic shuffling expands functional protein diversity by allowing amino acids to recombine independently," *Nat. Biotechnol.*, 20(12):1251-1255 (2002).
Ostermeier et al., "A combinatorial approach to hybrid enzymes independent of DNA homology," *Nat. Biotechnol.*, 17(12):1205-1209 (1999).
Ostermeier et al., "Combinatorial protein engineering by incremental truncation," *Proc. Natl. Acad. Sci. U.S.A.*, 96(7):3562-3567 (1999).
Otten et al., "Directed evolution: selecting today's biocatalysts," *Biomol.Eng.*, 22:1-9 (2005).
Pritchard et al., "A general model of error-prone PCR," *J. Theor. Biol.*, 234:497-509 (2005).
Rajpal et al., "A general method for greatly improving the affinity of antibodies by using combinatorial libraries," *Proc. Natl. Acad. Sci. U.S.A.*, 102(24):8466-8471 (2005).
Reetz et al., "Directed Evolution of an Enantioselective Enzyme through Combinatorial Multiple-Cassette Mutagenesis," *Agnew. Chem. Int. Ed. Engl.*, 40:3589-3591 (2001).
Reetz et al., "Iterative saturation mutagenesis (ISM) for rapid directed evolution of functional enzymes," *Nat. Protoc.*, 2(4):891-903 (2007).
Reetz et al., "Iterative Saturation Mutagenesis on the Basis of B Factors as a Strategy for Increasing Protein Thermostability," *Agnew. Chem. Int. Ed. Engl.*, 45:7745-7751 (2006).
Reidhaar-Olson et al., "Combinatorial cassette mutagenesis as a probe of the informational content of protein sequences," *Science*, 241(4861):53-57 (1988).
Reidhaar-Olson et al., "Random mutagenesis of protein sequences using oligonucleotide cassettes," *Methods Enzymol.*, 208:564-586 (1991).
Selifonova et al., "Rapid evolution of novel traits in microorganisms," *Appl. Environ. Microbiol.*, 67(8):3645-3649 (2001).
Sen et al., "Developments in directed evolution for improving enzyme functions," *Appl. Biochem. Biotechnol.*, 143(3):212-223 (2007).
Shao et al., "Random-priming in vitro recombination: an effective tool for directed evolution," *Nucleic Acids Res.*, 26(2):681-683 (1998).
Sieber et al., "Libraries of hybrid proteins from distantly related sequences," *Nat. Biotechnol.*, 19(5):456-460 (2001).

(56) References Cited

OTHER PUBLICATIONS

Stemmer, "DNA Shuffling by random fragmentation and reassembly: in vitro recombination for molecular evolution," *Proc. Natl. Acad. Sci. U.S.A.*, 91(22):10747-10751 (1994).
Stemmer, "Rapid evolution of a protein in vitro by DNA shuffling," *Nature*, 370:389-391 (1994).
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27(18):e18 (1999).
Wong et al., "Sequence satruation mutagenesis with tunable mutation frequencies," *Anal. Biochem.*, 341:187-189 (2005).
Wong et al., "Sequence saturation mutagenesis (SeSaM): a novel method for directed evolution," *Nucleic Acids Res.*, 32(3):e26 (2004).
Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3:74-82 (2008).
Zhao et al., "Molecular evolution by staggered extension process (StEP) in vitro recombination," *Nat. Biotechnol.*, 16(3):258-261 (1998).

\* cited by examiner ered to produce desired products, engineered enzymes that facilitate production of a desired product, and more specifically to enzymes and cells that produce desired products such as 3-hydroxybutyryl-CoA, 3-hydroxybutyraldehyde, 1,3-butanediol, and related products and products derived therefrom.

```
                         SEQUENCE LISTING

<160> NUMBER OF SEQ ID NOS: 6

<210> SEQ ID NO 1
<211> LENGTH: 741
<212> TYPE: DNA
<213> ORGANISM: Artificial Sequence
<220> FEATURE:
<223> OTHER INFORMATION: Synthetic polynucleotide

<400> SEQUENCE: 1
atgactcagc gcattgcgta tgtgaccggc ggcatgggtg gtatcggaac cgccatttgc      60
cagcggctgg ccaaggatgg ctttcgtgtg gtggccggtt gcggccccaa ctcgccgcgc     120
cgcgaaaagt ggctggagca gcagaaggcc ctgggcttcg atttcattgc ctcggaaggc     180
aatgtggctg actgggactc gaccaagacc gcattcgaca aggtcaagtc cgaggtcggc     240
gaggttgatg tgctgatcaa caacgccggt atcacccgcg acgtggtgtt ccgcaagatg     300
acccgcgccg actgggatgc ggtgatcgac accaacctga cctcgctgtt caacgtcacc     360
aagcaggtga tcgacggcat ggccgaccgt ggctgggcc gcatcgtcaa catctcgtcg      420
gtgaacgggc agaagggcca gttcggccag accaactact ccaccgccaa ggccggcctg     480
catggcttca ccatggcact ggcgcaggaa gtggcgacca agggcgtgac cgtcaacacg     540
gtctctccgg ctatatcgc caccgacatg gtcaaggcga tccgccagga cgtgctcgac      600
aagatcgtcg cgacgatccc ggtcaagcgc ctgggcctgc cggaagagat cgcctcgatc     660
tgcgcctggt tgtcgtcgga ggagtccggt ttctcgaccg cgccgactt ctcgctcaac       720 ggcggcctgc atatgggctg a                                               741

<210> SEQ ID NO 2
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 2

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140
```

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
            165                 170                 175

Thr Val Asn Thr Val Ser Pro Gly Tyr Ile Ala Thr Asp Met Val Lys
        180                 185                 190

Ala Ile Arg Gln Asp Val Leu Asp Lys Ile Val Ala Thr Ile Pro Val
    195                 200                 205

Lys Arg Leu Gly Leu Pro Glu Glu Ile Ala Ser Ile Cys Ala Trp Leu
210                 215                 220

Ser Ser Glu Glu Ser Gly Phe Ser Thr Gly Ala Asp Phe Ser Leu Asn
225                 230                 235                 240

Gly Gly Leu His Met Gly
            245

<210> SEQ ID NO 3
<211> LENGTH: 1182
<212> TYPE: DNA
<213> ORGANISM: Artificial Sequence
<220> FEATURE:
<223> OTHER INFORMATION: Synthetic polynucleotide

<400> SEQUENCE: 3

```
atgactgacg ttgtcatcgt atccgccgcc cgcaccgcgg tcggcaagtt tggcggctcg      60
ctggccaaga tcccggcacc ggaactgggt gccgtggtca tcaaggccgc gctggagcgc     120
gccggcgtca agccggagca ggtgagcgaa gtcatcatgg ccaggtgct gaccgccggt      180
tcgggccaga accccgcacg ccaggccgcg atcaaggccg gcctgccggc gatggtgccg     240
gccatgacca tcaacaaggt gtgcggctcg ggcctgaagg ccgtgatgct ggccgccaac     300
gcgatcatgg cgggcgacgc cgagatcgtg gtggccggcg gccaggaaaa catgagcgcc     360
gccccgcacg tgctgccggg ctcgcgcgat ggtttccgca tgggcgatgc caagctggtc     420
gacaccatga tcgtcgacgg cctgtgggac gtgtacaacc agtaccacat gggcatcacc     480
gccgagaacg tggccaagga atacggcatc acacgcgagg cgcaggatga gttcgccgtc     540
ggctcgcaga acaaggccga agccgcgcag aaggccggca agtttgacga gagatcgtc      600
ccggtgctga tcccgcagcg caagggcgac ccggtggcct tcaagaccga cgagttcgtg     660
cgccagggcg ccacgctgga cagcatgtcc ggcctcaagc ccgccttcga caaggccggc     720
acggtgaccg cggccaacgc ctcgggcctg aacgacggcg ccgccgcggt ggtggtgatg     780
tcggcggcca aggccaagga actgggcctg accccgctgg ccacgatcaa gagctatgcc     840
aacgccggtg tcgatcccaa ggtgatgggc atgggcccgg tgccggcctc caagcgcgcc     900
ctgtcgcgcg ccgagtggac cccgcaagac ctggacctga tggagatcaa cgaggccttt     960
gccgcgcagg cgctggcggt gcaccagcag atgggctggg acacctccaa ggtcaatgtg    1020
aacggcggcg ccatcgccat cggccacccg atcgcgcgt cgggctgccg tatcctggtg     1080
acgctgctgc acgagatgaa gcgccgtgac gcgaagaagg gcctggcctc gctgtgcatc    1140
ggcggcggca tgggcgtggc gctggcagtc gagcgcaaat aa                       1182
```

<210> SEQ ID NO 4
<211> LENGTH: 393
<212> TYPE: PRT
<213> ORGANISM: Artificial Sequence
<220> FEATURE:
<223> OTHER INFORMATION: Synthetic polypeptide

<400> SEQUENCE: 4

```
Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
            20                  25                  30

Val Ile Lys Ala Ala Leu Glu Arg Ala Gly Val Lys Pro Glu Gln Val
        35                  40                  45

Ser Glu Val Ile Met Gly Gln Val Leu Thr Ala Gly Ser Gly Gln Asn
    50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
        115                 120                 125

Arg Asp Gly Phe Arg Met Gly Asp Ala Lys Leu Val Asp Thr Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
        195                 200                 205

Gly Asp Pro Val Ala Phe Lys Thr Asp Glu Phe Val Arg Gln Gly Ala
    210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
    290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
        355                 360                 365

Arg Asp Ala Lys Lys Gly Leu Ala Ser Leu Cys Ile Gly Gly Gly Met
    370                 375                 380

Gly Val Ala Leu Ala Val Glu Arg Lys
385                 390
```

-continued

<210> SEQ ID NO 5
<211> LENGTH: 1179
<212> TYPE: DNA
<213> ORGANISM: Artificial Sequence
<220> FEATURE:
<223> OTHER INFORMATION: Synthetic polynucleotide

<400> SEQUENCE: 5

```
atgagagatg tagtaatagt aagtgctgta agaactgcaa taggagcata tggaaaaaca      60
ttaaaggatg tacctgcaac agagttagga gctatagtaa taaggaagc tgtaagaaga     120
gctaatataa atccaaatga gattaatgaa gttattttg gaaatgtact tcaagctgga     180
ttaggccaaa acccagcaag acaagcagca gtaaaagcag gattaccttt agaaacacct     240
gcgtttacaa tcaataaggt ttgtggttca ggtttaagat ctataagttt agcagctcaa     300
attataaaag ctggagatgc tgataccatt gtagtaggtg gtatggaaaa tatgtctaga     360
tcaccatatt tgattaacaa tcagagatgg ggtcaaagaa tgggagatag tgaattagtt     420
gatgaaatga taaaggatgg tttgtgggat gcatttaatg gatatcatat gggagtaact     480
gcagaaaata ttgcagaaca atggaatata caagagaag agcaagatga attttcactt     540
atgtcacaac aaaaagctga aaaagccatt aaaaatggag aatttaagga tgaaatagtt     600
cctgtattaa taaagactaa aaaaggtgaa atagtctttg atcaagatga atttcctaga     660
ttcggaaaca ctattgaagc attaagaaaa cttaaaccta ttttcaagga aaatggtact     720
gttacagcag gtaatgcatc cggattaaat gatggagctg cagcactagt aataatgagc     780
gctgataaag ctaacgctct cggaataaaa ccacttgcta agattacttc ttacggatca     840
tatggggtag atccatcaat aatgggatat ggagcttttt atgcaactaa agctgcctta     900
gataaaatta atttaaaacc tgaagactta gatttaattg aagctaacga ggcatatgct     960
tctcaaagta tagcagtaac tagagattta aatttagata tgagtaaagt taatgttaat    1020
ggtggagcta tagcacttgg acatccaata ggtgcatctg gtgcacgtat tttagtaaca    1080
ttactatacg ctatgcaaaa aagagattca aaaaaaggtc ttgctactct atgtattggt    1140
ggaggtcagg gaacagctct cgtagttgaa agagactaa                           1179
```

<210> SEQ ID NO 6
<211> LENGTH: 392
<212> TYPE: PRT
<213> ORGANISM: Artificial Sequence
<220> FEATURE:
<223> OTHER INFORMATION: Synthetic polypeptide

<400> SEQUENCE: 6

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110
```

```
Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
    130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
        210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
        290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
    370                 375                 380

Thr Ala Leu Val Val Glu Arg Asp
385                 390
```

3-HYDROXYBUTYRYL-COA DEHYDROGENASE VARIANTS AND METHODS OF USE

CROSS-REFERENCE

This application is a United States National Stage Application under 35 U.S.C. § 371 of International Patent Application No. PCT/US2018/025086, filed Mar. 29, 2018, which claims the benefit of priority to U.S. Provisional Patent Application Serial No. (USSN) 62/480,208, filed Mar. 31, 2017, the entire contents of each of which are incorporated herein by reference.

Reference is made to the following provisional and international applications, which are incorporated herein by reference in their entireties: (1) U.S. Provisional Application No. 62/480,270 entitled, "PROCESS AND SYSTEMS FOR OBTAINING 1,3-BUTANEDIOL FROM FERMENTATION BROTHS," filed Mar. 31, 2017; (2) U.S. Provisional Application No. 62/480,194 entitled "ALDEHYDE DEHYDROGENASE VARIANTS AND METHODS OF USE," filed Mar. 31, 2017; (3) International Patent Application No. PCT/US2018/025068 entitled, "PROCESS AND SYSTEMS FOR OBTAINING 1,3-BUTANEDIOL FROM FERMENTATION BROTHS," filed Mar. 29, 2018; and (4) International Patent Application No. PCT/US2018/025122 entitled, "ALDEHYDE DEHYDROGENASE VARIANTS AND METHODS OF USE," filed Mar. 29, 2018.

SEQUENCE LISTING

Incorporated herein by reference is the Sequence Listing being concurrently submitted via EFS-Web as an ASCII text file named "12956-409-999_Sequence_Listing.txt," created on Sep. 26, 2019 and being 14,068 bytes in size.

BACKGROUND OF THE INVENTION

The present invention relates generally to organisms engineered to produce desired products, engineered enzymes that facilitate production of a desired product, and more specifically to enzymes and cells that produce desired products such as 3-hydroxybutyryl-CoA, 3-hydroxybutyraldehyde, 1,3-butanediol, and related products and products derived therefrom.

Various commodity chemicals are used to make desired products for commercial use. Many of the commodity chemicals are are derived from petroleum. Such commodity chemicals have various uses, including use as solvents, resins, polymer precursors, and specialty chemicals. Desired commodity chemicals include 4-carbon molecules such as 1,4-butanediol and 1,3-butanediol, upstream precursors and downstream products. It is desirable to develop methods for production of commodity chemicals to provide renewable sources for petroleum-based products and to provide less energy- and capital-intensive processes.

Thus, there exists a need for methods that facilitate production of desired products. The present invention satisfies this need and provides related advantages as well.

SUMMARY OF INVENTION

In some aspects, the present disclosure provides isolated nucleic acid molecules. In some embodiments, the isolated nucleic acid molecule is selected from: (a) a first nucleic acid molecule encoding a first variant of a reference polypeptide, wherein (i) the reference polypeptide has an amino acid sequence of SEQ ID NO: 2, (ii) the first variant comprises one or more amino acid substitutions relative to SEQ ID NO: 2, and (iii) the one or more amino acid substitutions are selected from Table 1; (b) a second nucleic acid molecule encoding a second variant of the reference polypeptide, wherein the second variant (i) comprises one or more amino acid substitutions of a corresponding variant selected from Table 1, and (ii) has at least 50%, 65%, 70%, 75%, 80%, 85%, 90%, 95%, 98% 99%, or 100% sequence identity to the corresponding variant; (c) a third nucleic acid molecule that hybridizes to the first or second nucleic acid molecule under highly stringent hybridization conditions and comprises a nucleic acid sequence that encodes the one or more amino acid substitutions; and (d) a fourth nucleic acid molecule that is complementary to the first nucleic acid molecule, the second nucleic acid molecule, or the third nucleic acid molecule; wherein the first variant, the second variant, the third variant, and the fourth variant are not naturally occurring.

In some embodiments, the isolated nucleic acid molecule encodes a variant 3-hydroxybutyryl-CoA dehydrogenase having an increased ability to utilize NADH as a cofactor in a reaction converting acetoacetyl-CoA to 3-hydroxybutyryl-CoA, relative to a reference 3-hydroxybutyryl-CoA dehydrogenase consisting of amino acid sequence SEQ ID NO: 2. In some embodiments, the ability of the variant 3-hydroxybutyryl-CoA dehydrogenase to use NADH as a cofactor is at least 1.2-fold higher, 3-fold higher, 5-fold higher, or between 1.2-fold to 10-fold higher, as compared to the reference 3-hydroxybutyryl-CoA dehydrogenase. In some embodiments, the isolated nucleic acid molecule is the second nucleic acid molecule, and the second variant has at least 80%, 90%, or 95% sequence identity to the corresponding variant selected from Table 1.

In some aspects, the present disclosure provides isolated polypeptide variants, such as variants of a reference polypeptide. In some embodiments, the reference polypeptide has an amino acid sequence of SEQ ID NO: 2, and the polypeptide variant is selected from Table 1 and has one or more amino acid substitutions relative to SEQ ID NO: 2. In some embodiments, the polypeptide variant comprises a sequence having at least 50% identity to SEQ ID NO: 2 or to a variant selected from Table 1; and the polypeptide variant comprises an amino acid substitution corresponding to one or more positions of SEQ ID NO: 2 selected from C34, G35, P36, N37, S38, and R40. In some embodiments, (i) the amino acid corresponding to C34 is replaced with A, D, E, H, I, L, M, S, T, V, or Y; (ii) the amino acid corresponding to G35 is replaced with C, D, E, F, H, I, K, L, M, P, Q, R, S, T, V, or Y; (iii) the amino acid corresponding to P36 is replaced with S; (iv) the amino acid corresponding to N37 is replaced with K; (v) the amino acid corresponding to S38 is replaced with A, C, D, E, F, G, H, I, K, L, M, Q, T, V, W, or Y; (vi) the amino acid corresponding to R40 is replaced with A, D, E, F, G, H, I, K, L, M, N, P, Q, S, T, V, or Y; or (vii) two or more of (i)-(vi) in any combination. In some embodiments, the polypeptide variant comprises a sequence having at least 50% identity to SEQ ID NO: 2 or a variant selected from Table 1; and the polypeptide variant comprises 1, 2, 3, 4, 5, or more amino acid substitutions relative to SEQ ID NO: 2 selected from: A103M, A107V, A156S, A158R, A193R, A204T, C20F, C34A, C34D, C34E, C34H, C34I, C34L, C34M, C34S, C34T, C34V, C34Y, D104A, D104E, D104Q, D106H, D129E, D236C, D236V, E215H, E215W, E42Q, E46C, E46S, E78K, F55I, G241G, G35*, G35A, G35C, G35D, G35E, G35F, G35H, G35I, G35K, G35L, G35M, G35P, G35Q, G35R, G35S, G35T, G35V, G35Y, G90V, K209Q, L160A, L160M, L167Q, L213N, L243A, L243I, L243V, N112C, N112D, N112H, N37K, P207Q, P36S, Q144Q, Q47L, Q47L, Q48Q, R40A, R40D, R40E, R40F, R40G, R40H, R40I, R40K, R40L, R40M, R40N, R40P, R40Q, R40S, R40T, R40V, R40Y, R41H, R98C, S115R, S38A, S38C, S38D, S38E, S38F, S38G, S38H, S38I, S38K, S38L, S38M, S38Q, S38T, S38V, S38W, S38Y, T114C, T155C, T173S, T205N, T205Q, T92H, T92N, V203I, and V31I. In some embodiments, the polypeptide variant comprises a sequence having at least 80%, 90%, 95%, or 99% sequence identity to SEQ ID NO: 2 or a variant selected from Table 1.

In some embodiments, the isolated polypeptide variant is a variant of a first reference polypeptide, wherein (a) the first reference polypeptide has an amino acid sequence of SEQ ID NO: 2, (b) the polypeptide variant comprises one or more amino acid substitutions relative to SEQ ID NO: 2, (c) the one or more amino acid substitutions are selected from Table 1, and (d) the polypeptide variant has at least 65%, 70%, 75%, 80%, 85%, 90%, 95%, 98%, or 99% sequence identity to a corresponding variant selected from Table 1. In some embodiments, the polypeptide variant has at least 80%, 90%, or 95% sequence identity to the corresponding variant selected from Table 1. In some embodiments, the polypeptide variant further comprises a conservative amino acid substitution in from 1 to 100 modified amino acid positions relative to the corresponding first reference polypeptide, wherein said modified positions are other than the one or more amino acid substitutions of a second reference polypeptide.

In some embodiments, polypeptide variants disclosed herein have one or more additional characteristics. In some embodiments, the one or more amino acid substitutions comprise at least 2, 3, 4, 5, 6, 7, 8, 9, or 10 amino acid substitutions selected from Table 1. In some embodiments, the polypeptide variant comprises no modification at from 2 to 300 unmodified amino acid positions compared to the first reference polypeptide, wherein said unmodified positions are selected from those that are identical to between 2, 3, 4, or 5 amino acid sequences referenced in Table 2. In some embodiments, the polypeptide can convert acetoacetyl-CoA to 3-hydroxybutyryl-CoA. In some embodiments, the isolated polypeptide variant is a 3-hydroxybutyryl-CoA dehydrogenase having an increased ability to utilize NADH as a cofactor in a reaction converting acetoacetyl-CoA to 3-hydroxybutyryl-CoA, relative to a reference 3-hydroxybutyryl-CoA dehydrogenase encoded by SEQ ID NO: 2.

In some aspects, the disclosure provides isolated nucleic acid molecules comprising a sequence encoding an isolated polypeptide, such as a polypeptide variant described herein.

In some aspects, the disclosure provides vectors containing a nucleic acid molecule disclosed herein, such as an expression vector.

In some aspects, the present disclosure provides cells. In some embodiments, a cell comprises a vector, a polypeptide variant, and/or a nucleic acid molecule disclosed herein. In some embodiments, the nucleic acid molecule is integrated into a chromosome of the cell, such as a site-specific integration. In some embodiments, the cell is a microbial organism, such as a bacterium, a yeast, or a fungus. In some embodiments, the cell is a eukaryotic cell. In some embodiments, the cell comprises a pathway that produces 3-hydroxybutyryl-CoA, 3-hydroxybutyraldehyde (3HBal), 3-hydroxybutyrate (3-HB), 1,3-butanediol (1,3-BDO), and/or an ester or amide thereof. In some embodiments, the nucleic acid molecule is expressed. In some embodiments, the cell is capable of fermentation. In some embodiments, the cell comprises at least one substrate for a 3-hydroxybutyryl-CoA dehydrogenase encoded by the nucleic acid molecule, such as acetoacetyl-CoA. In some embodiments, the cell comprises a polynucleotide encoding a thiolase with at least 80%, 85%, 90%, 95%, 98% 99%, or 100% amino acid sequence identity to SEQ ID NO: 4. In some embodiments, the thiolase comprises the amino acid sequence of SEQ ID NO: 4. In some embodiments, the cell produces an increased amount of 1,3-BDO when cultured for at least 30 or 40 hours under conditions comprising a peak weight-based oxygen uptake rate of about 50 mmol $O_2$/kg/hr, 40 mmol $O_2$/kg/hr, 30 mmol $O_2$/kg/hr, 25 mmol $O_2$/kg/hr, or lower, as compared to a cell in which the thiolase instead comprises the amino acid sequence of SEQ ID NO: 6, optionally wherein the increased amount of 1,3-BDO is an increase of at least 1%, 2%, 3%, 4%, 5%, 10%, 15%, 20%, 25%, 30%, 35%, 40%, or 50%. In some embodiments, the cell produces a decreased amount of pyruvate when cultured for at least 30 or 40 hours under conditions comprising a peak weight-based oxygen uptake rate of about 50 mmol $O_2$/kg/hr, 40 mmol $O_2$/kg/hr, 30 mmol $O_2$/kg/hr, 25 mmol $O_2$/kg/hr, or lower, as compared to a cell in which the thiolase instead comprises the amino acid sequence of SEQ ID NO: 6, optionally wherein the decreased amount of pyruvate is a decrease of at least 1%, 5%, 10%, 15%, 20%, 25%, 30%, 40%, 50%, 60%, 70%, or 80%. In some embodiments, the cell produces 1,3-BDO and pyruvate at an increased ratio of 1,3-BDO to pyruvate when cultured for at least 30 or 40 hours under conditions comprising a peak weight-based oxygen uptake rate of about 50 mmol $O_2$/kg/hr, 40 mmol $O_2$/kg/hr, 30 mmol $O_2$/kg/hr, 25 mmol $O_2$/kg/hr, or lower, as compared to a cell in which the thiolase instead comprises the amino acid sequence of SEQ ID NO: 6, optionally wherein the increased ratio is increased by at least 1.5-fold, 2-fold, 3-fold, 4-fold, 5-fold, 5-fold, 6-fold, 7-fold, 8-fold, 9-fold, or 10-fold.

In some aspects, the present disclosure provides uses of polypeptide variants described herein. In some embodiments, the polypeptide variant is used as a biocatalyst.

In some aspects, the present disclosure provides compositions comprising a polypeptide variant described herein. In some embodiments, the composition comprises the polypeptide variant and at least one substrate for the polypeptide variant, such as acetoacetyl-CoA. In some embodiments, the polypeptide variant can react with said substrate under in vitro conditions. In some embodiments, the composition further comprises a thiolase with at least 80%, 85%, 90%, 95%, 98% 99%, or 100% amino acid sequence identity to SEQ ID NO: 4. In some embodiments, the thiolase comprises the amino acid sequence of SEQ ID NO: 4. In some embodiments, the thiolase exhibits a reduced oxygen sensitivity in converting two acetyl-CoA molecules to acetoacetyl-CoA as compared to a thiolase comprising the amino acid sequence of SEQ ID NO: 6.

In some aspects, the present disclosure provides a culture medium. In some embodiments, the culture medium comprises a cell described herein. In some embodiments, the culture medium comprises bioderived 3-HB-CoA, 3-HBal, 3-HB, and/or 1,3-BDO, wherein (a) the bioderived 3-HB-CoA, 3-HBal, 3-HB, and/or 1,3-BDO has a carbon-12, carbon-13, and carbon-14 isotope ratio that reflects an atmospheric carbon dioxide uptake source; and (b) the bioderived 3-HB-CoA, 3-HBal, 3-HB, and/or 1,3-BDO is produced by (i) a cell described herein, or (ii) a method described herein. In some embodiments, the culture medium is separated from a non-naturally occurring microbial organism having a pathway that produces 3-HB-CoA, 3-HBal, 3-HB, and/or 1,3-BDO.

In some aspects, the present disclosure provides a method for constructing a host strain comprising introducing a vector described herein into a cell capable of fermentation. In some aspects, the present disclosure provides a method for producing a polypeptide variant disclosed herein, the method comprising: (a) expressing the polypeptide in a cell, or (b) in vitro transcribing and translating a nucleic acid molecule or vector described herein.

In some aspects, the present disclosure provides methods for producing 3-hydroxybutyryl-CoA (3-HB-CoA), 3-hydroxybutyraldehyde (3-HBal), 3-hydroxybutyrate (3-HB), and/or 1,3-butanediol (1,3-BDO), and methods for producing 3-hydroxybutyryl-CoA (3-HB-CoA), 3-hydroxybutyraldehyde (3-HBal), 3-hydroxybutyrate (3-HB), 1,3-butanediol (1,3-BDO), and/or an ester or amide thereof. In some embodiments, the method comprises culturing a cell disclosed herein, wherein the culturing is under conditions and for a sufficient period of time to produce 3-HB-CoA, 3-HBal, 3-HB, and/or 1,3-BDO. In some embodiments, the cell is in a substantially anaerobic culture medium. In some embodiments, the method further comprises isolating or purifying the 3-HB-CoA, 3-HBal, 3-HB, 1,3-BDO, and/or an ester or amide thereof. In some embodiments, the method further comprises distillation. In some embodiments, the method comprises providing a substrate for a polypeptide variant of the disclosure, and converting the substrate to 3-HB-CoA, 3-HBal, 3-HB, or 1,3-BDO through one or more reactions. In some embodiments, the polypeptide variant is present in a cell, in a cell lysate, or is isolated from a cell or cell lysate. In some embodiments, the method comprises incubating a lysate of a cell disclosed herein to produce the 3-HB-CoA, 3-HBal, 3-HB, and/or 1,3-BDO. In some embodiments, the cell lysate is mixed with a second cell lysate, and the second cell lysate comprises an enzymatic activity to produce a substrate of the polypeptide variant, or a downstream product of 3-HB-CoA, 3-HBa1,3-HB, and/or 1,3-BDO.

In some aspects, the present disclosure provides bioderived compositions. In some embodiments, the bioderived composition comprises 3-HB-CoA, 3-HBal, 3-HB, and/or 1,3-BDO having a carbon-12, carbon-13, and carbon-14 isotope ratio that reflects an atmospheric carbon dioxide uptake source, and wherein the 3-HB-CoA, 3-HBal, 3-HB, and/or 1,3-BDO is produced by (a) a cell disclosed herein, or (b) a method disclosed herein. In some embodiments, the -HB-CoA, 3-HBal, 3-HB, and/or 1,3-BDO has an Fm value of at least 80%, at least 85%, at least 90%, at least 95% or at least 98%. In some embodiments, the bioderived composition comprises 3-HB-CoA, 3-HBal, 3-HB, and/or 1,3-BDO produced according to a method disclosed herein.

In some aspects, the present disclosure provides compositions comprising bioderived compositions described herein. In some embodiments, the composition comprises a bioderived 3-HB-CoA, 3-HBal, 3-HB, and/or 1,3-BDO described herein, and a compound other than the bioderived 3-HB-CoA, 3-HBal, 3-HB, and/or 1,3-BDO. In some embodiments, the compound other than the bioderived 3-HB-CoA, 3-HBal, 3-HB, and/or 1,3-BDO is (a) a portion of a cell that produces the 3-HB-CoA, 3-HBal, 3-HB, and/or 1,3-BDO, or (b) a cell that expresses a polypeptide variant disclosed herein. In some embodiments, the composition comprises a bioderived 3-HB-CoA, 3-HBal, 3-HB, and/or 1,3-BDO described here, or a cell lysate or culture supernatant of a microbial organism producing the bioderived 3-HB-CoA, 3-HBal, 3-HB, and/or 1,3-BDO.

In some aspects, the present disclosure provides biobased products. In some embodiments, the biobased product comprises a bioderived 1,3-BDO described herein, wherein the biobased product is a plastic, an elastic fiber, a polyurethane, a polyester, a polyhydroxyalkanoate, a poly-4-hydroxybutyrate (P4HB), a poly(tetramethylene ether) glycol (PT-MEG), a polybutylene terephthalate (PBT), a polyurethane-polyurea copolymer, a nylon, an organic solvent, a polyurethane resin, a polyester resin, a hypoglycaemic agent, a butadiene, or a butadiene-based product. In some embodiments, the biobased product is a cosmetic product or a food additive. In some embodiments, the biobased product comprises at least 5%, at least 10%, at least 20%, at least 30%, at least 40%, or at least 50% bioderived 1,3-BDO. In some embodiments, the biobased product comprises a portion of said bioderived 1,3-BDO as a repeating unit. In some embodiments, the product is a molded product, obtained by molding a biobased product described herein.

In some aspects, the present disclosure provides processes for producing biobased products disclosed herein. In some embodiments, the process comprises chemically reacting the bioderived 1,3-BDO with itself, a diacid, or another compound in a reaction that produces said biobased product. In some embodiments, the bioderived 1,3-BDO is converted to an ester by reacting with an acid and a lipase. In some embodiments, the acid is a diacid. In some embodiments, the biobased product comprises a ketone ester.

In some aspects, the present disclosure provides methods for producing 3-hydroxybutyryl-CoA (3-HB-CoA), 3-hydroxybutyraldehyde (3-HBal), 3-hydroxybutyrate (3-HB), and/or 1,3-butanediol (1,3-BDO). In some embodiments, the methods comprise (a) culturing a cell under conditions and for a sufficient period of time to produce 3-HB-CoA, 3-HBal, 3-HB, and/or 1,3-BDO; and (b) isolating or purifying the 3-HB-CoA, 3-HBal, 3-HB, 1,3-BDO, and/or an ester or amide thereof; wherein the cell comprises a polynucleotide encoding a thiolase with at least 80%, 85%, 90%, 95%, 98% 99%, or 100% amino acid sequence identity to SEQ ID NO: 4. In some embodiments, the thiolase comprises the amino acid sequence of SEQ ID NO: 4. In some embodiments, the thiolase exhibits a reduced oxygen sensitivity in converting two acetyl-CoA molecules to acetoacetyl-CoA as compared to a thiolase comprising the amino acid sequence of SEQ ID NO: 6. In some embodiments, the cell further comprises a second polynucleotide encoding a polypeptide with at least 80%, 85%, 90%, 95%, 98% 99%, or 100% amino acid sequence identity to SEQ ID NO: 2. In some embodiments, the polypeptide comprises SEQ ID NO: 2. In some embodiments, the polynucleotide encoding the thiolase is an exogenous polynucleotide, optionally wherein the polynucleotide encoding the thiolase is integrated into a genome of the cell. In some embodiments, the second polynucleotide is an exogenous polynucleotide, optionally wherein the second polynucleotide is integrated into a genome of the cell. In some embodiments, the culturing comprises a peak weight-based oxygen uptake rate of about 50 mmol $O_2$/kg/hr, 40 mmol $O_2$/kg/hr, 30 mmol $O_2$/kg/hr, 25 mmol $O_2$/kg/hr, or lower. In some embodiments, the cell produces an increased amount of 1,3-BDO when cultured for at least 30 or 40 hours as compared to a cell in which the thiolase instead comprises the amino acid sequence of SEQ ID NO: 6, optionally wherein the increased amount of 1,3-BDO is an increase of at least 1%, 2%, 3%, 4%, 5%, 10%, 15%, 20%, 25%, 30%, 35%, 40%, or 50%. In some embodiments, the cell produces a decreased amount of pyruvate when cultured for at least 30 or 40 hours as compared to a cell in which the thiolase instead comprises the amino acid sequence of SEQ ID NO: 6, optionally wherein the decreased amount of pyruvate is a decrease of at least 1%, 5%, 10%, 15%, 20%, 25%, 30%, 40%, 50%, 60%, 70%, or 80%. In some embodiments, the cell produces 1,3-BDO and pyruvate at an increased ratio of 1,3-BDO to pyruvate when cultured for at least 30 or 40 hours as compared to a cell in which the thiolase instead comprises the amino acid sequence of SEQ ID NO: 6, optionally wherein the increased ratio is increased by at least 1.5-fold, 2-fold, 3-fold, 4-fold, 5-fold, 5-fold, 6-fold, 7-fold, 8-fold, 9-fold, or 10-fold. In some embodiments, step (b) comprises distillation.

In some embodiments of any of the foregoing, the 1,3-BDO comprises R-1,3-butanediol (R-1,3-BDO). In some embodiments, the 1,3-BDO is about or at least about 10%, 25%, 50%, 75%, 80%, 85%, 90%, 95%, 96%, 97%, 98%, 99%, or 100% R-1,3-butanediol (R-1,3-BDO).

DETAILED DESCRIPTION OF THE INVENTION

Figure 1:
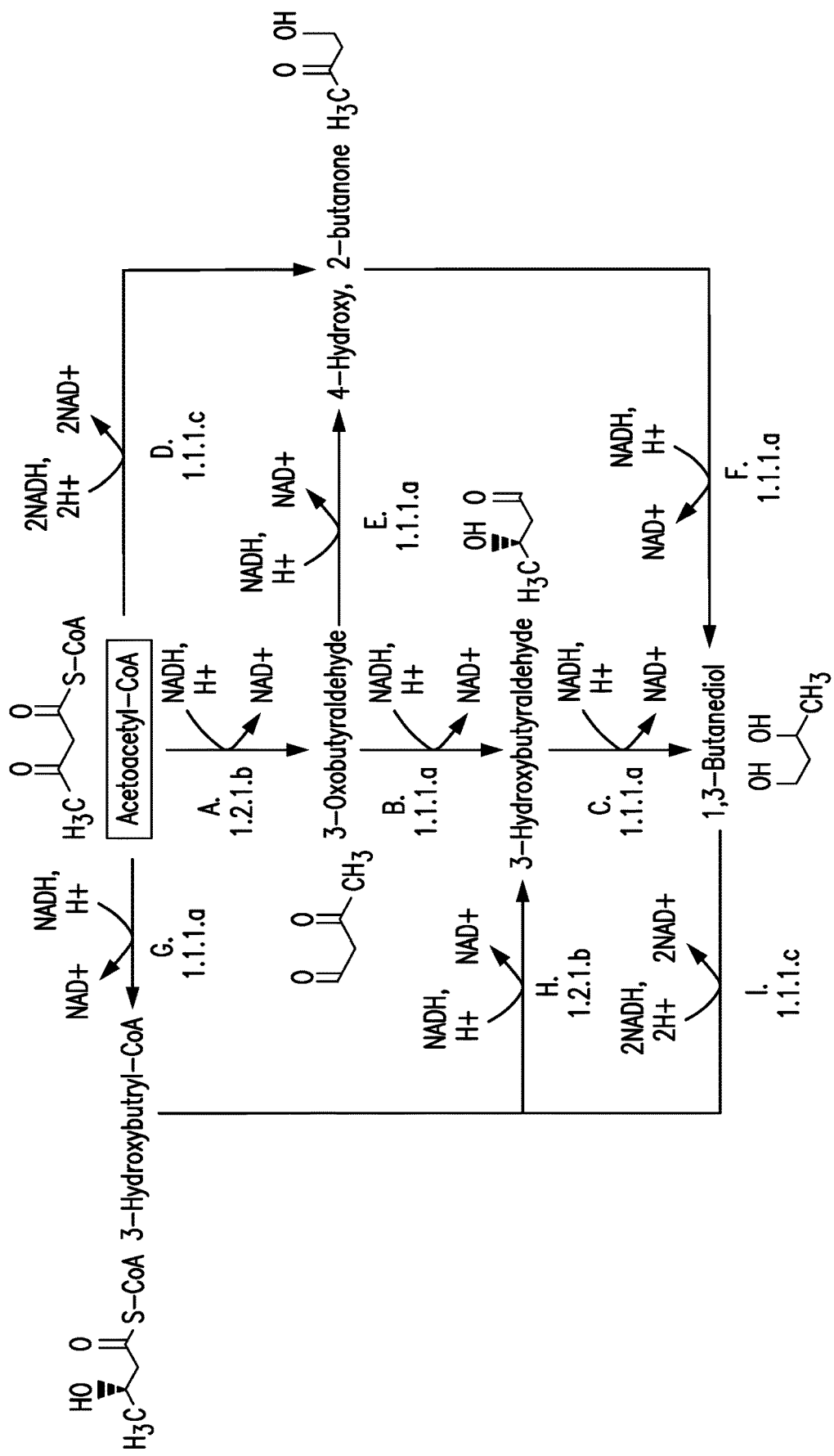
FIG. 1 shows an exemplary 1,3-butanediol (1,3-BDO) pathway that comprises a 3-hydroxybutyryl-CoA dehydrogenase. Illustrated is a pathway from acetoacetyl-CoA to 1,3-butanediol. The enzymes are: (A) acetoacetyl-CoA reductase (CoA-dependent, aldehyde forming); (B) 3-oxobutyraldehyde reductase (ketone reducing); (C) 3-hydroxybutyraldehyde reductase, also referred to herein as 1,3-butanediol dehydrogenase; (D) acetoacetyl-CoA reductase (CoA-dependent, alcohol forming); (E) 3-oxobutyraldehyde reductase (aldehyde reducing); (F) 4-hydroxy, 2-butanone reductase; (G) 3-hydroxybutyryl-CoA dehydrogenase also referred to herein as acetoacetyl-CoA reductase (ketone reducing); (H) 3-hydroxybutyryl-CoA reductase (aldehyde forming), also referred to herein as 3-hydroxybutyraldehyde dehydrogenase; and (I) 3-hydroxybutyryl-CoA reductase (alcohol forming).

In some aspects, the invention relates to methods for producing 3-hydroxybutyryl-CoA (3-HB-CoA), 3-hydroxybutyraldehyde (3-HBal), 3-hydroxybutyrate (3-HB), and/or 1,3-butanediol (1,3-BDO). In some embodiments, the method comprises (a) culturing a cell under conditions and for a sufficient period of time to produce 3-HB-CoA, 3-HBal, 3-HB, and/or 1,3-BDO; and (b) isolating or purifying the 3-HB-CoA, 3-HBal, 3-HB, 1,3-BDO, and/or an ester or amide thereof; wherein the cell comprises a polynucleotide encoding a thiolase with at least 80%, 85%, 90%, 95%, 98% 99%, or 100% amino acid sequence identity to SEQ ID NO: 4. In particular embodiments, use of the thiolase increases 1,3-BDO production, decreases oxygen sensitivity, decreases production of byproducts (e.g., pyruvate), and/or reduces oxygen uptake of the culture, as compared to use of a cell in which the thiolase instead comprises the amino acid sequence of SEQ ID NO: 6.

In some aspects, the invention relates to enzyme variants that have desirable properties and are useful for producing desired products. In a particular embodiment, the invention relates to 3-hydroxybutyryl-CoA dehydrogenase variants, which are enzyme variants that have markedly different structural and/or functional characteristics compared to a wild type enzyme that occurs in nature. Thus, the 3-hydroxybutyryl-CoA dehydrogenase variants are not naturally occurring enzymes. Such 3-hydroxybutyryl-CoA dehydrogenase variants are useful in an engineered cell, such as a microbial organism, that has been engineered to produce a desired product. For example, as disclosed herein, a cell, such as a microbial organism, having a metabolic pathway can produce a desired product. A 3-hydroxybutyryl-CoA dehydrogenase variant having desirable characteristics can be introduced into a cell, such as a microbial organism, that has a metabolic pathway that uses a 3-hydroxybutyryl-CoA dehydrogenase enzymatic activity to produce a desired product. Such 3-hydroxybutyryl-CoA dehydrogenase variants are additionally useful as biocatalysts for carrying out desired reactions in vitro. Thus, the 3-hydroxybutyryl-CoA dehydrogenase variants of the invention can be utilized in engineered cells, such as microbial organisms, to produce a desired product or as as an in vitro biocatalyst to produce a desired product. In some embodiments, a 3-hydroxybutyryl-CoA dehydrogenase variant is used in combination with a thiolase with at least 80%, 85%, 90%, 95%, 98% 99%, or 100% amino acid sequence identity to SEQ ID NO: 4.

As used herein, the term "non-naturally occurring" when used in reference to a cell, a microbial organism or microorganism is intended to mean that the cell has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the cell's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a biosynthetic pathway for producing a desired product.

A metabolic modification refers to a biochemical reaction that is altered from its naturally occurring state. Therefore, non-naturally occurring cells can have genetic modifications to nucleic acids encoding metabolic polypeptides, or functional fragments thereof. Exemplary metabolic modifications are disclosed herein.

As used herein, the term "isolated" when used in reference to a cell or microbial organism is intended to mean a cell that is substantially free of at least one component as the referenced cell is found in nature, if such a cell is found in nature. The term includes a cell that is removed from some or all components as it is found in its natural environment. The term also includes a cell that is removed from some or all components as the cell is found in non-naturally occurring environments. Therefore, an isolated cell is partly or completely separated from other substances as it is found in nature or as it is grown, stored or subsisted in non-naturally occurring environments. Specific examples of isolated cells include partially pure cells, substantially pure cells and cells cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "reduced oxygen sensitivity" generally refers to an activity level of an enzyme that is higher in the presence of a particular amount of oxygen than the corresponding activity of a reference enzyme, or exhibits a lower degree of inhibition by oxygen than the reference enzyme. In some embodiments, the reduced oxygen sensitivity is an oxygen sensitivity reduction of at least 5%, 10%, 15%, 20%, 25%, 30%, 40%, 50%, or more. Reduced oxygen sensitivity can be measured in terms of a lower inhibition constant ($K_i$), an increased rate of enzyme activity (e.g., a rate of converting two acetyl-CoA molecules to acetoacetyl-CoA) under particular reaction or culture conditions (e.g., an aeration condition, examples of which are described herein), an increased amount of product from a pathway including the enzyme (e.g. acetoacetyl-CoA, or a downstream product thereof) under particular reaction or culture conditions (e.g., an aeration condition), or a combination of two or more of these. In some embodiments, the enzyme having reduced oxygen sensitivity is a thiolase, and the reference enzyme is a thiolase having the sequence of SEQ ID NO: 6.

"Exogenous" as it is used herein is intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. When used in reference to a biosynthetic activity, the term refers to an activity that is introduced into the host reference organism. The source can be, for example, a homologous or heterologous encoding nucleic acid that expresses the referenced activity following introduction into the host cell. Therefore, the term "endogenous" refers to a referenced molecule or activity that is present in the host. Similarly, the term when used in reference to expression of an encoding nucleic acid refers to expression of an encoding nucleic acid contained within the cell. The term "heterologous" refers to a molecule or activity derived from a source other than the referenced species. Accordingly, exogenous expression of an encoding nucleic acid of the invention can utilize either or both a heterologous or homologous encoding nucleic acid.

It is understood that when more than one exogenous nucleic acid is included in a cell that the more than one exogenous nucleic acids refers to the referenced encoding nucleic acid or biosynthetic activity, as discussed above. It is further understood, as disclosed herein, that such more than one exogenous nucleic acids can be introduced into the host cell on separate nucleic acid molecules, on polycistronic nucleic acid molecules, or a combination thereof, and still be considered as more than one exogenous nucleic acid. For example, as disclosed herein a cell can be engineered to express two or more exogenous nucleic acids encoding a desired enzyme or protein, such as a pathway enzyme or protein. In the case where two exogenous nucleic acids encoding a desired activity are introduced into a host cell, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the non-naturally occurring cells of the invention. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given function. However, the attenuation of the activity or amount of an enzyme or protein that mimics complete disruption, for example, complete disruption for one pathway, can still be sufficient for a separate pathway to continue to function. For example, attenuation of an endogenous enzyme or protein can be sufficient to mimic the complete disruption of the same enzyme or protein for production of a desired product of the invention, but the remaining activity or amount of enzyme or protein can still be sufficient to maintain other pathways, such as a pathway that is critical for the host cell to survive, reproduce or grow. Attenuation of an enzyme or protein can also be weakening, reducing or diminishing the activity or amount of the enzyme or protein in an amount that is sufficient to increase yield of a desired product of the invention, but does not necessarily mimic complete disruption of the enzyme or protein.

The non-naturally occurring cells of the invention can contain stable genetic alterations, which refers to cells that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein, are described with reference to a suitable host cell or organism such as *E. coli* and their corresponding metabolic reactions or a suitable source cell or organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring cell. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring cells of the invention having biosynthetic capability for a desired product, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced cell that encode an enzyme catalyzing a similar or substantially similar metabolic reaction, those skilled in the art also can utilize these evolutionarily related genes. Similarly for a gene disruption, evolutionarily related genes can also be disrupted or deleted in a host cell to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides a 3-hydroxybutyryl-CoA dehydrogenase that is a variant of a wild type or parent 3-hydroxybutyryl-CoA dehydrogenase. The 3-hydroxybutyryl-CoA dehydrogenase of the invention converts acetoacetyl-CoA to 3-hydroxybutyryl-CoA. Such an enzyme can also be referred to as an oxidoreductase that converts acetoacetyl-CoA to 3-hydroxybutyryl-CoA. Such a 3-hydroxybutyryl-CoA dehydrogenase can be classified as a reaction class 1.1.1.a, oxidoreductase, where the first three digits correspond to the first three Enzyme Commission number digits which denote the general type of transformation independent of substrate specificity. An exemplary enzymatic conversion by a 3-hydroxybutyryl-CoA dehydrogenase of the invention includes, but is not limited to, the conversion of acetoacetyl-CoA to 3-hydroxybutyryl-CoA (3HB-CoA) (see FIG. 1). A 3-hydroxybutyryl-CoA dehydrogenase of the invention can be used to produce desired products such as 3HB-CoA, 3-hydroxybutyraldehyde (3-HBal), 1,3-butanediol (1,3-BDO), or other desired products such as a downstream product, including an ester or amide thereof, in a cell, such as a microbial organism, containing a suitable metabolic pathway, or in vitro. For example, 1,3-BDO can be reacted with an acid, either in vivo or in vitro, to convert to an ester using, for example, a lipase. Such esters can have nutraceutical, medical and food uses, and are advantaged when the R-form of 1,3-butanediol is used since that is the form (compared to S-form or the racemic mixture that is made from petroleum or from ethanol by the acetaldehyde chemical synthesis route) best utilized by both animals and humans as an energy source (e.g. a ketone ester, such as (R)-3-hydroxybutyl-R-1,3-butanediol monoester (which has GRAS approval in the United States) and (R)-3-hydroxybutyrate glycerol monoester or diester). The ketone esters can be delivered orally, and the ester releases R-1,3-butanediol that is used by the body. See for example U.S. Patent Application US20150164855 entitled "Ketone Bodies and Ketone Body Esters for Maintaining or Improving Muscle Power Output." Thus, in some embodiments, the present invention is particularly useful to provide an improved enzymatic route and microorganism to provide an improved composition of 1,3-butanediol, namely R-1,3-butanediol (R-1,3-BDO), highly enriched or essentially enantiomerically pure, and further having improved purity qualities with respect to by-products. In some embodiment, the 1,3-butanediol is about or at least about 10%, 25%, 50%, 75%, 80%, 85%, 90%, 95%, 96%, 97%, 98%, 99%, or 100% R-1,3-butanediol (R-1,3-BDO).

1,3-Butanediol, also referred to as butylene glycol, has further food related uses including use directly as a food source, a food ingredient, a flavoring agent, a solvent or solubilizer for flavoring agents, a stabilizer, an emulsifier, and an anti-microbial agent and preservative. 1,3-Butanediol is used in the pharmaceutical industry as a parenteral drug solvent. 1,3-Butanediol finds use in cosmetics as an ingredient that is an emollient, a humectant, to prevent crystallization of insoluble ingredients, a solubilizer for less-water-soluble ingredients such as fragrances, and as an anti-microbial agent and preservative. For example, it can be used as a humectant, especially in hair sprays and setting lotions; it reduces loss of aromas from essential oils, preserves against spoilage by microorganisms, and is used as a solvent for benzoates. 1,3-Butanediol can be use at concentrations from 0.1 percent or less to 50 percent or greater. It is used in hair and bath products, eye and facial makeup, fragrances, personal cleanliness products, and shaving and skin care preparations. See for example the Cosmetic Ingredient Review board's report: "Final Report on the Safety Assessment of Butylene Glycol, Hexylene Glycol, Ethoxy diglycol, and Dipropylene Glycol", Journal of the American College of Toxicology, Volume 4, Number 5, 1985. This report, which is incorporated by reference, provides specific uses and concentrations of 1,3-butanediol (butylene glycol) in cosmetics; see for examples the report's Table 2 therein entitled "Product Formulation Data".

In some embodiments, the invention provides a thiolase, such as a thiolase having at least 50%, 65%, 70%, 75%, 80%, 85%, 90%, 95%, 98% 99%, or 100% sequence identity to SEQ ID NO: 4. In some embodiments, the thiolase has at least 90% sequence identity to SEQ ID NO: 4. In some embodiments, the thiolase has the sequence of SEQ ID NO: 4. In some embodiments, the thiolase exhibits a reduced oxygen sensitivity in converting two acetyl-CoA molecules to acetoacetyl-CoA as compared to a thiolase having the amino acid sequence of SEQ ID NO: 6. In some embodiments, the thiolase is an isolated polypeptide. In some embodiments, the thiolase is in a composition, such as a reaction mixture, cell, or cell culture. In some embodiments, the composition comprising the thiolase comprises a a variant 3-hydroxybutyryl-CoA dehydrogenase, examples of which are described herein.

In some embodiments, the invention provides a variant 3-hydroxybutyryl-CoA dehydrogenase having an increased ability to utilize NADH as a cofactor in a reaction converting acetoacetyl-CoA to 3-hydroxybutyryl-CoA, relative to a reference 3-hydroxybutyryl-CoA dehydrogenase consisting of amino acid sequence SEQ ID NO: 2. In some embodiments, the increase in ability to utilize NADH is an increase of at least about 5%, 10%, 15%, 25%, 50%, 100%, or more. In some embodiments, the ability of the variant to utilize NADH is at least about 1.5-fold, 2-fold, 3-fold, 4-fold, 5-fold, 6-fold, 7-fold, 8-fold, 9-fold, 10-fold, 15-fold, or 20-fold greater than that of the reference enzyme. In some embodiments, the ability of the variant to utilize NADH is at least about 5-fold greater than that of the reference enzyme. Any suitable assay for measuring NADH utilization, as determined by one skilled in the art, can be used. Non-limiting examples of assays for making such measurements are described herein. In one example, enzyme activity when using NADH as a cofactor as compared to when using NADPH is measured and compared as a ratio of NADH-based activity to NADPH-based activity. In such a case, increased NADH utilization is indicated by an increase in the ratio of NADH-based enzyme activity to NADPH-based enzyme activity, a measure that is also referred to as the enzyme's specificity for NADH over NADPH.

In some embodiments, the invention provides a variant 3-hydroxybutyryl-CoA dehydrogenase the presence of which increases 1,3-BDO production in a 1,3-BDO-producing cell, relative to a reference 3-hydroxybutyryl-CoA dehydrogenase consisting of amino acid sequence SEQ ID NO: 2. In some embodiments, the increase in 1,3-BDO production is an increase of at least about 5%, 10%, 15%, 25%, 50%, 100%, or more. In some embodiments, the increased 1,3-BDO production is an increase of at least about 1.5-fold, 2-fold, 3-fold, 4-fold, 5-fold, 6-fold, 7-fold, 8-fold, 9-fold, 10-fold, 15-fold, or 20-fold. In some embodiments, the increased 1,3-BDO production is at least about 5-fold. Any suitable assay for measuring 1,3-BDO production, as determined by one skilled in the art, can be used. Non-limiting examples of assays for making such measurements are described herein. In some embodiments, the increased 1,3-BDO production is an increase under anaerobic or substantially anaerobic conditions.

In some aspects, the present disclosure provides isolated polypeptide variants, such as variants of a reference polypeptide. In some embodiments, the reference polypeptide has an amino acid sequence of SEQ ID NO: 2, and the polypeptide variant is selected from Table 1 and has one or more amino acid substitutions relative to SEQ ID NO: 2. In some embodiments, the polypeptide variant comprises a sequence having at least 50% identity to SEQ ID NO: 2 or to a variant selected from Table 1; and the polypeptide variant comprises an amino acid substitution corresponding to one or more positions of SEQ ID NO: 2 selected from C34, G35, P36, N37, S38, and R40. In some embodiments, (i) the amino acid corresponding to C34 is replaced with A, D, E, H, I, L, M, S, T, V, or Y; (ii) the amino acid corresponding to G35 is replaced with C, D, E, F, H, I, K, L, M, P, Q, R, S, T, V, or Y; (iii) the amino acid corresponding to P36 is replaced with S; (iv) the amino acid corresponding to N37 is replaced with K; (v) the amino acid corresponding to S38 is replaced with A, C, D, E, F, G, H, I, K, L, M, Q, T, V, W, or Y; (vi) the amino acid corresponding to R40 is replaced with A, D, E, F, G, H, I, K, L, M, N, P, Q, S, T, V, or Y; or (vii) two or more of (i)-(vi) in any combination. In some embodiments, the polypeptide variant comprises a sequence having at least 50% identity to SEQ ID NO: 2 or a variant selected from Table 1; and the polypeptide variant comprises 1, 2, 3, 4, 5, or more amino acid substitutions relative to SEQ ID NO: 2 selected from: A103M, A107V, A156S, A158R, A193R, A204T, C20F, C34A, C34D, C34E, C34H, C34I, C34L, C34M, C34S, C34T, C34V, C34Y, D104A, D104E, D104Q, D106H, D129E, D236C, D236V, E215H, E215W, E42Q, E46C, E46S, E78K, F55I, G241G, G35*, G35A, G35C, G35D, G35E, G35F, G35H, G35I, G35K, G35L, G35M, G35P, G35Q, G35R, G35S, G35T, G35V, G35Y, G90V, K209Q, L160A, L160M, L167Q, L213N, L243A, L243I, L243V, N112C, N112D, N112H, N37K, P207Q, P36S, Q144Q, Q47L, Q47L, Q48Q, R40A, R40D, R40E, R40F, R40G, R40H, R40I, R40K, R40L, R40M, R40N, R40P, R40Q, R40S, R40T, R40V, R40Y, R41H, R98C, S115R, S38A, S38C, S38D, S38E, S38F, S38G, S38H, S38I, S38K, S38L, S38M, S38Q, S38T, S38V, S38W, S38Y, T114C, T155C, T173S, T205N, T205Q, T92H, T92N, V203I, and V31I. In some embodiments, the polypeptide variant comprises a sequence having at least 80%, 90%, 95%, or 99% sequence identity to SEQ ID NO: 2 or a variant selected from Table 1.

In some embodiments, the isolated polypeptide variant is a variant of a first reference polypeptide, wherein (a) the first reference polypeptide has an amino acid sequence of SEQ ID NO: 2, (b) the polypeptide variant comprises one or more amino acid substitutions relative to SEQ ID NO: 2, (c) the one or more amino acid substitutions are selected from Table 1, and (d) the polypeptide variant has at least 65%, 70%, 75%, 80%, 85%, 90%, 95%, 98%, or 99% sequence identity to a corresponding variant selected from Table 1. In some embodiments, the polypeptide variant has at least 80%, 90%, or 95% sequence identity to the corresponding variant selected from Table 1. In some embodiments, the polypeptide variant further comprises a conservative amino acid substitution in from 1 to 100 modified amino acid positions relative to the corresponding first reference polypeptide, wherein said modified positions are other than the one or more amino acid substitutions of a second reference polypeptide.

In some embodiments, polypeptide variants disclosed herein have one or more additional characteristics. In some embodiments, the one or more amino acid substitutions comprise at least 2, 3, 4, 5, 6, 7, 8, 9, or 10 amino acid substitutions selected from Table 1. In some embodiments, the polypeptide variant comprises no modification at from 2 to 300 unmodified amino acid positions compared to the first reference polypeptide, wherein said unmodified positions are selected from those that are identical to between 2, 3, 4, or 5 amino acid sequences referenced in Table 2. In some embodiments, the polypeptide can convert acetoacetyl-CoA to 3-hydroxybutyryl-CoA. In some embodiments, the isolated polypeptide variant is a 3-hydroxybutyryl-CoA dehydrogenase having an increased ability to utilize NADH as a cofactor in a reaction converting acetoacetyl-CoA to 3-hydroxybutyryl-CoA, relative to a reference 3-hydroxybutyryl-CoA dehydrogenase encoded by SEQ ID NO: 2.

In some aspects, the invention also provides nucleic acids, such as nucleic acids encoding a 3-hydroxybutyryl-CoA dehydrogenase polypeptide and/or a thiolase of the invention, and isolated nucleic acid molecules disclosed herein. An isolated nucleic acid molecule, such as a nucleic acid molecule encoding a 3-hydroxybutyryl-CoA dehydrogenase and/or a thiolase, can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or to a nucleic acid molecule that encodes an amino acid sequence disclosed herein by SEQ ID NO, GenBank and/or GI number. For example, the nucleic acid molecule can have at least 50%, 65%, 70%, 75%, 80%, 85%, 90%, 91%, 92%, 93%, 94%, 95%, 96%, 97%, 98% or 99% sequence identity, or be identical, to a nucleic acid described herein.

Stringent hybridization refers to conditions under which hybridized polynucleotides are stable. As known to those of skill in the art, the stability of hybridized polynucleotides is reflected in the melting temperature (Tm) of the hybrids. In general, the stability of hybridized polynucleotides is a function of the salt concentration, for example, the sodium ion concentration, and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5×Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamine tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

A nucleic acid molecule encoding a 3-hydroxybutyryl-CoA dehydrogenase and/or a thiolase of the invention can have at least a certain sequence identity to a nucleotide sequence disclosed herein. Accordingly, in some aspects of the invention, a nucleic acid molecule encoding a 3-hydroxybutyryl-CoA dehydrogenase and/or a thiolase of the invention has a nucleotide sequence of at least 50% identity, 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity, or is identical, to a nucleic acid disclosed herein by SEQ ID NO, GenBank and/or GI number or to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore, Md. (1999). Preferably, default parameters are used for the alignment. One alignment program well known in the art that can be used is BLAST set to default parameters. In particular, the align program can be BLASTN or BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information (see also Altschul et al., "*J. Mol. Biol.* 215:403-410 (1990)).

In some embodiments, the nucleic acid molecule is an isolated nucleic acid molecule. In some embodiments, the isolated nucleic acid molecule is a nucleic acid molecule encoding a variant of a reference polypeptide, wherein (i) the reference polypeptide has an amino acid sequence of SEQ ID NO: 2, (ii) the variant comprises one or more amino acid substitutions relative to SEQ ID NO: 2, and (iii) the one or more amino acid substitutions are selected from Table 1. Table 1 provides a non-limiting list of example variants of SEQ ID NO: 2. For each variant in Table 1, all positions except for the indicated position(s) are identical to SEQ ID NO: 2. Amino acid substitutions are identified by a letter indicating the identity of an amino acid of SEQ ID NO: 2, followed by a number indicating the position of that amino acid in SEQ ID NO: 2, followed by a letter identifying which amino acid is substituted for the indicated amino acid of SEQ ID NO:2. For example, "G35E" indicates that the glycine at position 35 in SEQ ID NO: 2 is replaced with a glutamic acid. The single-letter code used to identify amino acids is the standard code known by those skilled in the art. Some variants in Table 1 comprise two or more substitutions, which is indicated by a list of substitutions (e.g., "G35E, R40A"). The one or more amino acid substitutions can be selected from any one of the variants listed in Table 1, or from any combination of two or more variants listed in Table 1. When selecting from a single variant in Table 1, the resulting variant can comprise one or more of the substitutions of the selected variant in any combination, including all of the indicated substitutions or less than all of the indicated substitutions. When substitutions are selected from those of two or more variants in Table 1, the resulting variant can comprise one or more of the substitutions of the selected variants, including all of the indicated substitutions or less than all of the indicated substitutions from each of the two or more selected variants, in any combination. For example, the resulting variant can comprise 1, 2, 3, or 4 substitutions from a single variant in Table 1. As a further example, the resulting variant can comprise 1, 2, 3, 4, 5, 6, 7, 8, 9, 10, 15, 20, 25, or more substitutions selected from 1, 2, 3, 4, 5, or more selected variants of Table 1. In some embodiments, the resulting variant comprises all of the indicated substitutions of a selected variant in Table 1. In some embodiments, the resulting variant differs from SEQ ID NO: 2 by at least one amino acid substitution, but less than 25, 20, 10, 5, 4, or 3 amino acid substitutions. In some embodiments, the resulting variant differs from SEQ ID NO: 2 by at least one amino acid substitution, but less than 5, 4, or 3 amino acid substitutions. In some embodiments, the resulting variant comprises, consists essentially of, or consists of a sequence as indicated by a variant selected from Table 1, differing from SEQ ID NO: 2 only at the indicated amino acid substitutions.

In some embodiments, the nucleic acid molecule is an isolated nucleic acid molecule encoding a variant of a reference polypeptide (the reference polypeptide having an amino acid sequence of SEQ ID NO: 2), wherein the variant (i) comprises one or more amino acid substitutions of a corresponding variant selected from Table 1, and (ii) has at least 50%, 65%, 70%, 75%, 80%, 85%, 90%, 95%, 98% 99%, or 100% sequence identity to the corresponding variant. In cases where the second variant has 100% sequence identity to the corresponding variant, the second variant comprises a sequence as indicated by a variant selected from Table 1, and may or may not have one or more additional amino acids at either or both the amino- and carboxy-termini. In some embodiments, the resulting variant has at least 80%, 85%, 90%, or 95% sequence identity to a corresponding variant selected from Table 1; in some cases, identity is at least 90% or more. In cases where the resulting variant is less than 100% identical to a corresponding variant selected from Table 1, the position of one or more of the amino acid substitutions indicated for the corresponding variant may shift (e.g. in the case of insertion or deletion of one or more amino acids), but still be contained within the resulting variant. For example, the glutamic acid substitution corresponding to "G35E" (at position 35 relative to SEQ ID NO: 2) may be present, but at a different position (and possibly represent a change from a different starting amino acid) in the resulting variant. Whether an amino acid corresponds to an indicated substitution, albeit at a different position, can be determined by sequence alignment. In general, an alignment showing identity or similarity of one or more amino acids flanking the amino acid substitution will allow the variant amino acid in a homologous query sequence to be positioned locally with respect to the corresponding variant of Table 1 to confirm the presence of the substitution, albeit at a shifted numerical position in a given polypeptide chain. In some embodiments, a region comprising at least three to fifteen amino acids, including the substituted position, will locally align with the corresponding variant sequence with a relatively high percent identity or similarity, including at the position of the substituted amino acid along the corresponding variant sequence (e.g. 90%, 95%, or 100% identity). In some embodiments, the one or more amino acid substitutions (e.g. all or less than all of the amino acid substitutions) indicated by a corresponding variant selected from Table 1 is considered to be present in a given variant, even if occurring at a different physical position along a polypeptide chain, if the sequence of the polypeptide being compared aligns to the corresponding variant with an identical amino acid at the indicated position along the corresponding variant sequence when using a BLASTP alignment algorithm with default parameters. Alignments can also be used to identify a position in a starting sequence that should be modified in order to arrive at a polypeptide corresponding to a variant polypeptide disclosed herein (e.g. as in Table 1), including in cases where the position and/or identity of the starting amino acid to be modified is different from that of the corresponding variant. For example, in the case of a variant comprising an R40A substitution, arginine at position 40 of SEQ ID NO: 2 may align to a tyrosine at position 29 (Y29) of a query sequence, indicating that a Y29A substitution in the query sequence corresponds to R40A of the corresponding variant. In general, two amino acids are considered to be similar if having chemical properties sufficiently similar for contributing to an alignment using default parameters.

In some embodiments, a nucleic acid molecule of the invention is complementary to a nucleic acid described in connection with any of the various embodiments herein.

It is understood that a nucleic acid of the invention or a polypeptide of the invention can exclude a wild type parental sequence, for example a parental sequence as disclosed in Table 2. One skilled in the art will readily understand the meaning of a parental wild type sequence based on what is well known in the art. It is further understood that such a nucleic acid of the invention can exclude a nucleic acid sequence encoding a naturally occurring amino acid sequence as found in nature. Similarly, a polypeptide of the invention can exclude an amino acid sequence as found in nature. Thus, in a particular embodiment, the nucleic acid or polypeptide of the invention is as set forth herein, with the proviso that the encoded amino acid sequence is not the wild type parental sequence or a naturally occurring amino acid sequence and/or that the nucleic acid sequence is not a wild type or naturally occurring nucleic acid sequence. A naturally occurring amino acid or nucleic acid sequence is understood by those skilled in the art as relating to a sequence that is found in a naturally occurring organism as found in nature. Thus, a nucleic acid or amino acid sequence that is not found in the same state or having the same nucleotide or encoded amino acid sequence as in a naturally occurring organism is included within the meaning of a nucleic acid and/or amino acid sequence of the invention. For example, a nucleic acid or amino acid sequence that has been altered at one or more nucleotide or amino acid positions from a parent sequence, including variants as described herein, are included within the meaning of a nucleic acid or amino acid sequence of the invention that is not naturally occurring. An isolated nucleic acid molecule of the invention excludes a naturally occurring chromosome that contains the nucleic acid sequence, and can further exclude other molecules as found in a naturally occurring cell such as DNA binding proteins, for example, proteins such as histones that bind to chromosomes within a eukaryotic cell.

Thus, an isolated nucleic acid sequence of the invention has physical and chemical differences compared to a naturally occurring nucleic acid sequence. An isolated or non-naturally occurring nucleic acid of the invention does not contain or does not necessarily have some or all of the chemical bonds, either covalent or non-covalent bonds, of a naturally occurring nucleic acid sequence as found in nature. An isolated nucleic acid of the invention thus differs from a naturally occurring nucleic acid, for example, by having a different chemical structure than a naturally occurring nucleic acid sequence as found in a chromosome. A different chemical structure can occur, for example, by cleavage of phosphodiester bonds that release an isolated nucleic acid sequence from a naturally occurring chromosome. An isolated nucleic acid of the invention can also differ from a naturally occurring nucleic acid by isolating or separating the nucleic acid from proteins that bind to chromosomal DNA in either prokaryotic or eukaryotic cells, thereby differing from a naturally occurring nucleic acid by different non-covalent bonds. With respect to nucleic acids of prokaryotic origin, a non-naturally occurring nucleic acid of the invention does not necessarily have some or all of the naturally occurring chemical bonds of a chromosome, for example, binding to DNA binding proteins such as polymerases or chromosome structural proteins, or is not in a higher order structure such as being supercoiled. With respect to nucleic acids of eukaryotic origin, a non-naturally occurring nucleic acid of the invention also does not necessarily contain the same internal nucleic acid chemical bonds or chemical bonds with structural proteins as found in chromatin, for example, bonding to histones or scaffold proteins, or is not contained in a centromere or telomere. Thus, the non-naturally occurring nucleic acids of the invention are chemically distinct from a naturally occurring nucleic acid because they either lack or contain different van der Waals interactions, hydrogen bonds, ionic or electrostatic bonds, and/or covalent bonds from a nucleic acid as found in nature. Such differences in bonds can occur either internally within separate regions of the nucleic acid (that is, in cis) or such difference in bonds can occur in trans, for example, interactions with chromosomal proteins. In the case of a nucleic acid of eukaryotic origin, a cDNA is considered to be an isolated or non-naturally occurring nucleic acid since the chemical bonds within a cDNA differ from the covalent bonds, that is the sequence, of a gene on chromosomal DNA. Thus, it is understood by those skilled in the art that an isolated or non-naturally occurring nucleic acid is distinct from a naturally occurring nucleic acid.

In some embodiments, the invention provides an isolated polypeptide having an amino acid sequence disclosed herein, such as those referenced in Table 1, wherein the amino acid sequence includes one or more variant amino acid positions relative to SEQ ID NO: 2. In particular, such a polypeptide encodes a 3-hydroxybutyryl-CoA dehydrogenase, which can convert acetoacetyl-CoA to 3-hydroxybutyryl-CoA. In some aspects, the isolated polypeptide of the invention includes an amino acid sequence, other than the one or more variant amino acid positions as set forth in Table 1, with at least 50%, 65%, 70%, 75%, 80%, 85%, 90%, 91%, 92%, 93%, 94%, 95%, 96%, 97%, 98% or 99% sequence identity, or is identical, to an amino acids sequence referenced in Table 1. It is understood that a variant amino acid position can include any one of the 20 naturally occurring amino acids, a conservative substitution of a wild type or parental sequence at the corresponding position of the variant amino acid position, or a specific amino acid at the variant amino acid position such as those disclosed herein in Table 1. It is further understood that any of the variant amino acid positions can be combined to generate further variants, such as variants encoded by an isolated nucleic acid described herein. Variants with combinations of two or more variant amino acid positions exhibited activities greater than wild type. Thus, as exemplified herein, generating enzyme variants by combining active variant amino acid positions resulted in enzyme variants with improved properties. One skilled in the art can readily generate polypeptides with single variant positions or combinations of variant positions using methods well known to those skilled in the art to generate polypeptides with desired properties, including increased activity, increased utilization of or specificity for NADH, decreased byproduct formation, such as ethanol, increased kcat, and the like, as described herein.

"Homology" or "identity" or "similarity" refers to sequence similarity between two polypeptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology between sequences is a function of the number of matching positions shared by the sequences. A polypeptide or polypeptide region (or a polynucleotide or polynucleotide region) has a certain percentage (for example, 50%, 65%, 70%, 75%, 80%, 85%, 90%, 95%, 98% or 99%) of "sequence identity" to another sequence means that, when aligned, that percentage of amino acids (or nucleotide bases) are the same in comparing the two sequences.

In certain embodiments, the invention provides an isolated polypeptide having an amino acid sequence that includes at least two, three, four, five, six, seven, eight, nine, ten, eleven, twelve, thirteen, fourteen, fifteen, sixteen, seventeen, eighteen, nineteen, twenty or more substitutions in any combination disclosed herein. In some embodiments, the isolated polypeptide is a variant of a reference polypeptide, wherein the reference polypeptide has an amino acid sequence of SEQ ID NO: 2, and the polypeptide variant is selected from Table 1 and has one or more amino acid substitutions relative to SEQ ID NO: 2.

In some embodiments, the isolated polypeptide is a variant of a reference polypeptide, wherein the reference polypeptide has an amino acid sequence of SEQ ID NO: 2, the polypeptide variant comprises one or more amino acid substitutions relative to SEQ ID NO: 2, the one or more amino acid substitutions are selected from Table 1, and the polypeptide variant has at least 50%, 65%, 70%, 75%, 80%, 85%, 90%, 95%, 98%, or 99% sequence identity to a corresponding variant selected from Table 1. The one or more amino acid substitutions can be selected from any one of the variants listed in Table 1, or from any combination of two or more variants listed in Table 1. When selecting from a single variant in Table 1, the resulting variant can comprise one or more of the substitutions of the selected variant in any combination, including all of the indicated substitutions or less than all of the indicated substitutions. When substitutions are selected from those of two or more variants in Table 1, the resulting variant can comprise one or more of the substitutions of the selected variants, including all of the indicated substitutions or less than all of the indicated substitutions from each of the two or more selected variants, in any combination. For example, the resulting variant can comprise 1, 2, 3, or 4 substitutions from a single variant in Table 1. As a further example, the resulting variant can comprise 1, 2, 3, 4, 5, 6, 7, 8, 9, 10, 15, 20, 25, or more substitutions selected from 1, 2, 3, 4, 5, or more selected variants of Table 1. In some embodiments, the resulting variant comprises all of the indicated substitutions of a selected variant in Table 1. In some embodiments, the resulting variant differs from SEQ ID NO: 2 by at least one amino acid substitution, but less than 25, 20, 10, 5, 4, or 3 amino acid substitutions. In some embodiments, the resulting variant differs from SEQ ID NO: 2 by at least one amino acid substitution, but less than 5, 4, or 3 amino acid substitutions. In some embodiments, the resulting variant comprises, consists essentially of, or consists of a sequence as indicated by a variant selected from Table 1, differing from SEQ ID NO: 2 only at the indicated amino acid substitutions.

In some embodiments, the resulting variant has at least 80%, 85%, 90%, or 95% sequence identity to a corresponding variant selected from Table 1; in some cases, identity is at least 90% or more. In cases where the resulting variant is less than 100% identical to a corresponding variant selected from Table 1, the position of one or more of the amino acid substitutions indicated for the corresponding variant may shift (e.g. in the case of insertion or deletion of one or more amino acids), but still be contained within the resulting variant. For example, the glutamic acid substitution corresponding to "G35E" (at position 35 relative to SEQ ID NO: 2) may be present, but at a different position (and possibly represent a change from a different starting amino acid) in the resulting variant. Whether an amino acid corresponds to an indicated substitution, albeit at a different position, can be determined by sequence alignment, as described above. In some embodiments, the one or more amino acid substitutions (e.g. all or less than all of the amino acid substitutions) indicated by a corresponding variant selected from Table 1 is considered to be present in a given variant, even if occurring at a different physical position along a polypeptide chain, if the sequence of the polypeptide being compared aligns to the corresponding variant with an identical amino acid at the indicated position along the corresponding variant sequence when using a BLASTP alignment algorithm with default parameters.

Amino acid substitutions in a polypeptide variant, alone or in combination, can produce an enzyme that retains or improves the activity relative to a reference polypeptide, e.g. the wild-type (native) enzyme. In some aspects, the polypeptide of the invention having any combination of variants set forth in Table 1 can convert acetoacetyl-CoA to 3-hydroxybutyryl-CoA. Methods of generating and assaying such polypeptides are well known to one of skill in the art. In some embodiments, the polypeptide variant has an increased ability to utilize NADH, and/or increases 1,3-BDO production in a 1,3-BDO producing cell, relative to a polypeptide consisting of amino acid sequence SEQ ID NO: 2.

In some embodiments, an isolated polypeptide of the invention (e.g., a thiolase or a 3-hydroxybutyryl-CoA dehydrogenase) includes a conservative amino acid substitution in from 1 to 100 amino acid positions, or alternatively from 2 to 100 amino acid positions, or alternatively from 3 to 100 amino acid positions, or alternatively from 4 to 100 amino acid positions, or alternatively from 5 to 100 amino acid positions, or alternatively from 6 to 100 amino acid positions, or alternatively from 7 to 100 amino acid positions, or alternatively from 8 to 100 amino acid positions, or alternatively from 9 to 100 amino acid positions, or alternatively from 10 to 100 amino acid positions, or alternatively from 15 to 100 amino acid positions, or alternatively from 20 to 100 amino acid positions, or alternatively from 30 to 100 amino acid positions, or alternatively from 40 to 100 amino acid positions, or alternatively from 50 to 100 amino acid positions, or any integer therein. In some embodiments, conservative amino acid substitution positions in a 3-hydroxybutyryl-CoA dehydrogenase are other than the variant amino acid positions set forth in Table 1. In some aspects, the conservative amino acid sequence is a chemically conservative or an evolutionary conservative amino acid substitution. Methods of identifying conservative amino acids are well known to one of skill in the art, any one of which can be used to generate the isolated polypeptides of the invention.

In some embodiments, an isolated polypeptide of the invention (e.g., a thiolase or a 3-hydroxybutyryl-CoA dehydrogenase) can include no modification at from 2 to 300 amino acid positions, or alternatively 3 to 300 amino acid positions, or alternatively 4 to 300 amino acid positions, or alternatively 5 to 300 amino acid positions, or alternatively 10 to 300 amino acid positions, or alternatively 20 to 300 amino acid positions, or alternatively 30 to 300 amino acid positions, or alternatively 40 to 300 amino acid positions, or alternatively 50 to 300 amino acid positions, or alternatively 60 to 300 amino acid positions, or alternatively 80 to 300 amino acid positions, or alternatively 100 to 300 amino acid positions, or alternatively 150 to 300 amino acid positions, or alternatively 200 to 300 amino acid positions, or alternatively 250 to 300 amino acid positions, or any integer therein, compared to the parent (wild-type) sequence. In some embodiments, the unmodified positions in a 3-hydroxybutyryl-CoA dehydrogenase are selected from those that are identical to between 2, 3, 4, or 5 of the amino acid sequences referenced in Table 2.

It is understood that the variant polypeptides such as polypeptide variants of 3-hydroxybutyryl-CoA dehydrogenase, as disclosed herein, can carry out a similar enzymatic reaction as the parent polypeptide, for example, converting acetoacetyl-CoA to 3-hydroxybutyryl-CoA. It is further understood that the polypeptide variants of the 3-hydroxybutyryl-CoA dehydrogenase enzyme can include variants that provide a beneficial characteristic to the polypeptide, including but not limited to, increased activity, increased utilization of or specificity for NADH, increased kcat, and the like. In a particular embodiment, the 3-hydroxybutyryl-CoA dehydrogenase variant can exhibit an activity that is at least the same or higher than a wild type or parent polypeptide, that is, is higher than a reference polypeptide, such as a parent polypeptide without the variant amino acid position or a polypeptide consisting of SEQ ID NO: 2. For example, the 3-hydroxybutyryl-CoA dehydrogenase variants of the invention can have 1.2, 1.5, 2, 2.5, 3, 3.5, 4, 4.5, 5, 5.5, 6, 6.5, 7, 7.5, 8, 8.5, 9, 9.5, 10, or even higher fold activity, relative to a wild type or parent polypeptide. In some embodiments, the 3-hydroxybutyryl-CoA dehydrogenase variant can impart to a bacterium comprising the variant decreased byproduct formation (such as ethanol), as compared to a bacterium comprising a polypeptide consisting of SEQ ID NO: 2 instead of the variant polypeptide. Such a 3-hydroxybutyryl-CoA dehydrogenase variant can exhibit an activity that has decreased byproduct formation relative to a reference polypeptide, such as wild type or a parent polypeptide, that is, a parent polypeptide without the variant amino acid position, or a polypeptide consisting of SEQ ID NO: 2. In another particular embodiment, the 3-hydroxybutyryl-CoA dehydrogenase variant can exhibit increased kcat, for example, 1.2, 1.5, 2, 2.5, 3, 3.5, 4, 4.5, 5, 5.5, 6, 6.5, 7, 7.5, 8, 8.5, 9, 9.5, 10, or even higher fold kcat, relative to a wild type or parent polypeptide. Such a 3-hydroxybutyryl-CoA dehydrogenase variant can exhibit an activity that has increased kcat relative to a reference polypeptide, such as a wild type or a parent polypeptide, that is, a parent polypeptide without the variant amino acid position, or a polypeptide consisting of SEQ ID NO: 2. In some embodiments, the 3-hydroxybutyryl-CoA dehydrogenase variants of the invention have increased utilization of or specificity for NADH. For example, the 3-hydroxybutyryl-CoA dehydrogenase variants of the invention can have 1.2, 1.5, 2, 2.5, 3, 3.5, 4, 4.5, 5, 5.5, 6, 6.5, 7, 7.5, 8, 8.5, 9, 9.5, 10, or even higher fold utilization of or specificity for NADH, relative to a wild type or parent polypeptide.

It is understood that, in certain embodiments, a 3-hydroxybutyryl-CoA dehydrogenase variant can exhibit two or more of the characteristics described above, for example, two or more of the characteristics of (1) increased activity, (2) increased utilization of or specificity for NADH, (3) increased kcat, and the like, in any combination. Such combinations include, for example, characteristics 1 and 2; 1 and 3; 2 and 3; and 1, 2 and 3.

The polypeptides of the invention can be isolated by a variety of methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology*, Vol. 182, (Academic Press, (1990)). Alternatively, the isolated polypeptides of the present invention can be obtained using well-known recombinant methods (see, for example, Sambrook et al., supra, 2001; Ausubel et al., supra, 1999). The methods and conditions for biochemical purification of a polypeptide of the invention can be chosen by those skilled in the art, and purification monitored, for example, by a functional assay.

One non-limiting example of a method for preparing a polypeptide of the invention is to express nucleic acids encoding the polypeptide in a suitable host cell, such as a bacterial cell, a yeast cell, fungal cell, or other suitable cell, using methods well known in the art, and recovering the expressed polypeptide, again using well-known purification methods, as described herein. Polypeptides can be isolated directly from cells that have been transformed with expression vectors as described herein. Recombinantly expressed polypeptides can also be expressed as fusion proteins with appropriate affinity tags, such as glutathione S transferase (GST), poly His, streptavidin, and the like, and affinity purified, if desired. A polypeptide can retain the affinity tag, if desired, or optionally the affinity tag can be removed from the polypeptide using well known methods to remove an affinity tag, for example, using appropriate enzymatic or chemical cleavage. Thus, the invention provides polypeptides of the invention without or optionally with an affinity tag. In some embodiments, the invention provides a host cell expressing a polypeptide of the invention disclosed herein. An invention polypeptide can also be produced by chemical synthesis using a method of polypeptide synthesis well know to one of skill in the art (Merrifield, *J. Am. Chem. Soc.* 85:2149 (1964); Bodansky, M., *Principles of Peptide Synthesis* (Springer-Verlag, 1984); Houghten, *Proc. Natl. Acad. Sci., USA* 82:5131 (1985); Grant *Synthetic Peptides: A User Guide*. W. H. Freeman and Co., N.Y. (1992); Bodansky M and Trost B., Ed. *Principles of Peptide Synthesis*. Springer-Verlag Inc., N.Y. (1993)).

In some embodiments, the invention provides using a polypeptide disclosed herein as a biocatalyst. A "biocatalyst," as used herein, refers to a biological substance that initiates or modifies the rate of a chemical reaction. A biocatalyst can be an enzyme. A polypeptide of the invention can be used to increase the rate of conversion of a substrate to a product as disclosed herein. In the context of an industrial reaction, a polypeptide of the invention can be used, absent a host cell expressing the polypeptide, to improve reactions generating acetoacetyl-CoA, 3-HB-CoA, 3-HBal, 3-HB, or 1,3-BDO, or a downstream product related thereto such as an ester or amide thereof, for example, using in vitro methods.

In some embodiments of the invention, the polypeptide (e.g., a polypeptide encodinig a thiolase or a 3-hydroxybutyryl-CoA dehydrogenase of the invention) is provided as a cell lysate of a cell expressing the thiolase and/or the 3-hydroxybutyryl-CoA dehydrogenase. In such a case, the cell lysate serves as a source of the thiolase and/or 3-hydroxybutyryl-CoA dehydrogenase for carrying out one or more conversion reactions (e.g. conversion of two acetyl-CoA molecules to acetoacetyl-CoA, and/or conversion of acetoacetyl-CoA to 3-hydroxybutyryl-CoA), or the reverse reaction(s), in an in vitro reaction. In another embodiment, the thiolase and/or 3-hydroxybutyryl-CoA dehydrogenase can be provided in a partially purified form, for example, partially purified from a cell lysate. In another embodiment, the thiolase and/or 3-hydroxybutyryl-CoA dehydrogenase can be provided in substantially purified form, in which the thiolase and/or 3-hydroxybutyryl-CoA dehydrogenase is substantially purified from other components, such as the components of a cell extract. Methods for partially purifying or substantially purifying polypeptides are well known in the art, as described herein. In some embodiments, the thiolase and/or 3-hydroxybutyryl-CoA dehydrogenase is immobilized to a solid support, for example, a bead, plate or membrane. In a particular embodiment, the thiolase and/or 3-hydroxybutyryl-CoA dehydrogenase comprises an affinity tag, and the affinity tag is used to immobilize the 3-hydroxybutyryl-CoA dehydrogenase to a solid support. Such an affinity tag can include, but is not limited to, glutathione S transferase (GST), poly His, streptavidin, and the like, as described herein.

In some embodiments, the invention provides a composition having a polypeptide disclosed herein and at least one substrate for the polypeptide. Substrate(s) for each of the polypeptides disclosed herein are described herein and are exemplified in the Figures. The polypeptide within the composition of the invention can react with a substrate under in vitro or in vivo conditions. In this context, an in vitro condition refers to a reaction in the absence of or outside of a cell of the invention. In some embodiments, the substrate is acetyl-CoA or acetoacetyl-CoA.

In some embodiments, the invention provides a method of constructing a host strain that can include, among other steps, introducing a vector disclosed herein into a host cell, for example, that is capable of expressing an amino acid sequence encoded by the vector or capable of fermentation. Vectors of the invention can be introduced stably or transiently into a host cell using techniques well known in the art including, but not limited to, conjugation, electroporation, chemical transformation, transduction, transfection, and ultrasound transformation. Additional methods are disclosed herein, any one of which can be used in the method of the invention.

In some embodiments, the invention provides a cell that comprises a polypeptide of the invention. Thus, in some embodiments, the invention provides a non-naturally occurring cell comprising a polynucleotide encoding a thiolase and/or a 3-hydroxybutyryl-CoA dehydrogenase described herein. Optionally, the cell can comprise a 3-HB-CoA, 3-HBal, 3-HB, or 1,3-BDO pathway, and additionally optionally include a pathway to produce a downstream product related thereto such as an ester or amide thereof. In some embodiments, the non-naturally occurring cell comprises at least one exogenous nucleic acid encoding (1) a thiolase that converts two acetyl-CoA molecules to acetoacetyl-CoA, and/or (2) a 3-hydroxybutyryl-CoA dehydrogenase that converts acetoacetyl-CoA to 3-hydroxybutyryl-CoA. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, in a particular embodiment, the invention provides a cell, in particular a non-naturally occurring cell, containing at least one exogenous nucleic acid encoding a thiolase and/or a 3-hydroxybutyryl-CoA dehydrogenase, where the thiolase and/or 3-hydroxybutyryl-CoA dehydrogenase function in an acetoacetyl-CoA, 3-hydroxybutyryl-CoA, 3-HBal, 3-HB, or 1,3-BDO pathway, such as that shown in FIG. 1.

A thiolase of the invention can be an acetoacetyl-CoA thiolase that converts two molecules of acetyl-CoA into acetoacetyl-CoA and CoA. A thiolase and/or 3-hydroxybutyryl-CoA dehydrogenase of the invention can be utilized in a pathway that includes the step of converting an acetoacetyl-CoA to 3-hydroxybutyryl-CoA. Exemplary pathways for 3-hydroxybutyryl-CoA, 3-HBal, and/or 1,3-BDO that comprise a 3-hydroxybutyryl-CoA dehydrogenase have been described, for example, in WO 2010/127319, WO 2013/036764, U.S. Pat. No. 9,017,983, US 2013/0066035, each of which is incorporated herein by reference.

Exemplary 3-hydroxybutyryl-CoA, 3-HBal, and/or 1,3-BDO pathways are shown in FIG. 1 and described in WO 2010/127319, WO 2013/036764, U.S. Pat. No. 9,017,983 and US 2013/0066035. Such a 3-hydroxybutyryl-CoA, 3-HBal, and/or 1,3-BDO pathway that comprises a 3-hydroxybutyryl-CoA dehydrogenase includes, for example, (G) acetoacetyl-CoA reductase (ketone reducing), also referred to herein as 3-hydroxybutyryl-CoA dehydrogenase; (H) 3-hydroxybutyryl-CoA reductase (aldehyde forming), also referred to herein as 3-hydroxybutyraldehyde dehydrogenase, an aldehyde dehydrogenase (ALD); and (C) 3-hydroxybutyraldehyde reductase, also referred to herein as a 1,3-BDO dehydrogenase (see FIG. 1). Acetoacetyl-CoA can be formed by converting two molecules of acetyl-CoA into one molecule of acetoacetyl-CoA employing a thiolase. Acetoacetyl-CoA thiolase converts two molecules of acetyl-CoA into one molecule each of acetoacetyl-CoA and CoA (see WO 2013/036764 and US 2013/0066035).

Figure 2:
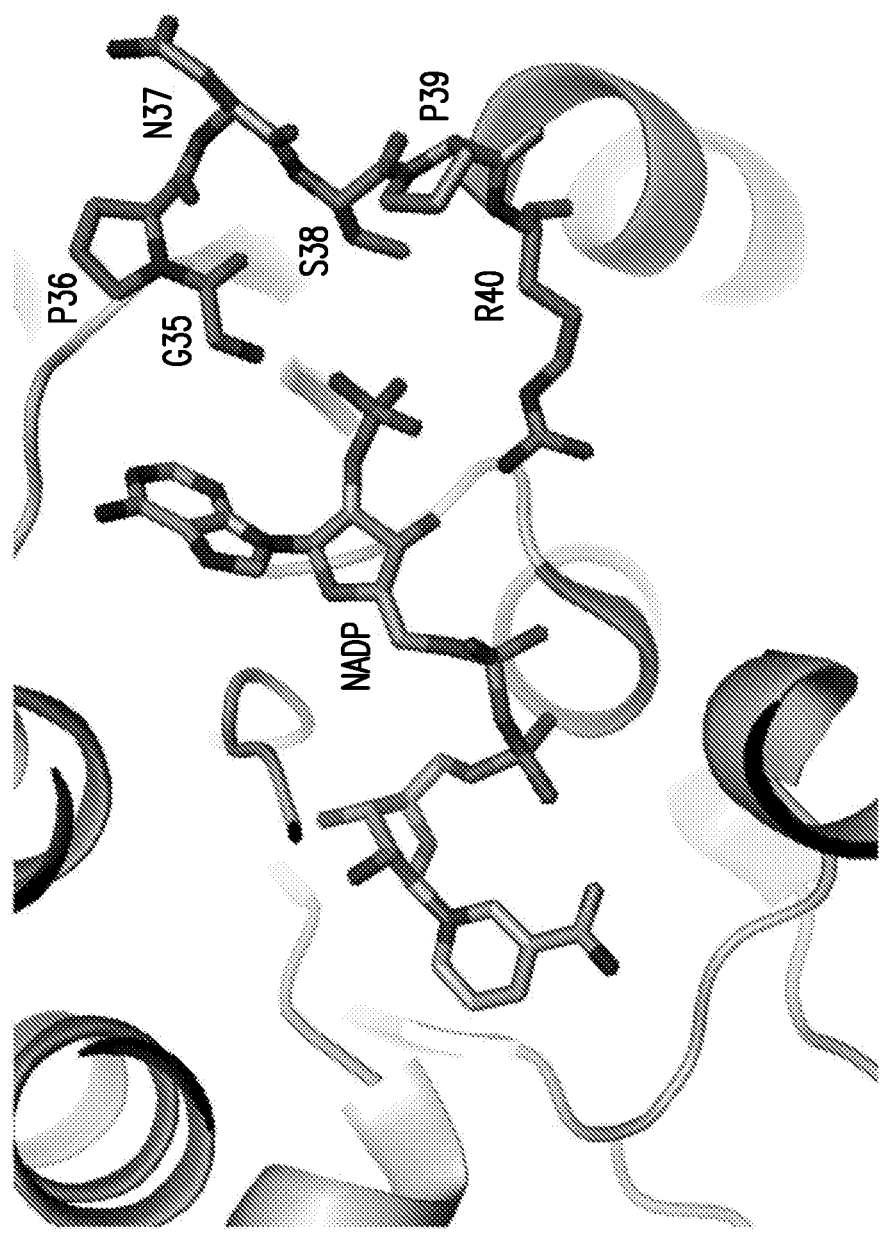
FIG. 2 illustrates a portion of an example three-dimensional crystal structure of a 3-hydroxybutyryl-CoA dehydrogenase complexed with an NADPH cofactor.

An exemplary 1,3-BDO pathway is shown in FIG. 2 of WO 2010/127319. Briefly, acetoacetyl-CoA can be converted to 3-hydroxybutyryl-CoA by acetoacetyl-CoA reductase (ketone reducing), also referred to herein as 3-hydroxybutyryl-CoA dehydrogenase (EC 1.1.1.a) (step G of FIG. 1). 3-Hydroxybutyryl-CoA can be converted to 3-hydroxybutyraldehyde by 3-hydroxybutyryl-CoA reductase (aldehyde forming) (EC 1.2.1.b), also referred to herein as 3-hydroxybutyraldehyde dehydrogenase, including an aldehyde dehydrogenase of the invention (step H of FIG. 1). 3-Hydroxybutyraldehyde can be converted to 1,3-butanediol by 3-hydroxybutyraldehyde reductase (EC 1.1.1.a), also referred to herein as 1,3-BDO dehydrogenase (step C of FIG. 1).

As disclosed herein, 3-hydroxybutyryl-CoA dehydrogenases of the invention can function in a pathway to convert acetoacetyl-CoA to 3-hydroxybutyryl-CoA. The 3-hydroxybutyryl-CoA dehydrogenases of the invention can also be used in other 3-HBal and/or 1,3-BDO pathways that comprise 3-hydroxybutyryl-CoA as a substrate/product in the pathway. One skilled in the art can readily utilize a 3-hydroxybutyryl-CoA dehydrogenase of the invention to convert acetoacetyl-CoA to 3-hydroxybutyryl-CoA in any desired pathway that comprises such a reaction.

Enzyme types required to convert common central metabolic intermediates into 1,3-BDO are indicated above with representative Enzyme Commission (EC) numbers (see also WO 2010/127319, WO 2013/036764, U.S. Pat. No. 9,017,983 and US 2013/0066035). The first three digits of each label correspond to the first three Enzyme Commission number digits which denote the general type of transformation independent of substrate specificity. Exemplary enzymes include: 1.1.1.a, Oxidoreductase (ketone to hydroxyl or aldehyde to alcohol); 1.1.1.c, Oxidoreductase (2 step, acyl-CoA to alcohol); 1.2.1.b, Oxidoreductase (acyl-CoA to aldehyde); 1.2.1.c, Oxidoreductase (2-oxo acid to acyl-CoA, decarboxylation); 1.2.1.d, Oxidoreductase (phosphorylating/dephosphorylating); 1.3.1.a, Oxidoreductase operating on CH—CH donors; 1.4.1.a, Oxidoreductase operating on amino acids (deaminating); 2.3.1.a, Acyltransferase (transferring phosphate group); 2.6.1.a, Aminotransferase; 2.7.2.a, Phosphotransferase, carboxyl group acceptor; 2.8.3.a, Coenzyme-A transferase; 3.1.2.a, Thiolester hydrolase (CoA specific); 4.1.1.a, Carboxy-lyase; 4.2.1.a, Hydro-lyase; 4.3.1.a, Ammonia-lyase; 5.3.3.a, Isomerase; 5.4.3.a, Aminomutase; 6.2.1.a, Acid-thiol ligase.

The 3-hydroxybutyryl-CoA dehydrogenases of the invention can be utilized in a cell or in vitro to convert acetoacetyl-CoA to 3-hydroxybutyryl-CoA. As disclosed herein, the 3-hydroxybutyryl-CoA dehydrogenases of the invention have beneficial and useful properties, including but not limited to increased utilization of or specificity for NADH, increased activity, decreased byproduct production, increased kcat, and the like. 3-hydroxybutyryl-CoA dehydrogenases of the invention can be used to produce the R-form of 1,3-butanediol (also referred to as (R)-1,3-butanediol), by inclusion in a process that enzymatically converts the product of an aldehyde dehydrogenase, 3-hydroxy-(R)-butyraldehyde, to (R)-1,3-butanediol using a 1,3-butanediol dehydrogenase.

The R-form of 1,3-butanediol can be utilized for production of downstream products for which the R-form is preferred. In some embodiments, the R-form can be utilized as a pharmaceutical and/or nutraceutical (see e.g., WO 2014/190251). For example, (R)-1,3-butanediol can be used to produce (3R)-hydroxybutyl (3R)-hydroxybutyrate, which can have beneficial effects such as increasing the level of ketone bodies in the blood. Increasing the level of ketone bodies can lead to various clinical benefits, including an enhancement of physical and cognitive performance and treatment of cardiovascular conditions, diabetes and treatment of mitochondrial dysfunction disorders and in treating muscle fatigue and impairment (see e.g., WO 2014/190251).

While generally described herein as a cell that contains an acetoacetyl-CoA, 3-hydroxybutyryl-CoA, 3-HBal, 3-HB, or 1,3-BDO pathway comprising a thiolase and/or a 3-hydroxybutyryl-CoA dehydrogenase of the invention, it is understood that the invention also provides a cell comprising at least one exogenous nucleic acid encoding a thiolase and/or a 3-hydroxybutyryl-CoA dehydrogenase of the invention. The thiolase and/or 3-hydroxybutyryl-CoA dehydrogenase can be expressed in a sufficient amount to produce a desired product, such as a product of an acetoacetyl-CoA, 3-hydroxybutyryl-CoA, 3-HBal, 3-HB, or 1,3-BDO pathway, or a downstream product related thereto such as an ester or amide thereof. Exemplary 3-hydroxybutyryl-CoA, 3-HBal, 3-HB, or 1,3-BDO pathways are shown in FIG. 1 and are described herein.

It is understood that any of the pathways disclosed herein, such as described in the Examples and exemplified in the Figures, including the pathways of FIG. 1, can be utilized to generate a cell that produces any pathway intermediate or product, as desired, in particular a pathway that utilizes a thiolase and/or a 3-hydroxybutyryl-CoA dehydrogenase of the invention. As disclosed herein, such a cell that produces an intermediate can be used in combination with another cell expressing one or more upstream or downstream pathway enzymes to produce a desired product. However, it is understood that a cell that produces a acetoacetyl-CoA, 3-hydroxybutyryl-CoA, 3-HBal, 3-HB, or 1,3-BDO pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, a product or pathway intermediate that is a carboxylic acid can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

Cells of the invention can be produced by introducing an expressible nucleic acid encoding a thiolase and/or a 3-hydroxybutyryl-CoA dehydrogenase of the invention, and optionally expressible nucleic acids encoding one or more of the enzymes or proteins participating in one or more acetoacetyl-CoA, 3-hydroxybutyryl-CoA, 3-HBal, 3-HB, or 1,3-BDO biosynthetic pathways, and further optionally a nucleic acid encoding an enzyme that produces a downstream product related to acetoacetyl-CoA, 3-hydroxybutyryl-CoA, 3-HBal, 3-HB, or 1,3-BDO such as an ester or amide thereof. Depending on the host cell chosen, nucleic acids for some or all of a particular acetoacetyl-CoA, 3-hydroxybutyryl-CoA, 3-HBal, 3-HB, or 1,3-BDO biosynthetic pathway, or downstream product, can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid can be included for the deficient enzyme(s) or protein(s) to achieve 3-HBal or 1,3-BDO biosynthesis, or exogenous expression of endogenously expressed genes can be provided to increase expression of pathway enzymes, if desired. Thus, a cell of the invention can be produced by introducing a thiolase and/or a 3-hydroxybutyryl-CoA dehydrogenase of the invention, and optionally exogenous enzyme or protein activities to obtain a desired biosynthetic pathway, or by introducing one or more exogenous enzyme or protein activities, including a thiolase and/or a 3-hydroxybutyryl-CoA dehydrogenase of the invention that, together with one or more endogenous enzymes or proteins, produces a desired product such as acetoacetyl-CoA, 3-hydroxybutyryl-CoA, 3-HBal, 3-HB, 1,3-BDO, or a downstream product related thereto such as an ester or amide thereof.

Host cells can be selected from, and the non-natural cells expressing a thiolase and/or a 3-hydroxybutyryl-CoA dehydrogenase of the invention generated in, for example, bacteria, yeast, fungus or any of a variety of microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida. E. coli* is a particularly useful host organism since it is a well characterized microbial organism suitable for genetic engineering.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. A particularly useful host organism that is a yeast includes *Saccharomyces cerevisiae*.

Although generally described herein as utilizing a cell that is a microbial organism as a host cell, particularly for producing acetoacetyl-CoA, 3-hydroxybutyryl-CoA, 3-HBal, 3-HB, 1,3-BDO, or a downstream product related thereto such as an ester or amide thereof, it is understood that a host cell can be a cell line of a higher eukaryote, such as a mammalian cell line or insect cell line. Thus, it is understood that reference herein to a host cell that is a microbial organism can alternatively utilize a higher eukaryotic cell line to produce a desired product. Exemplary higher eukaryotic cell lines include, but are not limited to, Chinese hamster ovary (CHO), human (Hela, Human Embryonic Kidney (HEK) 293, Jurkat), mouse (3T3), primate (Vero), insect (Sf9), and the like. Such cell lines are commercially available (see, for example, the American Type Culture Collection (ATCC; Manassas Va.); Thermo Fisher Scientific, Walthan, Mass.). It is understood that any suitable host cell can be used to introduce a 3-hydroxybutyryl-CoA dehydrogenase of the invention, and optionally metabolic and/or genetic modifications to produce a desired product.

In some embodiments, a cell comprises a nucleic acid, a vector, a polypeptide (e.g., a thiolase or a 3-hydroxybutyryl-CoA dehydrogenase), and/or a polypeptide variant described herein. In the case of cells comprising a nucleic acid described herein, the nucleic acid can exist as part of a chromosome of the cell (e.g. integrated into a chromosome of a host cell), or it can exist extrachromosomally (e.g. in a plasmid or episome). When integrated into a chromosome, the site of integration can be non-directed (e.g. random or selected at random from two or more sites) or site-specific (e.g. utilizing recombination signals known in the art, or relying on homologous recombination directed by homologous sequences flanking a target integration site). Exemplary methods for introducing nucleic acids into host cells are provided in Sambrook et al. and Ausubel et al., referenced above. In some embodiments, the cell comprises at least one substrate for a thiolase and/or a 3-hydroxybutyryl-CoA dehydrogenase encoded by a nucleic acid molecule described herein. Non-limiting examples of such substrates include acetyl-CoA (a thiolase substrate) and acetoacetyl-CoA (a 3-hydroxybutyryl-CoA dehydrogenase substrate).

Depending on the acetoacetyl-CoA, 3-hydroxybutyryl-CoA, 3-HBal, 3-HB, or 1,3-BDO biosynthetic pathway constituents of a selected host cell, the non-naturally occurring cells of the invention will include at least one exogenously expressed acetoacetyl-CoA, 3-hydroxybutyryl-CoA, 3-HBal, 3-hydroxybutyrate (3-HB), or 1,3-BDO pathway-encoding nucleic acid and up to all encoding nucleic acids for one or more acetoacetyl-CoA, 3-hydroxybutyryl-CoA, 3-HBal, 3-HB, or 1,3-BDO biosynthetic pathways, or a downstream product related thereto such as an ester or amide thereof, including a thiolase and/or a 3-hydroxybutyryl-CoA dehydrogenase of the invention. For example, acetoacetyl-CoA, 3-hydroxybutyryl-CoA, 3-HBal, 3-HB, or 1,3-BDO biosynthesis can be established in a host deficient in a pathway enzyme or protein through exogenous expression of the corresponding encoding nucleic acid, including a thiolase and/or a 3-hydroxybutyryl-CoA dehydrogenase of the invention. In a host deficient in all enzymes or proteins of a acetoacetyl-CoA, 3-hydroxybutyryl-CoA, 3-HBal, 3-HB, or 1,3-BDO pathway, or a downstream product related thereto such as an ester or amide thereof, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of acetoacetyl-CoA, 3-hydroxybutyryl-CoA, 3-HBal, 3-HB, 1,3-BDO pathway, or a downstream product related thereto such as an ester or amide thereof, can be included, including a 3-hydroxybutyryl-CoA dehydrogenase of the invention. In some embodiments, a cell comprising a thiolase and/or a 3-hydroxybutyryl-CoA dehydrogenase is modified to replace or supplement an endogenous thiolase and/or endogenous 3-hydroxybutyryl-CoA dehydrogenase with a thiolase and/or 3-hydroxybutyryl-CoA dehydrogenase of the invention.

Given the teachings and guidance provided herein, those skilled in the art will understand that the number of encoding nucleic acids to introduce in an expressible form will, at least, parallel the acetoacetyl-CoA, 3-hydroxybutyryl-CoA, 3-HBal, 3-HB, or 1,3-BDO pathway deficiencies of the selected host cell if a 3-hydroxybutyryl-CoA, 3-HBal, 3-HB, or 1,3-BDO pathway is to be included in the cell. Therefore, a non-naturally occurring cell of the invention can have one, two, three, four, five, six, seven, eight, and so forth, depending on the particular pathway, up to all nucleic acids encoding the enzymes or proteins constituting an acetoacetyl-CoA, 3-hydroxybutyryl-CoA, 3-HBal, 3-HB, or 1,3-BDO biosynthetic pathway disclosed herein. In some embodiments, the non-naturally occurring cells also can include other genetic modifications that facilitate or optimize acetoacetyl-CoA, 3-hydroxybutyryl-CoA, 3-HBal, 3-HB, or 1,3-BDO biosynthesis or that confer other useful functions onto the host cell. One such other functionality can include, for example, augmentation of the synthesis of one or more of the acetoacetyl-CoA, 3-hydroxybutyryl-CoA, 3-HBal, 3-HB, or 1,3-BDO pathway precursors such acetyl-CoA.

Generally, a host cell is selected such that it can express a thiolase and/or a 3-hydroxybutyryl-CoA dehydrogenase of the invention, and optionally produces the precursor of a acetoacetyl-CoA, 3-hydroxybutyryl-CoA, 3-HBal, 3-HB, or 1,3-BDO pathway, in a cell containing such a pathway, either as a naturally produced molecule or as an engineered product that either provides de novo production of a desired precursor or increased production of a precursor naturally produced by the host cell. A host organism can be engineered to increase production of a precursor, as disclosed herein. In addition, a cell that has been engineered to produce a desired precursor can be used as a host organism and further engineered to express enzymes or proteins of an acetoacetyl-CoA, 3-hydroxybutyryl-CoA, 3-HBal, 3-HB, or 1,3-BDO pathway, or a downstream product related thereto such as an ester or amide thereof, if desired.

In some embodiments, a non-naturally occurring cell of the invention is generated from a host that contains the enzymatic capability to synthesize acetoacetyl-CoA, 3-hydroxybutyryl-CoA, 3-HBal, 3-HB, or 1,3-BDO, or a downstream product related thereto such as an ester or amide thereof. In this specific embodiment it can be useful to increase the synthesis or accumulation of an acetoacetyl-CoA, 3-hydroxybutyryl-CoA, 3-HBal, 3-HB, or 1,3-BDO pathway product to, for example, drive acetoacetyl-CoA, 3-hydroxybutyryl-CoA, 3-HBal, 3-HB, or 1,3-BDO pathway reactions toward 3-hydroxybutyryl-CoA, 3-HBal, 3-HB, or 1,3-BDO production, or a downstream product related thereto such as an ester or amide thereof. Increased synthesis or accumulation can be accomplished by, for example, overexpression of nucleic acids encoding one or more of the above-described acetoacetyl-CoA, 3-hydroxybutyryl-CoA, 3-HBal, 3-HB, or 1,3-BDO pathway enzymes or proteins, including a thiolase and/or a 3-hydroxybutyryl-CoA dehydrogenase of the invention. Overexpression of the enzyme or enzymes and/or protein or proteins of the acetoacetyl-CoA, 3-hydroxybutyryl-CoA, 3-HBal, 3-HB, or 1,3-BDO pathway can occur, for example, through exogenous expression of the endogenous gene or genes, or through exogenous expression of the heterologous gene or genes, including exogenous expression of a thiolase and/or 3-hydroxybutyryl-CoA dehydrogenase of the invention. Therefore, naturally occurring organisms can be readily converted to non-naturally occurring cells of the invention, for example, producing acetoacetyl-CoA, 3-hydroxybutyryl-CoA, 3-HBal, 3-HB, or 1,3-BDO, or a downstream product related thereto such as an ester or amide thereof, through overexpression of one, two, three, four, five, six, seven, eight, or more, up to all nucleic acids encoding acetoacetyl-CoA, 3-hydroxybutyryl-CoA, 3-HBal, 3-HB, or 1,3-BDO biosynthetic pathway enzymes or proteins, or enzymes that produce a downstream product related thereto such as an ester or amide thereof. In addition, a non-naturally occurring organism can be generated by mutagenesis of an endogenous gene that results in an increase in activity of an enzyme in the acetoacetyl-CoA, 3-hydroxybutyryl-CoA, 3-HBal, 3-HB, or 1,3-BDO biosynthetic pathway, or a downstream product related thereto such as an ester or amide thereof.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring cell.

It is understood that any of the one or more exogenous nucleic acids can be introduced into a cell to produce a non-naturally occurring cell of the invention. The nucleic acids can be introduced so as to confer, for example, an acetoacetyl-CoA, 3-hydroxybutyryl-CoA, 3-HBal, 3-HB, 1,3-BDO, or a downstream product related thereto such as an ester or amide thereof, biosynthetic pathway onto the cell, including introducing a nucleic acid encoding a thiolase and/or a 3-hydroxybutyryl-CoA dehydrogenase of the invention. Alternatively, encoding nucleic acids can be introduced to produce a cell having the biosynthetic capability to catalyze some of the required reactions to confer acetoacetyl-CoA, 3-hydroxybutyryl-CoA, 3-HBal, 3-HB, or 1,3-BDO biosynthetic capability to produce an intermediate. For example, a non-naturally occurring cell having an acetoacetyl-CoA, 3-hydroxybutyryl-CoA, 3-HBal, 3-HB, or 1,3-BDO biosynthetic pathway can comprise at least two exogenous nucleic acids encoding desired enzymes or proteins, including a thiolase and/or a 3-hydroxybutyryl-CoA dehydrogenase of the invention. Thus, it is understood that any combination of two or more enzymes or proteins of a biosynthetic pathway can be included in a non-naturally occurring cell of the invention, including a thiolase and/or a 3-hydroxybutyryl-CoA dehydrogenase of the invention. Similarly, it is understood that any combination of three or more enzymes or proteins of a biosynthetic pathway can be included in a non-naturally occurring cell of the invention, as desired, so long as the combination of enzymes and/or proteins of the desired biosynthetic pathway results in production of the corresponding desired product. Similarly, any combination of four or more enzymes or proteins of a biosynthetic pathway as disclosed herein can be included in a non-naturally occurring cell of the invention, as desired, so long as the combination of enzymes and/or proteins of the desired biosynthetic pathway results in production of the corresponding desired product.

In addition to the biosynthesis of acetoacetyl-CoA, 3-hydroxybutyryl-CoA, 3-HBal, 3-HB, or 1,3-BDO, or a downstream product related thereto such as an ester or amide thereof, as described herein, the non-naturally occurring cells and methods of the invention also can be utilized in various combinations with each other and/or with other cells and methods well known in the art to achieve product biosynthesis by other routes. For example, one alternative to produce 3-HBal or 1,3-BDO other than use of the 3-HBal or 1,3-BDO producers is through addition of another cell capable of converting a 3-HBal or 1,3-BDO pathway intermediate to 3-HBal or 1,3-BDO. One such procedure includes, for example, the fermentation of a cell that produces a 3-HBal or 1,3-BDO pathway intermediate. The 3-HBal or 1,3-BDO pathway intermediate can then be used as a substrate for a second cell that converts the 3-HBal or 1,3-BDO pathway intermediate to 3-HBal or 1,3-BDO. The 3-HBal or 1,3-BDO pathway intermediate can be added directly to another culture of the second organism or the original culture of the acetoacetyl-CoA, 3-hydroxybutyryl-CoA, 3-HBal, 3-HB, or 1,3-BDO pathway intermediate producers can be depleted of these cells by, for example, cell separation, and then subsequent addition of the second organism to the fermentation broth can be utilized to produce the final product without intermediate purification steps. A cell that produces a downstream product related to acetoacetyl-CoA, 3-hydroxybutyryl-CoA, 3-HBal, 3-HB, or 1,3-BDO such as an ester or amide thereof, can optionally be included to produce such a downstream product.

In some embodiments, a non-naturally occurring cell having an acetoacetyl-CoA, 3-hydroxybutyryl-CoA, 3-HBal, 3-HB, or 1,3-BDO biosynthetic pathway comprises a thiolase of the present invention, and produces (alone or in combination with one or more other cells having a 3-hydroxybutyryl-CoA, 3-HBal, 3-HB, or 1,3-BDO biosynthetic pathway) an increased amount of 1,3-BDO as compared to a cell in which the thiolase instead comprises the amino acid sequence of SEQ ID NO: 6 (alone or in the combination with the one or more other cells having a 3-hydroxybutyryl-CoA, 3-HBal, 3-HB, or 1,3-BDO biosynthetic pathway, respectively). In some embodiments, the increased 1,3-BDO is an increase of at least about 1%, 2%, 3%, 4%, 5%, 10%, 15%, 20%, 25%, 30%, 35%, 40%, 50%, or more. In some embodiments, increased 1,3-BDO production is measured after a specified time and/or under specified culture conditions. For example, 1,3-BDO production can be measured after at least about 10, 20, 30, 40, or 50 hours of culture. In some embodiments, measurement is after 30 hours of culture. In some embodiments, culture conditions include a peak weight-based oxygen update rate (wOUR) of about or less than about 50 mmol $O_2$/kg/hr, 40 mmol $O_2$/kg/hr, 30 mmol $O_2$/kg/hr, 25 mmol $O_2$/kg/hr, 10 $O_2$/kg/hr or lower. In some embodiments, the wOUR is about 25 mmol $O_2$/kg/hr (wOUR 25) or about 30 mmol $O_2$/kg/hr (wOUR 30).

In some embodiments, a non-naturally occurring cell having an acetoacetyl-CoA, 3-hydroxybutyryl-CoA, 3-HBal, 3-HB, or 1,3-BDO biosynthetic pathway comprises a thiolase of the present invention, and produces (alone or in combination with one or more other cells having a 3-hydroxybutyryl-CoA, 3-HBal, 3-HB, or 1,3-BDO biosynthetic pathway) a decreased amount of pyruvate as compared to a cell in which the thiolase instead comprises the amino acid sequence of SEQ ID NO: 6 (alone or in the combination with the one or more other cells having a 3-hydroxybutyryl-CoA, 3-HBal, 3-HB, or 1,3-BDO biosynthetic pathway, respectively). In some embodiments, the decreased pyruvate is a decrease of at least about 1%, 5%, 10%, 15%, 20%, 25%, 30%, 40%, 50%, 60%, 70%, 80%, 90%, or more. In some embodiments, decreased pyruvate production is measured after a specified time and/or under specified culture conditions. For example, pyruvate production can be measured after at least about 10, 20, 30, 40, or 50 hours of culture. In some embodiments, measurement is after 30 hours of culture. In some embodiments, culture conditions include a peak weight-based oxygen update rate (wOUR) of about or less than about 50 mmol $O_2$/kg/hr, 40 mmol $O_2$/kg/hr, 30 mmol $O_2$/kg/hr, 25 mmol $O_2$/kg/hr, 10 $O_2$/kg/hr or lower. In some embodiments, the wOUR is about 25 mmol $O_2$/kg/hr (wOUR 25) or about 30 mmol $O_2$/kg/hr (wOUR 30).

In some embodiments, a non-naturally occurring cell having an acetoacetyl-CoA, 3-hydroxybutyryl-CoA, 3-HBal, 3-HB, or 1,3-BDO biosynthetic pathway comprises a thiolase of the present invention, and produces (alone or in combination with one or more other cells having a 3-hydroxybutyryl-CoA, 3-HBal, 3-HB, or 1,3-BDO biosynthetic pathway) 1,3-BDO and pyruvate at an increased ratio of 1,3-BDO to pyruvate as compared to a cell in which the thiolase instead comprises the amino acid sequence of SEQ ID NO: 6 (alone or in the combination with the one or more other cells having a 3-hydroxybutyryl-CoA, 3-HBal, 3-HB, or 1,3-BDO biosynthetic pathway, respectively). In some embodiments, the increased ratio of 1,3-BDO to pyruvate is an increase of at least about 1.5-fold, 2-fold, 3-fold, 4-fold, 5-fold, 5-fold, 6-fold, 7-fold, 8-fold, 9-fold, 10-fold, 20-fold, or more. In some embodiments, increased ratio of 1,3-BDO to pyruvate is measured after a specified time and/or under specified culture conditions. For example, the ratio of 1,3-BDO to pyruvate can be measured after at least about 10, 20, 30, 40, or 50 hours of culture. In some embodiments, measurement is after 30 hours of culture. In some embodiments, culture conditions include a peak weight-based oxygen update rate (wOUR) of about or less than about 50 mmol $O_2$/kg/hr, 40 mmol $O_2$/kg/hr, 30 mmol $O_2$/kg/hr, 25 mmol $O_2$/kg/hr, 10 $O_2$/kg/hr or lower. In some embodiments, the wOUR is about 25 mmol $O_2$/kg/hr (wOUR 25) or about 30 mmol $O_2$/kg/hr (wOUR 30).

Alternatively, enzymatic conversions can be carried out in vitro, with a combination of enzymes or sequential exposure of substrates to enzymes that result in conversion of a substrate to a desired product. As another alternative, a combination of cell-based conversions and in vitro enzymatic conversions can be used, if desired.

In some embodiments, the non-naturally occurring cells and methods of the invention can be assembled in a wide variety of subpathways to achieve biosynthesis of, for example, acetoacetyl-CoA, 3-hydroxybutyryl-CoA, 3-HBal, 3-HB, or 1,3-BDO, or a downstream product related thereto such as an ester or amide thereof. In these embodiments, biosynthetic pathways for a desired product of the invention can be segregated into different cells, and the different cells can be co-cultured to produce the final product. In such a biosynthetic scheme, the product of one cell is the substrate for a second cell until the final product is synthesized. For example, the biosynthesis of acetoacetyl-CoA, 3-hydroxybutyryl-CoA, 3-HBal, 3-HB, or 1,3-BDO, or a downstream product related thereto such as an ester or amide thereof, can be accomplished by constructing a cell that contains biosynthetic pathways for conversion of one pathway intermediate to another pathway intermediate or the product. Alternatively, acetoacetyl-CoA, 3-hydroxybutyryl-CoA, 3-HBal, 3-HB, or 1,3-BDO also can be biosynthetically produced from cells through co-culture or co-fermentation using two different cells in the same vessel, where the first cell produces an acetoacetyl-CoA, 3-hydroxybutyryl-CoA, 3-HBal, 3-HB, or 1,3-BDO intermediate and the second cell converts the intermediate to 3-hydroxybutyryl-CoA, 3-HBal, 3-HB, or 1,3-BDO, or a downstream product related thereto such as an ester or amide thereof.

Given the teachings and guidance provided herein, those skilled in the art will understand that a wide variety of combinations and permutations exist for the non-naturally occurring cells and methods of the invention together with other cells, with the co-culture of other non-naturally occurring cells having subpathways and with combinations of other chemical and/or biochemical procedures well known in the art to produce acetoacetyl-CoA, 3-hydroxybutyryl-CoA, 3-HBal, 3-HB, or 1,3-BDO, or a downstream product related thereto such as an ester or amide thereof.

Sources of encoding nucleic acids for an acetoacetyl-CoA, 3-hydroxybutyryl-CoA, 3-HBal, 3-HB, or 1,3-BDO pathway enzyme or protein, or a downstream product related thereto such as an ester or amide thereof, can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Paphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens; Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilus, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum,* marine gamma proteobacterium, butyrate-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza saliva, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismor Pyrobaculum aerophilum, Mycobacterium smegmatis*MC2 155, *Mycobacterium avium* subsp. *paratuberculosis* K-10, *Mycobacterium marinum* M, *Tsukamurella paurometabola* DSM 20162, *Cyanobium* PCC7001, *Dictyostelium discoideum* AX4, *Acidaminococcus fermentans, Acinetobacter baylyi, Acinetobacter calcoaceticus, Aquifex aeolicus, Arabidopsis thaliana, Archaeoglobus fulgidus, Aspergillus niger, Aspergillus terreus, Bacillus subtilis, Bos Taurus, Candida albicans, Candida tropicalis, Chlamydomonas reinhardtii, Chlorobium tepidum, Citrobacter koseri, Citrus junos, Clostridium acetobutylicum, Clostridium kluyveri, Clostridium saccharoperbutylacetonicum, Cyanobium* PCC7001, *Desulfatibacillum alkenivorans, Dictyostelium discoideum, Fusobacterium nucleatum, Haloarcula marismortui, Homo sapiens, Hydrogenobacter thermophilus, Klebsiella pneumoniae, Kluyveromyces lactis, Lactobacillus brevis, Leuconostoc mesenteroides, Metallosphaera sedula, Methanothermobacter thermautotrophicus, Mus musculus, Mycobacterium avium, Mycobacterium bovis, Mycobacterium marinum, Mycobacterium smegmatis, Nicotiana tabacum, Nocardia iowensis, Oryctolagus cuniculus, Penicillium chrysogenum, Pichia pastoris, Porphyromonas gingivalis, Porphyromonas gingivalis, Pseudomonas aeruginos, Pseudomonas putida, Pyrobaculum aerophilum, Ralstonia eutropha, Rattus norvegicus, Rhodobacter sphaeroides, Saccharomyces cerevisiae, Salmonella enteric, Salmonella typhimurium, Schizosaccharomyces pombe, Sulfolobus acidocaldarius, Sulfolobus solfataricus, Sulfolobus tokodaii, Thermoanaerobacter tengcongensis, Thermus thermophilus, Trypanosoma brucei, Tsukamurella paurometabola, Yarrowia lipolytica, Zoogloea ramigera* and *Zymomonas mobilis, Clostridium* species, including but no limited to *Clostridium saccharoperbutylacetonicum, Clostridium beijerinckii, Clostridium saccharobutylicum, Clostridium botulinum, Clostridium methylpentosum, Clostridium sticklandii, Clostridium phytofermentans, Clostridium saccharolyticum, Clostridium asparagiforme, Clostridium celatum, Clostridium carboxidivorans, Clostridium clostridioforme, Clostridium bolteae, Caldalkalibacillus thermarum, Clostridium botulinum, Pelosinus fermentans, Thermoanaerobacterium thermosaccharolyticum, Desulfosporosinus speices, Thermoanaerobacterium* species, including but not limited to *Thermoanaerobacterium saccharolyticum, Thermoanaerobacterium xylanolyticum, Acetonema longum, Geobacillus* species, including but not limited to *Geobacillus thermoglucosidans, Bacillus azotoformans, Thermincola potens, Fusobacterium* species, including but not limited to *Fusobacterium nucleatum, Fusobacterium ulcerans, Fusobacterium varium, Ruminococcus* species, including but not limited to *Ruminococcus gnavus, Ruminococcus obeum, Lachnospiraceae* bacterium, *Flavonifractor plautii, Roseburia inulinivorans, Acetobacterium woodii, Eubacterium* species, including but not limited to *Eubacterium plexicaudatum, Eubacterium*

*hallii, Eubacterium limosum, Eubacterium yurii, Eubacteriaceae bacterium, Thermosediminibacter oceani, Ilyobacter polytropus, Shuttleworthia satelles, Halanaerobium saccharolyticum, Thermoanaerobacter ethanolicus, Rhodospirillum rubrum, Vibrio, Propionibacterium propionicum* as well as other exemplary species disclosed herein or available as source organisms for corresponding genes, including the source organisms of the 3-hydroxybutyryl-CoA dehydrogenases described in Table 2. In some embodiments, the thiolase is a thiolase derived from *Ralstonia eutropha*. In some embodiments, the thiolase is not a thiolase of *Clostridium acetobutylicum*, such as a thiolase having the sequence of SEQ ID NO: 6. However, with the complete genome sequence available for now more than 550 species (with more than half of these available on public databases such as the NCBI), including 395 microorganism genomes and a variety of yeast, fungi, plant, and mammalian genomes, the identification of genes encoding the acetoacetyl-CoA, 3-hydroxybutyryl-CoA, 3-HBal, 3-HB, or 1,3-BDO biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of acetoacetyl-CoA, 3-hydroxybutyryl-CoA, 3-HBal, 3-HB, or 1,3-BDO, or a downstream product related thereto such as an ester or amide thereof, including expression of a 3-hydroxybutyryl-CoA dehydrogenase of the invention, described herein with reference to a particular organism such as *E. coli* can be readily applied to other cells such as microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative acetoacetyl-CoA, 3-hydroxybutyryl-CoA, 3-HBal, 3-HB, or 1,3-BDO biosynthetic pathway exists in an unrelated species, acetoacetyl-CoA, 3-hydroxybutyryl-CoA, 3-HBal, 3-HB, or 1,3-BDO biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all cells using the cognate metabolic alterations to those exemplified herein to construct a cell in a species of interest that will synthesize acetoacetyl-CoA, 3-hydroxybutyryl-CoA, 3-HBal, 3-HB, or 1,3-BDO, or a downstream product related thereto such as an ester or amide thereof, if desired, including introducing a 3-hydroxybutyryl-CoA dehydrogenase of the invention.

Methods for constructing and testing the expression levels of a non-naturally occurring host producing acetoacetyl-CoA, 3-hydroxybutyryl-CoA, 3-HBal, 3-HB, or 1,3-BDO, or a downstream product related thereto such as an ester or amide thereof, including a thiolase and/or a 3-hydroxybutyryl-CoA dehydrogenase of the invention, can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

An exogenous nucleic acid encoding a thiolase and/or a 3-hydroxybutyryl-CoA dehydrogenase of the invention, and optionally exogenous nucleic acid sequences involved in a pathway for production of acetoacetyl-CoA, 3-hydroxybutyryl-CoA, 3-HBal, 3-HB, or 1,3-BDO, or a downstream product related thereto such as an ester or amide thereof, can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include a nucleic acid encoding a thiolase and/or a 3-hydroxybutyryl-CoA dehydrogenase of the invention, and/or optionally one or more 3-HBal or 1,3-BDO biosynthetic pathway encoding nucleic acids, or nucleic acids encoding an enzyme that produces a downstream product related to 3-HBal or 1,3-BDO such as an ester or amide thereof, as exemplified herein operably linked to expression control sequences functional in the host organism. Expression vectors applicable for use in the host cells of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences encoding a thiolase and/or a 3-hydroxybutyryl-CoA dehydrogenase of the invention or encoding polypeptides involved in a metabolic or synthetic pathway can be confirmed using methods well known in the art.

Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

A vector or expression vector can also be used to express an encoded nucleic acid to produce an encoded polypeptide by in vitro transcription and translation. Such a vector or expression vector will comprise at least a promoter, and includes the vectors described herein above. Such a vector for in vitro transcription and translation generally is double stranded DNA. Methods of in vitro transcription and translation are well known to those skilled in the art (see Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999)). Kits for in vitro transcription and translation are also commercially available (see, for example, Promega, Madison, Wis.; New England Biolabs, Ipswich, Mass.; Thermo Fisher Scientific, Carlsbad, Calif.).

In some aspects, the present disclosure provides a method for constructing a host strain comprising introducing a vector described herein into a cell capable of fermentation. In some aspects, the present disclosure provides a method for producing a polypeptide variant disclosed herein, the method comprising: (a) expressing the polypeptide in a cell, or (b) in vitro transcribing and translating a nucleic acid molecule or vector described herein.

In some aspects, the present disclosure provides methods for producing acetoacetyl-CoA, 3-hydroxybutyryl-CoA (3-HB-CoA), 3-hydroxybutyraldehyde (3-HBal), 3-hydroxybutyrate (3-HB), and/or 1,3-butanediol (1,3-BDO), and methods for producing acetoacetyl-CoA, 3-hydroxybutyryl-CoA (3-HB-CoA), 3-hydroxybutyraldehyde (3-HBal), 3-hydroxybutyrate (3-HB), 1,3-butanediol (1,3-BDO), and/or an ester or amide thereof. In some embodiments, the method comprises culturing a cell disclosed herein, wherein the culturing is under conditions and for a sufficient period of time to produce acetoacetyl-CoA, 3-HB-CoA, 3-HBal, 3-HB, and/or 1,3-BDO. In some embodiments, the cell is in a substantially anaerobic culture medium. In some embodiments, the method further comprises isolating or purifying the 3-HB-CoA, 3-HBal, 3-HB, 1,3-BDO, and/or an ester or amide thereof. In some embodiments, the method further comprises distillation. In some embodiments, the method comprises providing a substrate for a polypeptide variant of the disclosure, and converting the substrate to 3-HB-CoA, 3-HBal, 3-HB, or 1,3-BDO through one or more reactions. In some embodiments, the polypeptide variant is present in a cell, in a cell lysate, or is isolated from a cell or cell lysate. In some embodiments, the method comprises incubating a lysate of a cell disclosed herein to produce the 3-HB-CoA, 3-HBal, 3-HB, and/or 1,3-BDO. In some embodiments, the cell lysate is mixed with a second cell lysate, and the second cell lysate comprises an enzymatic activity to produce a substrate of the polypeptide variant, or a downstream product of 3-HB-CoA, 3-HBa1,3-HB, and/or 1,3-BDO.

Suitable purification and/or assays to test for the expression of a thiolase and/or a 3-hydroxybutyryl-CoA dehydrogenase, or for production of acetoacetyl-CoA, 3-hydroxybutyryl-CoA, 3-HBal, 3-HB, or 1,3-BDO, or a downstream product related thereto such as an ester or amide thereof, including assays to test for 3-hydroxybutyryl-CoA dehydrogenase activity, can be performed using any suitable method (see e.g., the Examples). Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art (see also Example).

The acetoacetyl-CoA, 3-hydroxybutyryl-CoA, 3-HBal, 3-HB, or 1,3-BDO, or other desired product, such as a downstream product related thereto such as an ester or amide thereof, can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration.

In some embodiments, non-naturally occurring cells expressing a thiolase and/or a 3-hydroxybutyryl-CoA dehydrogenase of the invention described herein are cultured to produce and/or secrete biosynthetic products of the invention. For example, the cells that produce acetoacetyl-CoA, 3-hydroxybutyryl-CoA, 3-HBal, 3-HB, or 1,3-BDO, or a downstream product related thereto such as an ester or amide thereof, can be cultured for the biosynthetic production of acetoacetyl-CoA, 3-hydroxybutyryl-CoA, 3-HBal, 3-HB, or 1,3-BDO, or a downstream product related thereto such as an ester or amide thereof. Accordingly, in some embodiments, the invention provides culture medium containing the acetoacetyl-CoA, 3-hydroxybutyryl-CoA, 3-HBal, 3-HB, or 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate described herein. In some aspects, the culture medium can also be separated from the non-naturally occurring cells of the invention that produced acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate. Methods for separating a cell from culture medium are well known in the art. Exemplary methods include filtration, flocculation, precipitation, centrifugation, sedimentation, and the like.

For the production of a thiolase and/or a 3-hydroxybutyryl-CoA dehydrogenase of the invention, or of acetoacetyl-CoA, 3-hydroxybutyryl-CoA, 3-HBal, 3-HB, or 1,3-BDO, or a downstream product related thereto such as an ester or amide thereof, in a cell expressing a thiolase and/or a 3-hydroxybutyryl-CoA dehydrogenase of the invention, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United States publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high yields of a desired product such as 3-hydroxybutyryl-CoA, 3-HBal, 3-HB, or 1,3-BDO, or a downstream product related thereto such as an ester or amide thereof. In some embodiments, culture conditions include a peak weight-based oxygen update rate (wOUR) of about or less than about 50 mmol $O_2$/kg/hr, 40 mmol $O_2$/kg/hr, 30 mmol $O_2$/kg/hr, 25 mmol $O_2$/kg/hr, 10 $O_2$/kg/hr or lower. In some embodiments, the wOUR is about 25 mmol $O_2$/kg/hr (wOUR 25) or about 30 mmol $O_2$/kg/hr (wOUR 30).

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring cell. Such sources include, for example: sugars such as glucose, xylose, arabinose, galactose, mannose, fructose, sucrose and starch; or glycerol, and it is understood that a carbon source can be used alone as the sole source of carbon or in combination with other carbon sources described herein or known in the art. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the cells of the invention for the expression of a thiolase and/or a 3-hydroxybutyryl-CoA dehydrogenase of the invention, and optionally production of acetoacetyl-CoA, 3-hydroxybutyryl-CoA, 3-HBal, 3-HB, or 1,3-BDO, or a downstream product thereof, such as an ester or amide thereof.

In addition to renewable feedstocks such as those exemplified above, the cells of the invention that produce acetoacetyl-CoA, 3-hydroxybutyryl-CoA, 3-HBal, 3-HB, or 1,3-BDO or a downstream product thereof, such as an ester or amide thereof, also can be modified for growth on syngas as its source of carbon. In this specific embodiment, one or more proteins or enzymes are expressed in the 3-hydroxybutyryl-CoA, 3-HBal, 3-HB, or 1,3-BDO producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, Acetogenesis, pp. 3-60 Chapman and Hall, New York, (1994)). This can be summarized by the following equation:

$$2CO_2 + 4H_2 + n\text{ADP} + n\text{Pi} \rightarrow CH_3COOH + 2H_2O + n\text{ATP}$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC)(see WO2009/094485). Following the teachings and guidance provided herein for introducing a sufficient number of encoding nucleic acids to generate a 3-hydroxybutyryl-CoA, 3-HBal, 3-HB, or 1,3-BDO pathway, or a downstream product related thereto such as an ester or amide thereof, including a nucleic acid encoding a 3-hydroxybutyryl-CoA dehydrogenase of the invention, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the cells of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a 3-hydroxybutyryl-CoA, 3-HBal, 3-HB, or 1,3-BDO pathway, or pathway to generate a downstream product related thereto such as an ester or amide thereof, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the cells of the invention such that the modified organism contains a reductive TCA pathway.

Accordingly, given the teachings and guidance provided herein, those skilled in the art will understand that a non-naturally occurring cell can be produced that secretes the biosynthesized compounds of the invention when grown on a carbon source such as a carbohydrate. Such compounds include, for example, acetoacetyl-CoA, 3-hydroxybutyryl-CoA, 3-HBal, 3-HB, 1,3-BDO, a downstream product related thereto such as an ester or amide thereof, and any of the intermediate metabolites in the acetoacetyl-CoA, 3-hydroxybutyryl-CoA, 3-HBal, 3-HB, or 1,3-BDO pathway. All that is required is to engineer in one or more of the required enzyme or protein activities to achieve biosynthesis of the desired compound or intermediate including, for example, inclusion of some or all of the biosynthetic pathways for acetoacetyl-CoA, 3-hydroxybutyryl-CoA, 3-HBal, 3-HB, or 1,3-BDO, or a downstream product related thereto such as an ester or amide thereof, including a thiolase and/or a 3-hydroxybutyryl-CoA dehydrogenase of the invention. Accordingly, the invention provides a non-naturally occurring cell that produces and/or secretes acetoacetyl-CoA, 3-hydroxybutyryl-CoA, 3-HBal, 3-HB, or 1,3-BDO, or a downstream product related thereto such as an ester or amide thereof, when grown on a carbohydrate or other carbon source and produces and/or secretes any of the intermediate metabolites shown in the acetoacetyl-CoA, 3-hydroxybutyryl-CoA, 3-HBal, 3-HB, or 1,3-BDO pathway when grown on a carbohydrate or other carbon source. The cells producing acetoacetyl-CoA, 3-hydroxybutyryl-CoA, 3-HBal, 3-HB, or 1,3-BDO, or a downstream product related thereto such as an ester or amide thereof, of the invention can initiate synthesis from an intermediate of a acetoacetyl-CoA, 3-hydroxybutyryl-CoA, 3-HBal, 3-HB, or 1,3-BDO pathway.

The non-naturally occurring cells of the invention are constructed using methods well known in the art as exemplified herein to exogenously express a thiolase and/or a 3-hydroxybutyryl-CoA dehydrogenase of the invention, and optionally at least one nucleic acid encoding a acetoacetyl-CoA, 3-hydroxybutyryl-CoA, 3-HBal, 3-HB, or 1,3-BDO pathway enzyme or protein, or a downstream product related thereto such as an ester or amide thereof. The enzymes or proteins can be expressed in sufficient amounts to produce acetoacetyl-CoA, 3-hydroxybutyryl-CoA, 3-HBal, 3-HB, 1,3-BDO, or a downstream product related thereto such as an ester or amide thereof. It is understood that the cells of the invention are cultured under conditions sufficient to express a thiolase and/or a 3-hydroxybutyryl-CoA dehydrogenase of the invention or produce acetoacetyl-CoA, 3-hydroxybutyryl-CoA, 3-HBal, 3-HB, 1,3-BDO, or a downstream product related thereto such as an ester or amide thereof. Following the teachings and guidance provided herein, the non-naturally occurring cells of the invention can achieve biosynthesis of acetoacetyl-CoA, 3-hydroxybutyryl-CoA, 3-HBal, 3-HB, or 1,3-BDO, or a downstream product related thereto such as an ester or amide thereof, resulting in intracellular concentrations between about 0.1-1000 mM or more. In some embodiments, the intracellular concentration of acetoacetyl-CoA, 3-hydroxybutyryl-CoA, 3-HBal, 3-HB, 1,3-BDO, or a downstream product related thereto such as an ester or amide thereof, is between about 3-150 mM, particularly between about 5-125 mM and more particularly between about 8-100 mM, including about 10 mM, 20 mM, 50 mM, 80 mM, or more. In some embodiments, intracellular concentrations of 3-HB and/or 1,3-BDO are between about 0.25-2 M or more, such as between 0.25-1.75 M, 0.5-1.5 M, 0.75-1.25 M, or at least 1 M. In some embodiments, the intracellular concentration of 3-hydroxybutyryl-CoA is between about 0.1-1000 mM, such as between about 1-750 mM, 5-500 mM, or 8-100 mM, including about 10 mM, 20 mM, 50 mM, 80 mM, or more. In some embodiments, intracellular concentrations between and above each of these exemplary ranges is achieved from the non-naturally occurring cells of the invention.

In some embodiments, a cell of the invention is cultured using well known methods or modifications thereof, as described herein. The culture conditions can include, for example, liquid culture procedures as well as fermentation and other large scale culture procedures. As described herein, particularly useful yields of the biosynthetic products of the invention can be obtained under anaerobic or substantially anaerobic culture conditions. In some embodiments, culture conditions include a peak weight-based oxygen update rate (wOUR) of about or less than about 50 mmol $O_2$/kg/hr, 40 mmol $O_2$/kg/hr, 30 mmol $O_2$/kg/hr, 25 mmol $O_2$/kg/hr, 10 $O_2$/kg/hr or lower. In some embodiments, the wOUR is about 25 mmol $O_2$/kg/hr (wOUR 25) or about 30 mmol $O_2$/kg/hr (wOUR 30).

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring cells as well as other anaerobic conditions well known in the art, in accordance with some embodiments. Under such anaerobic or substantially anaerobic conditions, the acetoacetyl-CoA, 3-hydroxybutyryl-CoA, 3-HBal, 3-HB, or 1,3-BDO producers can synthesize acetoacetyl-CoA, 3-hydroxybutyryl-CoA, 3-HBal, 3-HB, 1,3-BDO, or a downstream product related thereto such as an ester or amide thereof, at intracellular concentrations of 5-10 mM or more as well as all other concentrations exemplified herein. It is understood that, even though the above description refers to intracellular concentrations, acetoacetyl-CoA, 3-hydroxybutyryl-CoA, 3-HBal, 3-HB, or 1,3-BDO producing cells can produce 3-HBal or 1,3-BDO, or a downstream product related thereto such as an ester or amide thereof, intracellularly and/or secrete the product into the culture medium.

As described herein, one exemplary growth condition for achieving biosynthesis of acetoacetyl-CoA, 3-hydroxybutyryl-CoA, 3-HBal, 3-HB, or 1,3-BDO, or a downstream product related thereto such as an ester or amide thereof, includes anaerobic culture or fermentation conditions. In certain embodiments, the non-naturally occurring cells of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an N2/$CO_2$ mixture or other suitable non-oxygen gas or gases.

The culture conditions described herein can be scaled up and grown continuously for manufacturing of acetoacetyl-CoA, 3-hydroxybutyryl-CoA, 3-HBal, 3-HB, or 1,3-BDO, or a downstream product related thereto such as an ester or amide thereof, by a cell of the invention. Exemplary growth procedures include, for example, fed-batch fermentation and batch separation; fed-batch fermentation and continuous separation, or continuous fermentation and continuous separation. Fermentation procedures are particularly useful for the biosynthetic production of commercial quantities of acetoacetyl-CoA, 3-hydroxybutyryl-CoA, 3-HBal, 3-HB, 1,3-BDO, or a downstream product related thereto such as an ester or amide thereof. Generally, and as with non-continuous culture procedures, the continuous and/or near-continuous production of acetoacetyl-CoA, 3-hydroxybutyryl-CoA, 3-HBal, 3-HB, 1,3-BDO, or a downstream product related thereto such as an ester or amide thereof, will include culturing a non-naturally occurring cell producing acetoacetyl-CoA, 3-hydroxybutyryl-CoA, 3-HBal, 3-HB, 1,3-BDO, or a downstream product related thereto such as an ester or amide thereof, in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the cell of the invention is for a sufficient period of time to produce a sufficient amount of product for a desired purpose.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2$/$CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

General fermentation procedures are well known in the art. Briefly, fermentation for the biosynthetic production of acetoacetyl-CoA, 3-hydroxybutyryl-CoA, 3-HBal, 3-HB, 1,3-BDO, or a downstream product related thereto such as an ester or amide thereof, can be utilized in, for example, fed-batch fermentation and batch separation; fed-batch fermentation and continuous separation, or continuous fermentation and continuous separation. Examples of batch and continuous fermentation procedures are well known in the art and described herein.

In addition to the fermentation procedures described herein using the producers of acetoacetyl-CoA, 3-hydroxybutyryl-CoA, 3-HBal, 3-HB, or 1,3-BDO, or a downstream product related thereto such as an ester or amide thereof, of the invention for continuous production of substantial quantities of acetoacetyl-CoA, 3-hydroxybutyryl-CoA, 3-HBal, 3-HB, 1,3-BDO, or a downstream product related thereto such as an ester or amide thereof, the acetoacetyl-CoA, 3-hydroxybutyryl-CoA, 3-HBal, 3-HB, 1,3-BDO, or a downstream product related thereto such as an ester or amide, producers also can be, for example, simultaneously subjected to chemical synthesis and/or enzymatic procedures to convert the product to other compounds, or the product can be separated from the fermentation culture and sequentially subjected to chemical and/or enzymatic conversion to convert the product to other compounds, if desired.

In addition to the culturing and fermentation conditions disclosed herein, growth condition for achieving expression of a thiolase and/or a 3-hydroxybutyryl-CoA dehydrogenase of the invention or biosynthesis of acetoacetyl-CoA, 3-hydroxybutyryl-CoA, 3-HBal, 3-HB, 1,3-BDO, or a downstream product related thereto such as an ester or amide thereof, can include the addition of an osmoprotectant to the culturing conditions. In certain embodiments, the non-naturally occurring cells of the invention can be sustained, cultured or fermented as described herein in the presence of an osmoprotectant. Briefly, an osmoprotectant refers to a compound that acts as an osmolyte and helps a cell as described herein survive osmotic stress. Osmoprotectants include, but are not limited to, betaines, amino acids, and the sugar trehalose. Non-limiting examples of such are glycine betaine, praline betaine, dimethylthetin, dimethyl slfonio-proprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a cell described herein from osmotic stress will depend on the cell used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in acetoacetyl-CoA, 3-hydroxybutyryl-CoA, 3-HBal, 3-HB, or 1,3-BDO, or a downstream product related thereto such as an ester or amide thereof, or any acetoacetyl-CoA, 3-hydroxybutyryl-CoA, 3-HBal, 3-HB, or 1,3-BDO pathway intermediate. The various carbon feedstock and other uptake sources enumerated above will be referred to herein, collectively, as "uptake sources." Uptake sources can provide isotopic enrichment for any atom present in the product acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate, or for side products generated in reactions diverging away from a acetoacetyl-CoA, 3-hydroxybutyryl-CoA, 3-HBal, 3-HB, or 1,3-BDO pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased source derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning" of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950)$^{14}C/^{12}C$ ratio of 1.176±0.010×10$^{-12}$ (Karlen et al., *Arkiv Geofisik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mil. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content of a compound or material and/or prepared downstream products that utilize a compound or material of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides acetoacetyl-CoA, 3-hydroxybutyryl-CoA, 3-HBal, 3-HB, 1,3-BDO, or a downstream product related thereto such as an ester or amide thereof, or a acetoacetyl-CoA, 3-hydroxybutyryl-CoA, 3-HBal, 3-HB, or 1,3-BDO pathway intermediate, produced by a cell of the invention, that has a carbon-12, carbon-13, and carbon-14 ratio that reflects an atmospheric carbon, also referred to as environmental carbon, uptake source. For example, in some aspects the acetoacetyl-CoA, 3-hydroxybutyryl-CoA, 3-HBal, 3-HB, 1,3-BDO, or a downstream product related thereto such as an ester or amide thereof, or a acetoacetyl-CoA, 3-hydroxybutyryl-CoA, 3-HBal, 3-HB, or 1,3-BDO pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides acetoacetyl-CoA, 3-hydroxybutyryl-CoA, 3-HBal, 3-HB, 1,3-BDO, or a downstream product related thereto such as an ester or amide thereof, or a acetoacetyl-CoA, 3-hydroxybutyryl-CoA, 3-HBal, 3-HB, or 1,3-BDO pathway intermediate that has a carbon-12, carbon-13, and carbon-14 ratio that reflects petroleum-based carbon uptake source. In this aspect, the 3-HBal or 1,3-BDO, or a downstream product related thereto such as an ester or amide thereof, or a 3-HBal or 1,3-BDO pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides acetoacetyl-CoA, 3-hydroxybutyryl-CoA, 3-HBal, 3-HB, 1,3-BDO, or a downstream product related thereto such as an ester or amide thereof, or an acetoacetyl-CoA, 3-hydroxybutyryl-CoA, 3-HBal, 3-HB, or 1,3-BDO pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate as disclosed herein, and to the products derived therefrom, wherein the acetoacetyl-CoA, 3-hydroxybutyryl-CoA, 3-HBal, 3-HB, 1,3-BDO, or a downstream product related thereto such as an ester or amide thereof, or a acetoacetyl-CoA, 3-hydroxybutyryl-CoA, 3-HBal, 3-HB, or 1,3-BDO pathway intermediate has a carbon-12, carbon-13, and carbon-14 isotope ratio of about the same value as the $CO_2$ that occurs in the environment. For example, in some aspects the invention provides bioderived acetoacetyl-CoA, 3-hydroxybutyryl-CoA, 3-HBal, 3-HB, 1,3-BDO, or a downstream product related thereto such as an ester or amide thereof, or a bioderived acetoacetyl-CoA, 3-hydroxybutyryl-CoA, 3-HBal, 3-HB, or 1,3-BDO intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived acetoacetyl-CoA, 3-hydroxybutyryl-CoA, 3-HBal, 3-HB, 1,3-BDO, or a downstream product related thereto such as an ester or amide thereof, or a bioderived acetoacetyl-CoA, 3-hydroxybutyryl-CoA, 3-HBal, 3-HB, or 1,3-BDO pathway intermediate as disclosed herein, wherein the bioderived product is chemically modified to generate a final product. Methods of chemically modifying a bioderived product of acetoacetyl-CoA, 3-hydroxybutyryl-CoA, 3-HBal, 3-HB, 1,3-BDO, or a downstream product related thereto such as an ester or amide thereof, or an intermediate of a acetoacetyl-CoA, 3-hydroxybutyryl-CoA, 3-HBal, 3-HB, or 1,3-BDO, to generate a desired product are well known to those skilled in the art, as described herein. In some embodiments, the invention further provides plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products, which can be based on acetoacetyl-CoA, 3-hydroxybutyryl-CoA, 3-HBal, and/or 1,3-BDO, or a downstream product related thereto such as an ester or amide thereof, having a carbon-12 versus carbon-13 versus carbon-14 isotope ratio of about the same value as the $CO_2$ that occurs in the environment, wherein the plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products are generated directly from or in combination with bioderived acetoacetyl-CoA, 3-hydroxybutyryl-CoA, 3-HBal, 3-HB, 1,3-BDO, or a downstream product related thereto such as an ester or amide thereof, or a bioderived acetoacetyl-CoA, 3-hydroxybutyryl-CoA, 3-HBal, 3-HB, or 1,3-BDO pathway intermediate as disclosed herein. For example, 1,3-BDO can be reacted with an acid, either in vivo or in vitro, to convert to an ester using, for example, a lipase. Such esters can have nutraceutical, medical and food uses, and are advantaged when the R-form of 1,3-butanediol is used since that is the form (compared to S-form or the racemic mixture that is made from petroleum or from ethanol by the acetaldehyde chemical synthesis route) best utilized by both animals and humans as an energy source (e.g. a ketone ester, such as (R)-3-hydroxybutyl-R-1,3-butanediol monoester (which has GRAS approval in the United States) and (R)-3-hydroxybutyrate glycerol monoester or diester). The ketone esters can be delivered orally, and the ester releases R-1,3-butanediol that is used by the body. See for example U.S. Patent Application US20150164855 entitled "Ketone Bodies and Ketone Body Esters for Maintaining or Improving Muscle Power Output." Thus the present invention is particularly useful to provide an improved enzymatic route and microorganism to provide an improved composition of 1,3-butanediol, namely R-1,3-butanediol, highly enriched or essentially enantiomerically pure, and further having improved purity qualities with respect to by-products. In some embodiment, the 1,3-butanediol is about or at least about 10%, 25%, 50%, 75%, 80%, 85%, 90%, 95%, 96%, 97%, 98%, 99%, or 100% R-1,3-butanediol (R-1,3-BDO).

1,3-Butanediol, also referred to as butylene glycol, has further food related uses including use directly as a food source, a food ingredient, a flavoring agent, a solvent or solubilizer for flavoring agents, a stabilizer, an emulsifier, and an anti-microbial agent and preservative. 1,3-Butanediol is used in the pharmaceutical industry as a parenteral drug solvent. 1,3-Butanediol finds use in cosmetics as an ingredient that is an emollient, a humectant, to prevent crystallization of insoluble ingredients, a solubilizer for less-water-soluble ingredients such as fragrances, and as an antimicrobial agent and preservative. For example, it can be used as a humectant, especially in hair sprays and setting lotions; it reduces loss of aromas from essential oils, preserves against spoilage by microorganisms, and is used as a solvent for benzoates. 1,3-Butanediol can be use at concentrations from 0.1 percent or less to 50 percent or greater. It is used in hair and bath products, eye and facial makeup, fragrances, personal cleanliness products, and shaving and skin care preparations. See for example the Cosmetic Ingredient Review board's report: "Final Report on the Safety Assessment of Butylene Glycol, Hexylene Glycol, Ethoxy diglycol, and Dipropylene Glycol", Journal of the American College of Toxicology, Volume 4, Number 5, 1985. This report, which is incorporated by reference, provides specific uses and concentrations of 1,3-butanediol (butylene glycol) in cosmetics; see for examples the report's Table 2 therein entitled "Product Formulation Data".

In some embodiments, the invention further provides a composition comprising bioderived acetoacetyl-CoA, 3-hydroxybutyryl-CoA, 3-HBal, 3-HB, 1,3-BDO, or a downstream product related thereto such as an ester or amide thereof, and a compound other than the bioderived acetoacetyl-CoA, 3-hydroxybutyryl-CoA, 3-HBal, 3-HB, 1,3-BDO, or a downstream product related thereto such as an ester or amide thereof. The compound other than the bioderived product can be a cellular portion, for example, a trace amount of a cellular portion of, or can be fermentation broth or culture medium or a purified or partially purified fraction thereof produced in the presence of, a non-naturally occurring cell of the invention having a pathway that produces acetoacetyl-CoA, 3-hydroxybutyryl-CoA, 3-HBal, 3-HB, 1,3-BDO, or a downstream product related thereto such as an ester or amide thereof. The composition can comprise, for example, a reduced level of a byproduct when produced by an organism having reduced byproduct formation, as disclosed herein. The composition can comprise, for example, bioderived acetoacetyl-CoA, 3-hydroxybutyryl-CoA, 3-HBal, 3-HB, 1,3-BDO, or a downstream product related thereto such as an ester or amide thereof, or a cell lysate or culture supernatant of a cell of the invention.

Acetoacetyl-CoA, 3-hydroxybutyryl-CoA, 3-HBal, 3-HB, 1,3-BDO, or a downstream product related thereto such as an ester or amide thereof, can be a chemical used in commercial and industrial applications. Non-limiting examples of such applications include production of plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products. Moreover, acetoacetyl-CoA, 3-hydroxybutyryl-CoA, 3-HBal, 3-HB, or 1,3-BDO can also be used as a raw material in the production of a wide range of products including plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products. Accordingly, in some embodiments, the invention provides biobased plastics, elastic fibers, polyurethanes, polyesters, including polyhydroxyalkanoates, nylons, organic solvents, polyurethane resins, polyester resins, hypoglycaemic agents, butadiene and/or butadiene-based products comprising one or more bioderived acetoacetyl-CoA, 3-hydroxybutyryl-CoA, 3-HBal, 3-HB, 1,3-BDO, or a downstream product related thereto such as an ester or amide thereof, or bioderived acetoacetyl-CoA, 3-hydroxybutyryl-CoA, 3-HBal, 3-HB, or 1,3-BDO pathway intermediate produced by a non-naturally occurring cell of the invention, for example, expressing a thiolase and/or a 3-hydroxybutyryl-CoA dehydrogenase of the invention, or produced using a method disclosed herein.

As used herein, the term "bioderived" means derived from or synthesized by a biological organism and can be considered a renewable resource since it can be generated by a biological organism. Such a biological organism, in particular the cells of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products comprising bioderived acetoacetyl-CoA, 3-hydroxybutyryl-CoA, 3-HBal, 3-HB, 1,3-BDO, or a downstream product related thereto such as an ester or amide thereof, or bioderived acetoacetyl-CoA, 3-hydroxybutyryl-CoA, 3-HBal, 3-HB, or 1,3-BDO pathway intermediate, wherein the bioderived acetoacetyl-CoA, 3-hydroxybutyryl-CoA, 3-HBal, 3-HB, 1,3-BDO, or a downstream product related thereto such as an ester or amide thereof, or bioderived acetoacetyl-CoA, 3-hydroxybutyryl-CoA, 3-HBal, 3-HB, or 1,3-BDO pathway intermediate includes all or part of the acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate used in the production of plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products. For example, the final plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products can contain the bioderived acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate, or a portion thereof that is the result of the manufacturing of plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products. Such manufacturing can include chemically reacting the bioderived acetoacetyl-CoA, 3-hydroxybutyryl-CoA, 3-HBal, 3-HB, 1,3-BDO, or a downstream product related thereto such as an ester or amide thereof, or bioderived acetoacetyl-CoA, 3-hydroxybutyryl-CoA, 3-HBal, 3-HB, or 1,3-BDO pathway intermediate (e.g. chemical conversion, chemical functionalization, chemical coupling, oxidation, reduction, polymerization, copolymerization and the like) with itself or another compound in a reaction to produce the final biobased product, such as the final plastics, elastic fibers, polyurethanes, polyesters, including polyhydroxyalkanoates, nylons, organic solvents, polyurethane resins, polyester resins, hypoglycaemic agents, butadiene and/or butadiene-based products. In some embodiments, particularly for those products formed by a polymerization process, the biobased product is comprised at least in part of the bioderived compound (e.g. 1,3-BDO) as a repeating unit. In some aspects, the invention provides a biobased products, such as plastics, elastic fibers, polyurethanes, polyesters, including polyhydroxyalkanoates, nylons, polyurethane resins, polyester resins, hypoglycaemic agents, cosmetic products, food additives, butadiene and/or butadiene-based products comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived acetoacetyl-CoA, 3-hydroxybutyryl-CoA, 3-HBal, 3-HB, 1,3-BDO, or a downstream product related thereto such as an ester or amide thereof, or bioderived acetoacetyl-CoA, 3-hydroxybutyryl-CoA, 3-HBal, 3-HB, or 1,3-BDO pathway intermediate as disclosed herein. In some embodiments, biobased products formed from bioderived compounds are subjected to a molding process to produce a molded product. It is understood that applicable methods for producing plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products can be readily adapted to utilize bioderived compounds described herein.

Additionally, in some embodiments, the invention provides a composition having a bioderived acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate disclosed herein and a compound other than the bioderived acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate. For example, in some aspects, the invention provides biobased plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products wherein the acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate used in its production is a combination of bioderived and petroleum derived acetoacetyl-CoA, 3-hydroxybutyryl-CoA, 3-HBal, 3-HB, 1,3-BDO, or a downstream product related thereto such as an ester or amide thereof, or acetoacetyl-CoA, 3-hydroxybutyryl-CoA, 3-HBal, 3-HB, or 1,3-BDO pathway intermediate. For example, biobased plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products can be produced using 50% bioderived acetoacetyl-CoA, 3-hydroxybutyryl-CoA, 3-HBal, 3-HB, 1,3-BDO, or a downstream product related thereto such as an ester or amide thereof, and 50% petroleum derived acetoacetyl-CoA, 3-hydroxybutyryl-CoA, 3-HBal, 3-HB, or 1,3-BDO, or a downstream product related thereto such as an ester or amide thereof, or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the cells disclosed herein. It is understood that applicable methods for producing plastics, elastic fibers, polyurethanes, polyesters, including polyhydroxyalkanoates, nylons, organic solvents, polyurethane resins, polyester resins, hypoglycaemic agents, cosmetic products, food additives, butadiene and/or butadiene-based products can be readily adapted to utilize bioderived compounds described herein.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of acetoacetyl-CoA, 3-hydroxybutyryl-CoA, 3-HBal, 3-HB, 1,3-BDO, or a downstream product related thereto such as an ester or amide thereof.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring cells for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host cells. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

The present disclosure provides 3-hydroxybutyryl-CoA dehydrogenase variants (see e.g., Examples). Examples for the generation of such variants are described. Any of a variety of methods can be used to generate a 3-hydroxybutyryl-CoA dehydrogenase variant such as the 3-hydroxybutyryl-CoA dehydrogenase variants disclosed herein. Such methods include, but are not limited to, site-directed mutagenesis, random mutagenesis, combinatorial libraries, and other mutagenesis methods described below (see e.g. Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999); Gillman et al., *Directed evolution library creation: Methods and Protocols* (*Methods in Molecular Biology*) Springer, $2^{nd}$ ed (2014)).

As disclosed herein, a nucleic acid encoding a desired activity of a pathway for acetoacetyl-CoA, 3-hydroxybutyryl-CoA, 3-HBal, 3-HB, 1,3-BDO, or a downstream product related thereto such as an ester or amide thereof, can be introduced into a host organism. In some cases, it can be desirable to modify an activity of a acetoacetyl-CoA, 3-hydroxybutyryl-CoA, 3-HBal, 3-HB, 1,3-BDO, or a downstream product related thereto such as an ester or amide thereof, pathway enzyme or protein to increase production of acetoacetyl-CoA, 3-hydroxybutyryl-CoA, 3-HBal, 3-HB, 1,3-BDO, or a downstream product related thereto such as an ester or amide thereof. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties.

Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a pathway enzyme or protein for producing acetoacetyl-CoA, 3-hydroxybutyryl-CoA, 3-HBal, 3-HB, 1,3-BDO, or a downstream product thereof such as an ester or amide thereof. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

Example 1: Generating 3-hydroxybutyryl-CoA Dehydrogenase Variants

This example describes generation of 3-hydroxybutyryl-CoA dehydrogenase variants with desirable properties.

Mutagenesis techniques were used to generate variant 3-hydroxybutyryl-CoA dehydrogenases based on a starting wild-type reference nucleic acid having nucleotide sequence SEQ ID NO: 1, encoding the 3-hydroxybutyryl-CoA dehydrogenase having the amino acid sequence of SEQ ID NO: 2:

(SEQ ID NO: 1)
atgactcagcgcattgcgtatgtgaccggcggcatgggtggtatcgga accgccatttgccagcggctggccaaggatggctttcgtgtggtggcc -continued

```
ggttgcggccccaactcgccgcgccgcgaaaagtggctggagcagcag aaggccctgggcttcgatttcattgcctcggaaggcaatgtggctgac tgggactcgaccaagaccgcattcgacaaggtcaagtccgaggtcggc gaggttgatgtgctgatcaacaacgccggtatcacccgcgacgtggtg ttccgcaagatgacccgcgccgactgggatgcggtgatcgacaccaac ctgacctcgctgttcaacgtcaccaagcaggtgatcgacggcatggcc gaccgtggctggggccgcatcgtcaacatctcgtcggtgaacgggcag aagggccagttcggccagaccaactactccaccgccaaggccggcctg catggcttcaccatggcactggcgcaggaagtggcgaccaagggcgtg accgtcaacacggtctctccgggctatatcgccaccgacatggtcaag gcgatccgccaggacgtgctcgacaagatcgtcgcgacgatcccggtc aagcgcctgggcctgccggaagagatcgcctcgatctgcgcctggttg tcgtcggaggagtccggtttctcgaccggcgccgacttctcgctcaac ggcggcctgcatatgggctga
```

(SEQ ID NO: 2)
MTQRIAYVTGGMGGIGTAICQRLAKDGFRVVAGCGPNSPRREKWLEQQ

KALGFDFIASEGNVADWDSTKTAFDKVKSEVGEVDVLINNAGITRDVV

FRKMTRADWDAVIDTNLTSLFNVTKQVIDGMADRGWGRIVNISSVNGQ

KGQFGQTNYSTAKAGLHGFTMALAQEVATKGVTVNTVSPGYIATDMVK

AIRQDVLDKIVATIPVKRLGLPEEIASICAWLSSEESGFSTGADFSLN

GGLHMG

Figure 3:
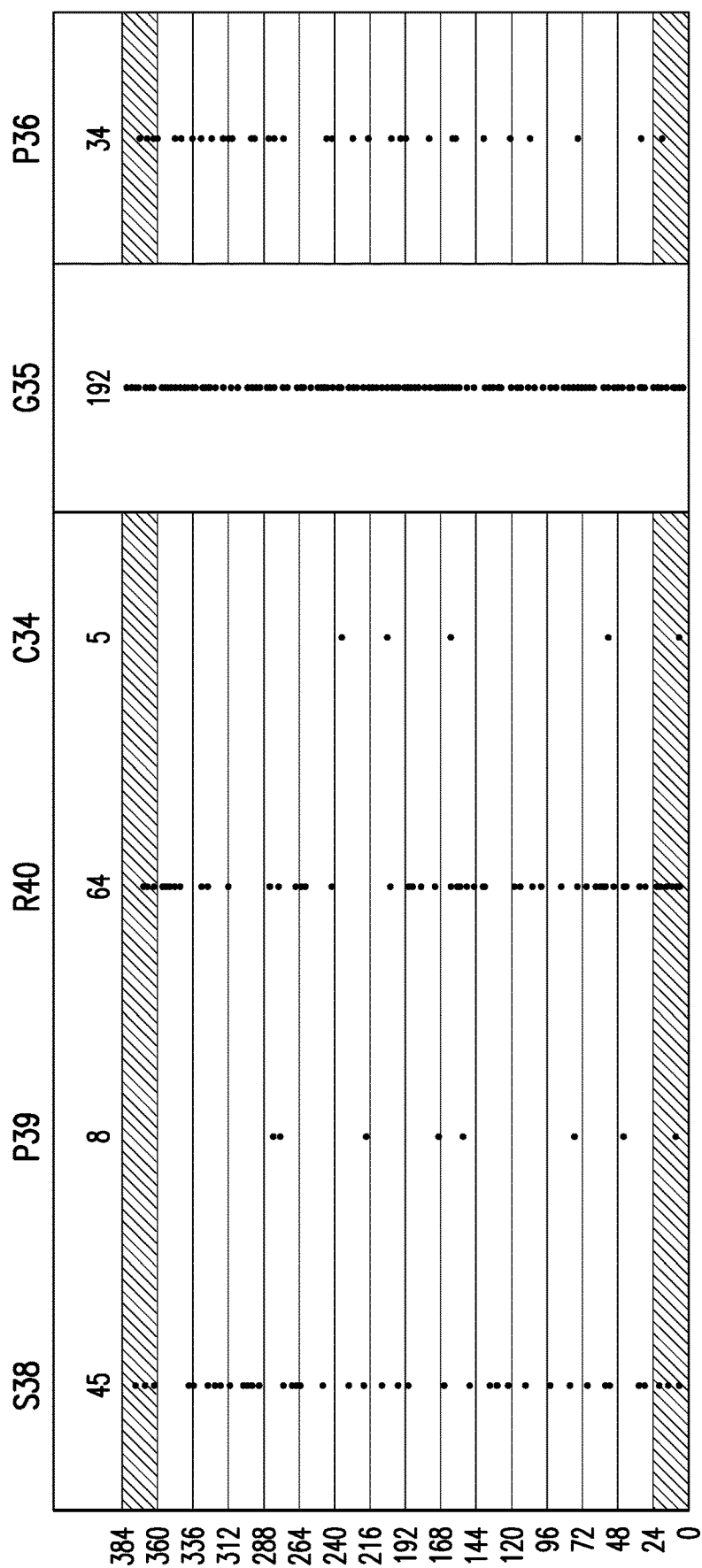
FIG. 3 illustrates the frequency of mutations at the indicated positions relative to SEQ ID NO: 2 among polypeptide variants having an increased ability to utilize NADH as a cofactor.

The 3-hydroxybutyryl-CoA dehydrogenase having SEQ ID NO: 2 is referred to in this example as the "reference enzyme," and is derived from the phaB gene from *Ralstonia eutropha* H16 chromosome, GenBank AM260479.1. The crystal structure of the reference enzyme in complex with an NADPH cofactor was analyzed to identify positions likely to affect cofactor specificity. FIG. 2 illustrates a portion of an example three-dimensional structure of the reference enzyme, including the relative positions of NADP and amino acids of the reference enzyme that are located near the NADP binding site. Residues G35, P36, $N_{37}$, S38, P39, and R40 were individually targeted for mutation. Mutations were made at each position individually using the degenerate codon NNK, representing 32 codons. Libraries were screened at 11× coverage for mutants having an increased ability to utilize NADH as a cofactor. In descending order, positions 35, 40, 38, and 36 showed the greatest number of hits among mutants having increased utilization of NADH. FIG. 3 provides an illustration of the frequency of mutations at the indicated positions among mutants having increased utilization of NADH identified in this screen. The high frequency of mutations at position G35 among variants having increased utilization of NADH was surprising because the crystal structure indicates that this residue interacts with the phosphate of NADP via an interaction with the backbone amine. Additional residues were also mutated, as indicated in Table 1.

Table 1 provides a list of mutants analyzed in these examples, and indicates which variants exhibited increased utilization of NADH relative to the reference enzyme (as indicated by increased specificity for NADH over NADPH), and which variants exhibited increased enzyme activity relative to variant AL. Variants in Table 1 are identified by an arbitrary identifier "1500x x" (where "xx" is a one- or two-letter designation), and each has a sequence that is identical to SEQ ID NO: 2, except for the indicated mutations. Where indicated, some mutations are mutations at the nucleic acid level that do not affect amino acid sequence (e.g., for variant 1500GH, in addition to the mutation G35E, the DNA coding sequence was subjected to codon optimization; for variant 1500GJ, the stop codon of the nucleic acid encoding variant 1500GH is changed to an amber stop). Amino acid substitutions were not identified for all variants in Table 1. For variant 1500EC, "G35*" indicates that glycine at position 35 was deleted. The reference enzyme was assigned identifiers 1500A, 1500B, and 1500C.

TABLE 1

| Identifier Name | ID No. | Mutation(s) | Increased NADH specificity vs reference enzyme | Increase rate vs AL |
|---|---|---|---|---|
| 1500A | 1 | reference enzyme (SEQ ID NO: 2) | | |
| 1500AA | 2 | C34Y, R40E, R41H | X | |
| 1500AB | 3 | C34Y, R40D | X | |
| 1500AC | 4 | G35K | X | |
| 1500AD | 5 | G35S, S38M, R40S | X | |
| 1500AE | 6 | G35M | X | |
| 1500AF | 7 | G35I, E78K | X | |
| 1500AG | 8 | G35I | | |
| 1500AH | 9 | G35Q | | |
| 1500AI | 10 | G35H | X | |
| 1500AJ | 11 | G35H, G90V | | |
| 1500AK | 12 | G35L | | |
| 1500AL | 13 | G35E | X | |
| 1500AM | 14 | N37K, S38, R40S, N112H, S115R | | |
| 1500AN | 15 | S38T, R40N | X | |
| 1500AO | 16 | S38T, R40A | X | |
| 1500AP | 17 | R40Q | X | |
| 1500AQ | 18 | R40E | X | |
| 1500AR | 19 | R40G | X | |
| 1500AS | 20 | S38Q, R40H | X | |
| 1500AU | 21 | S38Q, R40G | X | |
| 1500AV | 22 | S38E, R40T | X | |
| 1500AW | 23 | S38E, R40M | X | |
| 1500AX | 24 | S38E, R40I | X | |
| 1500AY | 25 | S38E, R40G | X | |
| 1500AZ | 26 | S38E, R40Y | X | |
| 1500B | 27 | reference enzyme (SEQ ID NO: 2) | | |
| 1500BA | 28 | S38E, R40S | X | |
| 1500BB | 29 | S38E, R40L | X | |
| 1500BC | 30 | S38E, R40F | X | |
| 1500BD | 31 | S38D, R40Q | | |
| 1500BE | 32 | S38D, R40H | X | |
| 1500BF | 33 | S38A, R40D | X | |
| 1500BG | 34 | S38Y, R40K | X | |
| 1500BH | 35 | S38Y | | |
| 1500BI | 36 | S38Y, R40I | X | |
| 1500BJ | 37 | S38Y, R40P | X | |
| 1500BK | 38 | S38Y, R40Y | X | |
| 1500BL | 39 | S38Y, R40S | X | |
| 1500BM | 40 | S38W, R40Q | X | |
| 1500BN | 41 | S38W, R40P | | |
| 1500BO | 42 | S38W, R40A | | |
| 1500BP | 43 | S38C, R40Q | X | |
| 1500BQ | 44 | S38F, R40A | X | |
| 1500BR | 45 | G35V | X | |
| 1500BS | 46 | G35Y | | |
| 1500BT | 47 | G35C | X | |
| 1500BU | 48 | G35L | X | |
| 1500BV | 49 | C34T, R40G | X | |
| 1500BW | 50 | T173S | | |
| 1500BX | 51 | Q47L | | |
| 1500BY | 52 | G35E, T173S | | |

TABLE 1-continued

| Identifier Name | ID No. | Mutation(s) | Increased NADH specificity vs reference enzyme | Increase rate vs AL |
|---|---|---|---|---|
| 1500BZ | 53 | G35E, Q47L | X | X |
| 1500C | 54 | reference enzyme (SEQ ID NO: 2) | | |
| 1500CA | 55 | S38E, R40S, T173S | | |
| 1500CB | 56 | S38E, R40S, Q47L | | |
| 1500CC | 57 | C345, G35E | X | |
| 1500CD | 58 | C34M, G35E | | |
| 1500CE | 59 | C34I, G35Y | X | |
| 1500CF | 60 | C34L, G35D | X | |
| 1500CG | 61 | C34E, G35T | X | |
| 1500CH | 62 | C34E, G35H | | |
| 1500CI | 63 | C34E, G35P | X | |
| 1500CJ | 64 | C34E, G35L | X | |
| 150OCK | 65 | C34E, G35E | | |
| 1500CL | 66 | C34E, G35L | X | |
| 1500CM | 67 | C34E, G35F | | |
| 1500CN | 68 | C34D, G35K | X | |
| 1500CO | 69 | C34D, G35T | X | |
| 1500CP | 70 | C34D, G35S | X | |
| 1500CQ | 71 | C34D, G35I | X | |
| 1500CR | 72 | C34D, G35V | X | |
| 1500CS | 73 | C34D, G35V | X | |
| 1500CT | 74 | C34D, G35Y | X | |
| 1500CU | 75 | C34V, G35E, P207Q | | |
| 1500CV | 76 | G35M, S38F | X | |
| 1500CW | 77 | G35I, S38F | X | |
| 1500CX | 78 | G35H, S38W | X | |
| 1500CY | 79 | G35P, S38W | X | |
| 1500CZ | 80 | G35P, R40F | X | |
| 1500D | 81 | C34T, R40N | X | |
| 1500DA | 82 | G35R, S38G | X | |
| 1500DB | 83 | G35L, R40E | X | |
| 1500DC | 84 | G35L, R40D, V203I | | |
| 1500DD | 85 | G35E, R40G, V203I | X | |
| 1500DE | 86 | G35E, R40G, A204T | | |
| 1500DF | 87 | G35E, R40S | X | |
| 1500DG | 88 | G35E, R40L | X | |
| 1500DH | 89 | G35E, S38L | X | |
| 1500DI | 90 | G35E, S38E | X | |
| 1500DJ | 91 | G35E, S38Y | X | |
| 1500DK | 92 | G35D, S38K | X | |
| 1500DL | 93 | G35D, S38E | X | |
| 1500DM | 94 | G35D, S38V | X | |
| 1500DN | 95 | G35A, S38Y | X | |
| 1500DO | 96 | S38T, R40Q | X | |
| 1500DP | 97 | S38T, R40Q | X | |
| 1500DQ | 98 | S38M, R40Q | X | |
| 1500DR | 99 | S38M, R40A | X | |
| 1500DS | 100 | S38I, R40V | X | |
| 1500DT | 101 | S38H, R40L | X | |
| 1500DU | 102 | S38E, R40S | X | |
| 1500DV | 103 | S38D, R40N | X | |
| 1500DW | 104 | S38Y, R40A | X | |
| 1500DX | 105 | S38Y, R40A | X | |
| 1500DY | 106 | S38C, R40A | X | |
| 1500DZ | 107 | G35V, S38E | X | |
| 1500E | 108 | C34T, R40T, L167Q | X | |
| 1500EA | 109 | G35V, S38E, R98C | X | |
| 1500EB | 110 | G35V, S38E, T205N | | |
| 1500EC | 111 | G35*, S38W | | |
| 1500ED | 112 | G35Y, R40E | X | |
| 1500EE | 113 | G35Y, S38Y | X | |
| 1500EF | 114 | G35Y, S38F | X | |
| 1500EG | 115 | G35C, S38E | X | |
| 1500EH | 116 | C34L, G35P | | |
| 1500EI | 117 | C34L, G35E | X | |
| 1500EJ | 118 | G35E, R40F | X | |
| 1500EK | 119 | C20F | | |
| 1500EL | 120 | C34T, G35E | X | |
| 1500EM | 121 | C34I, G35E | X | |
| 1500EN | 122 | C34L, G35E | X | |
| 1500EO | 123 | C34E, G35L, A107V | | |
| 1500EP | 124 | C34E, G35V | | |
| 1500EQ | 125 | C34D, G35L | X | |
| 1500ER | 126 | C34D, G35L | X | |
| 1500ES | 127 | C34A, G35E | | |
| 1500ET | 128 | G35P, S38E | X | |
| 1500EU | 129 | G35R, R40I | X | |
| 1500EV | 130 | G35E, R40A | X | |
| 1500EW | 131 | G35E, S38D | X | |
| 1500EX | 132 | G35A, S38Y | X | |
| 1500EY | 133 | G35A, S38E | X | |
| 1500EZ | 134 | S38M, R40D | X | |
| 1500F | 135 | C34T, R40T | X | |
| 1500FA | 136 | S38D, R40L | X | |
| 1500FB | 137 | G35E, V31I | | |
| 1500FC | 138 | G35E, P36S, L160M | | |
| 1500FD | 139 | G35E, E42Q | | |
| 1500FE | 140 | G35E, E46C | X | |
| 1500FF | 141 | G35E, E46S | | |
| 1500FG | 142 | G35E, F55I | X | |
| 1500FH | 143 | G35E, T92H | | |
| 1500FI | 144 | G35E, T92N | X | X |
| 1500FJ | 145 | G35E, A103M | | |
| 1500FK | 146 | G35E, D104Q | X | |
| 1500FL | 147 | G35E, D104A | X | X |
| 1500FM | 148 | G35E, D104E | X | X |
| 1500FN | 149 | G35E, D106H, T114C | X | X |
| 1500FO | 150 | G35E, N112C | X | X |
| 1500FP | 151 | G35E, N112D | X | X |
| 1500FQ | 152 | G35E, D129E | X | X |
| 1500FR | 153 | G35E, T155C | X | X |
| 1500FS | 154 | G35E, A156S | X | X |
| 1500FT | 155 | G35E, A158R | | |
| 1500FU | 156 | G35E, A193R | X | |
| 1500FV | 157 | G35E, T205Q | X | |
| 1500FW | 158 | G35E, K209Q | X | X |
| 1500FX | 159 | G35E, L213N, Q144Q, Q48Q | | |
| 1500FY | 160 | G35E, E215W | X | |
| 1500FZ | 161 | G35E, E215H | X | |
| 1500G | 162 | C34T; R40D | X | |
| 1500GA | 163 | G35E, D236C | X | |
| 1500GB | 164 | G35E, D236V | | |
| 1500GC | 165 | G35E, G241G | | |
| 1500GD | 166 | G35E, L243A | X | X |
| 1500GE | 167 | G35E, L243I | X | X |
| 1500GF | 168 | G35E, L243V | X | X |
| 1500GG | 169 | G35E, L160A | X | |
| 1500H | 170 | C34T; R40G | X | |
| 1500I | 171 | C34T; R40G | X | |
| 1500J | 172 | C34T, R40Q | X | |
| 1500K | 173 | C34T, R40D | X | |
| 1500L | 174 | C34T, R40G | X | |
| 1500M | 175 | C34T, R40G | X | |
| 1500N | 176 | C34T, R40F | | |
| 1500O | 177 | C34I, R40N | X | |
| 1500P | 178 | C34I, R40L | X | |
| 1500Q | 179 | C34I, R40G | | |
| 1500R | 180 | C34H, R40E | X | |
| 1500S | 181 | C34H, R40D | X | |
| 1500T | 182 | C34H, R40G | X | |
| 1500U | 183 | C34V, R40G | X | |
| 1500V | 184 | C34V, R40G | X | |
| 1500W | 185 | C34V, R40T | X | |
| 1500X | 186 | C34V, R40G | X | |
| 1500Y | 187 | C34Y, R40N | X | |
| 1500Z | 188 | C34Y, R40S, R41H | X | |

For comparison, a sequence homology search was conducted to identify enzymes homologous to the reference enzyme. Example results of homologous enzymes are provided in Table 2. Homologous enzymes are identified by GenBank ID number, the source organism is identified, and positions corresponding to residues C34, G35, P36, $N_{37}$, S38, P39, and R40 of SEQ ID NO: 2 are indicated.

TABLE 2

| GenBank ID | Organism | % Identity | C34 | G35 | P36 | N37 | S38 | P39 | R40 |
|---|---|---|---|---|---|---|---|---|---|
| CCF95918 | Ralstonia solanacearum K60-1 | 92.68 | C34 | G35 | P36 | N37 | S38 | P39 | R40 |
| SAL82526 | Caballeronia choical | 79.27 | C34 | G35 | P36 | N37 | S38 | P39 | R40 |
| WP_009606749 | Xanthamonas translucens | 65.45 | C34 | G35 | P36 | N37 | S38 | P39 | R40 |
| AGN95877 | Cupriavidus necator | 60.82 | C34 | G35 | P36 | R37 | S38 | S39 | R40 |
| AAB65780 | Alcaligenes sp. SH69 | 67.48 | C34 | G35 | P36 | T37 | R38 | D39 | H40 |
| ETH84293 | Bordetella pertussis STO1-CHOC-0017 | 74.65 | C5 | G6 | P7 | S8 | R9 | N10 | Y40 |
| SAK89949 | Burkholderia arationis | 84.26 | C23 | G24 | P25 | S26 | R27 | N28 | Y29 |
| AMP00485 | Collimonas arenae | 81.11 | C5 | G6 | P7 | N8 | S9 | T10 | R11 |

In some embodiments, the disclosure provides isolated polypeptide variants comprising a sequence having at least 50%, 65%, 70%, 75%, 80%, 85%, 90%, 95%, 98%, or 99% identity to SEQ ID NO: 2 or a polypeptide variant selected from Table 1, and (b) the polypeptide variant comprises 1, 2, 3, 4, 5, or more amino acid substitutions relative to SEQ ID NO: 2 selected from: A103M, A107V, A156S, A158R, A193R, A204T, C20F, C34A, C34D, C34E, C34H, C34I, C34L, C34M, C34S, C34T, C34V, C34Y, D104A, D104E, D104Q, D106H, D129E, D236C, D236V, E215H, E215W, E42Q, E46C, E46S, E78K, F55I, G241G, G35*, G35A, G35C, G35D, G35E, G35F, G35H, G35I, G35K, G35L, G35M, G35P, G35Q, G35R, G35S, G35T, G35V, G35Y, G90V, K209Q, L160A, L160M, L167Q, L213N, L243A, L243I, L243V, $N_{112}C$, $N_{112}D$, $N_{112}H$, $N_{37}K$, P207Q, P36S, Q144Q, Q47L, Q47L, Q48Q, R40A, R40D, R40E, R40F, R40G, R40H, R40I, R40K, R40L, R40M, R40N, R40P, R40Q, R40S, R40T, R40V, R40Y, R41H, R98C, S115R, S38A, S38C, S38D, S38E, S38F, S38G, S38H, S38I, S38K, S38L, S38M, S38Q, S38T, S38V, S38W, S38Y, T114C, T155C, T173S, T205N, T205Q, T92H, T92N, V203I, V31I, and corresponding amino acid substitution(s) in homologous proteins.

Example 2: Activities of 3-hydroxybutyryl-CoA Dehydrogenase Variants

Variants selected from among those listed in Table 1 were subjected to assays for enzyme activity. Assays were conducted using lysates prepared from E. coli cells expressing 3-hydroxybutyryl-CoA dehydrogenase variants. Lysates were prepared using detergent based reagent (Bugbuster). Assay buffer contained 5 mM $KH_2PO_4$, 20 mM $K_2HPO_4$, 0.15 M KCl, and 10 mM sodium glutamate, pH 7.5. Activity on 100 μM acetoacetyl-CoA and either 500 NADH or 500 μM NADPH was monitored via absorbance changes at 340 nm. Rates were determined from the slope of the line of at least five data points within the first order rate.

Figure 4:
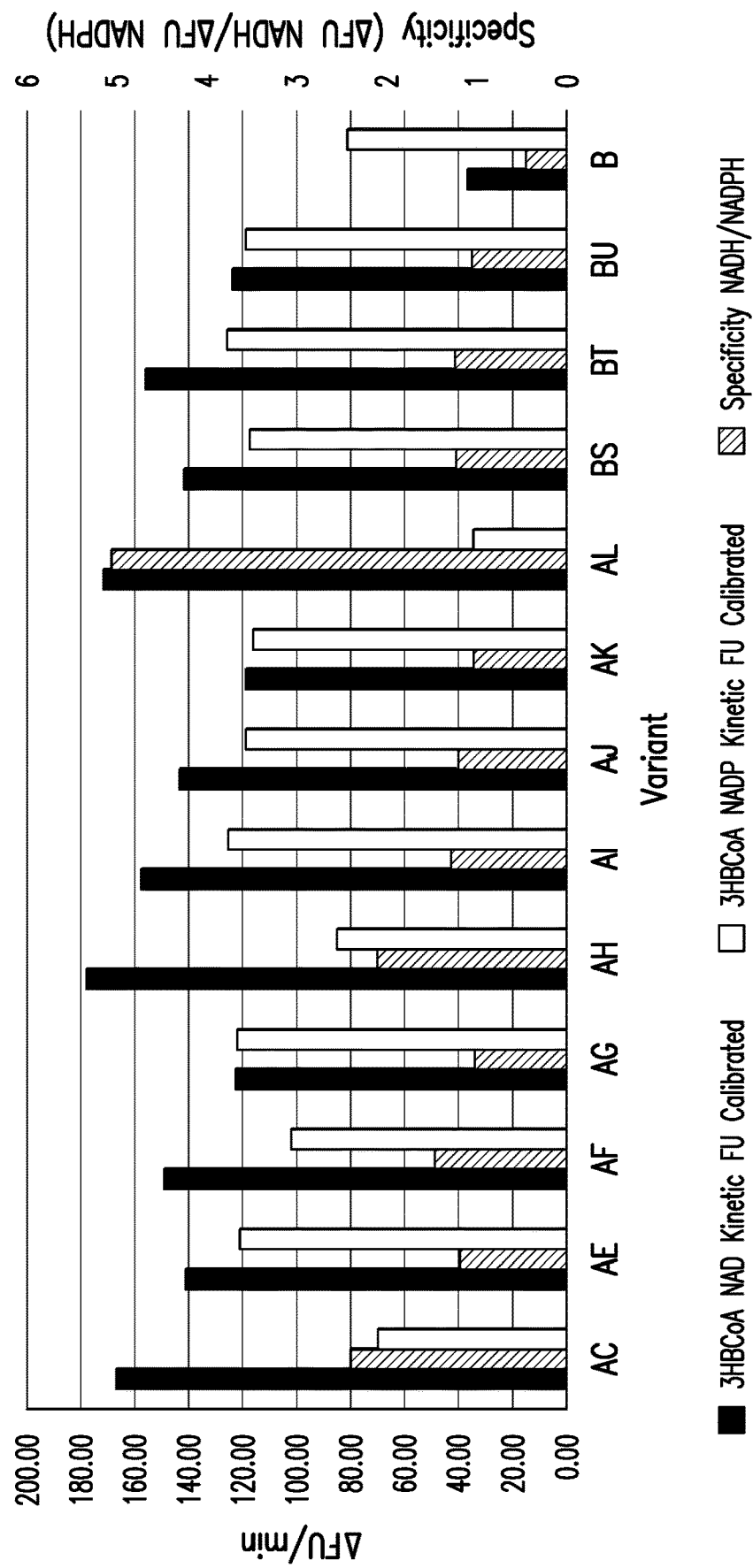
FIGS. 4-6 illustrate example results of an activity assay of the indicated variants when using either NADH or NADPH as the co-factor.

FIG. 4 illustrates example results of the activity assays of the indicated variants when using either NADH or NADPH as the co-factor. Also illustrated is the ratio of activity when using NADH to activity when using NADPH (expressed as "NADH/NADPH"), which is used as a measure of specificity for NADH. Variants are identified in FIG. 4 by their one- or two-letter designation, omitting the preceding "1500" designation. Thus, the reference enzyme is indentified as "B," indicating the identifier 1500B. All of the variants exhibited increased activity utilizing NADH relative to the reference enzyme, and increased NADH specificity. One variant in particular, 1500AL (having a G35E mutation, relative to SEQ ID NO: 2), exhibited both a significantly decreased activity using NADPH and a significantly increased activity using NADH, yielding a substantially increased specificity for use of NADH as the cofactor.

Figure 5:
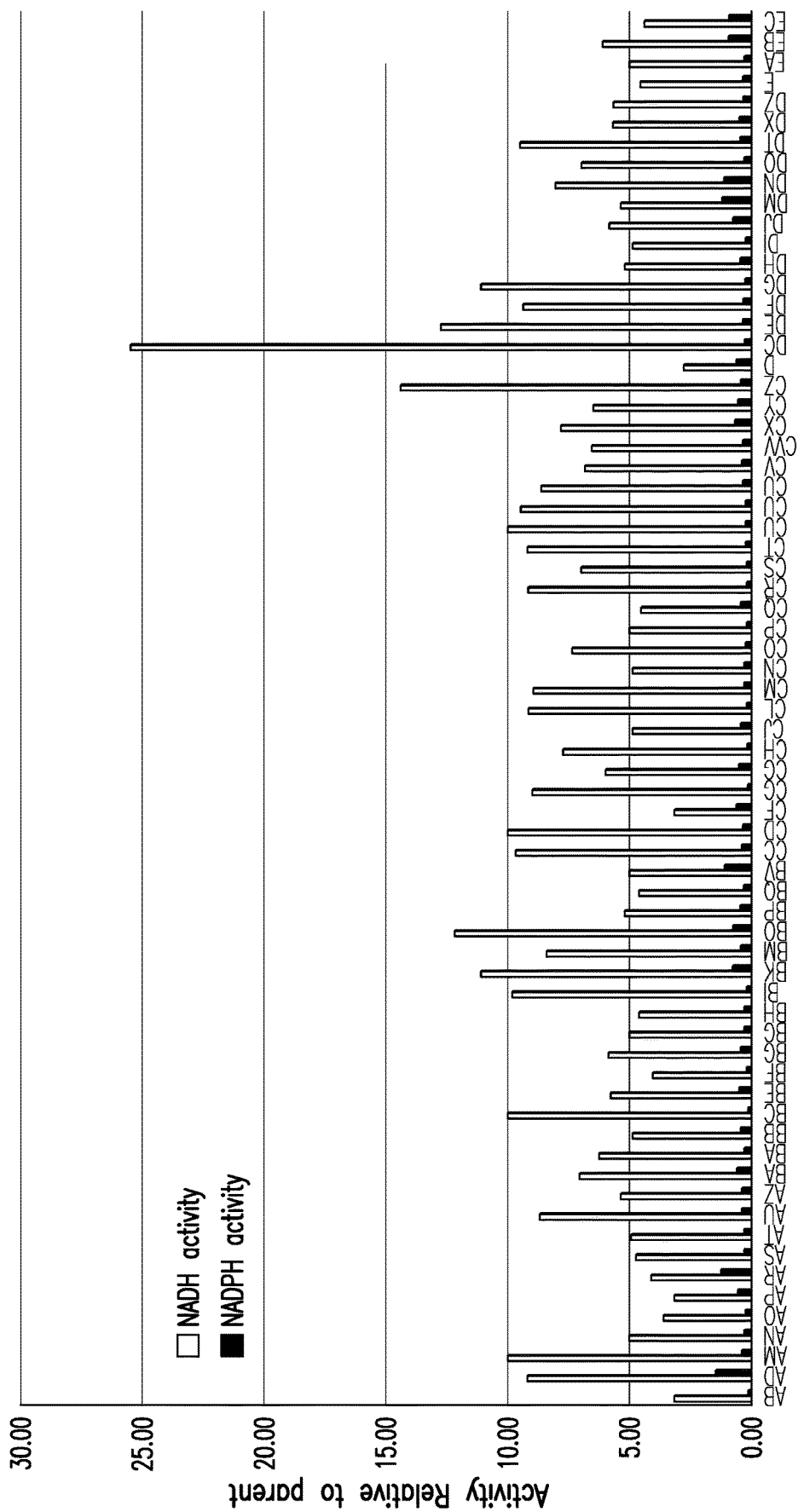

FIG. 5 illustrates further example results of the activity assays of the indicated variants when using either NADH or NADPH as the co-factor. These variants contained mutations in two residues selected from C34, G35, P36, $N_{37}$, and S38. Enzyme activities for reactions using either NADH or NADPH as the cofactor are expressed as a fold change with respect to the reference enzyme. Variants are identified in FIG. 5 by their two-letter designation, omitting the preceding "1500" designation.

Figure 6:
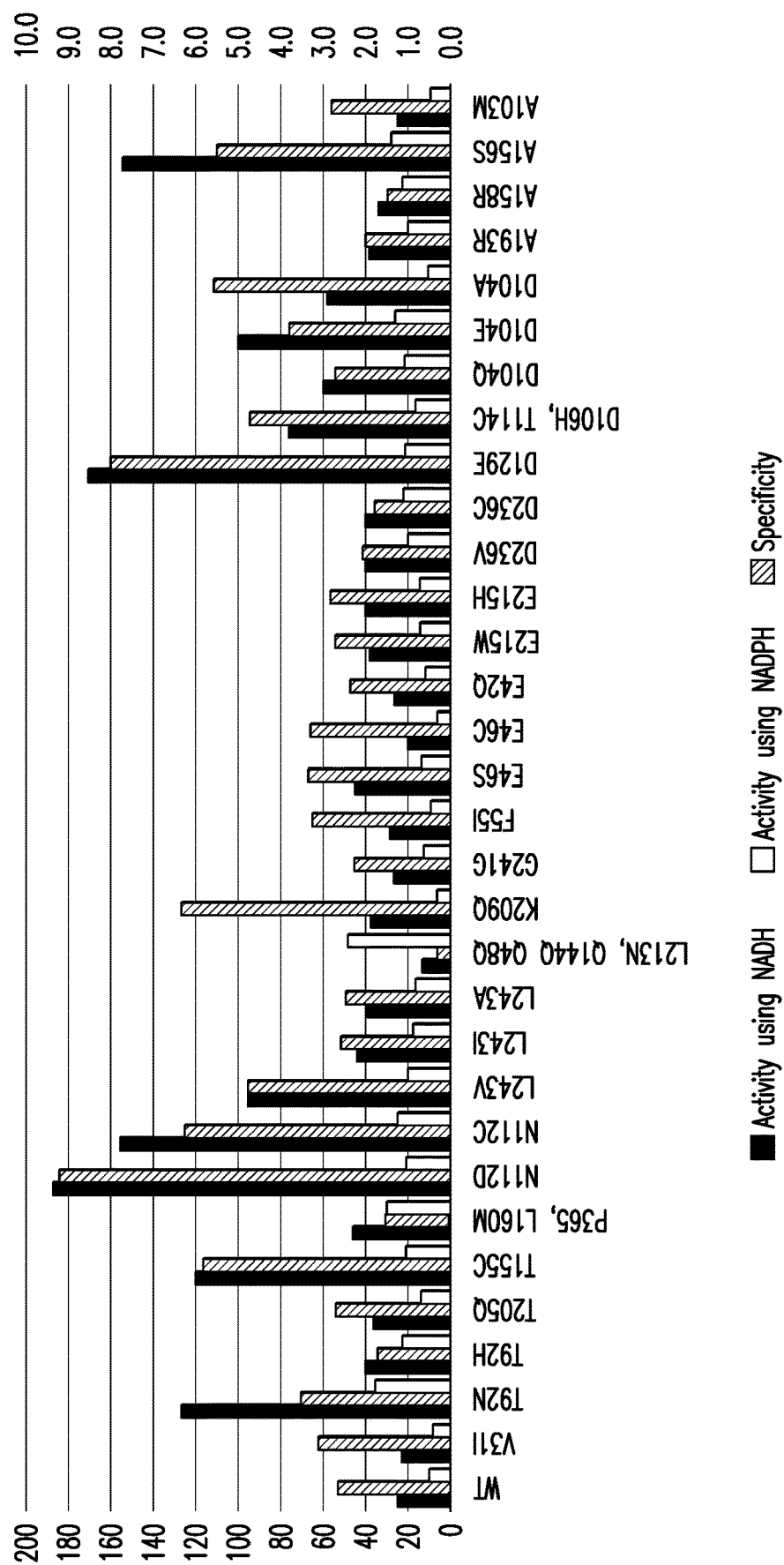

Variant 1500AL was selected as a parent enzyme for further mutagenesis. Mutations were again made at positions 30-34 and 36 (holding G35E constant), using a degenerate codon to produce libraries of variants. Activities of the resulting variants were assayed using either NADH or NADPH as the co-factor, as described above. Example results are illustrated in FIG. 6, which reports the enzyme activities as well as the NADH specificity. Variant 1500AL is designated as "WT," and has the amino acid sequence of SEQ ID NO: 2 except for the G35E mutation. All other variants in FIG. 6 are identified by the one or more other mutations relative to SEQ ID NO: 2, in addition to the shared G35E mutation. Corresponding variants are presented in Table 1 (see e.g., 1500FB for mutations G35E, V31I, which is identified in FIG. 6 as simply "V31I").

Example 3: 3-hydroxybutyryl-CoA Dehydrogenase Variants and 1,3-BDO

Selected variants from Example 1 were assayed for their effects on production of various metabolites, including 1,3-BDO, in cells comprising a 1,3-BDO pathway. 3-hydroxybutyryl-CoA dehydrogenase variants were expressed in cells harboring a heterologous pathway for production of 1,3-BDO and compared to a reference strain that was identical, except for expression of a reference 3-hydroxybutyryl-CoA dehydrogenase having the sequence of SEQ ID NO: 2 instead of the variant. Cells were grown in minimal media under microaerobic conditions. Production in the media of 1,3-BDO and the byproducts 3-HB, 4-hydroxy-2-butanone (4-OH 2-butanone), pyruvate (pyr), acetate (ace), and ethanol (EtOH) was measured by liquid chromatography mass spectrometry.

Results for assays of metabolites produced by cells comprising the reference enzyme having amino acid sequence SEQ ID NO: 2 (1500C), variant 1500AL, variant 1500AI, variant 1500BA, or variant 1500BV are provided in Table 3. Production of 1,3-BDO was increased in all of the variants relative to the reference enzyme, nearly 10-fold in the case of 1500AL.

TABLE 3

| | | | | | |
|---|---|---|---|---|---|
| [Ace] | 0.58 ± | 1.33 ± | 2.38 ± | 1.35 ± | 0 ± |
| [Pyr] | 0.58 ± | 8.92 ± | 3.12 ± | 8.69 ± | 8.46 ± |
| [1,3-BDO] | 2.67 ± 2.42 | 24.2 ± 1.98 | 10.53 ± 0.53 | 21.8 ± 2.6 | 23.2 ± 1.12 |
| [3HB] | 0.22 ± 0.25 | 1.41 ± 0.1 | 0.74 ± 0.04 | 1.21 ± 0.04 | 1.31 ± 0.17 |
| [4-OH-2-butanone] | 0.66 ± 0.48 | 1.79 ± 0.14 | 1.67 ± 0.11 | 2.52 ± 0.39 | 1.83 ± 0.13 |
| [EtOH] | NaN ± | 3.31 ± | 1.85 ± | 4.19 ± | 2.65 ± |
| Identifier | 1500C | 1500AL | 1500AI | 1500BA | 1500BV |

Example 4: Thiolase with Improved 1,3-BDO Production

Two thiolases were compared along multiple metrics with regard to 1,3-BDO production. The two thiolases were the acetoacetyl-CoA thiolase of *Ralstonia eutropha* ("Re-thiolase"), encoded by the polynucleotide sequence of SEQ ID NO: 3 and having the amino acid serquence of SEQ ID NO: 4, and the acetoacetyl-CoA thiolase of *Clostridium acetobutylicum* ("Ca-thiolase"), encoded by the polynucleotide sequence of SEQ ID NO: 5 and having the amino acid sequence of SEQ ID NO: 6. The sequences are listed below:

(SEQ ID NO: 3)
atgactgacgttgtcatcgtatccgccgcccgcaccgcggtcggcaag tttggcggctcgctggccaagatcccggcaccggaactgggtgccgtg gtcatcaaggccgcgctggagcgcgccggcgtcaagccggagcaggtg agcgaagtcatcatgggccaggtgctgaccgccggttcgggccagaac cccgcacgccaggccgcgatcaaggccggcctgccggcgatggtgccg gccatgaccatcaacaaggtgtgcggctcgggcctgaaggccgtgatg ctggccgccaacgcgatcatggcgggcgacgccgagatcgtggtggcc ggcggccaggaaaacatgagcgccgccccgcacgtgctgccgggctcg cgcgatggtttccgcatgggcgatgccaagctggtcgacaccatgatc gtcgacggcctgtgggacgtgtacaaccagtaccacatgggcatcacc gccgagaacgtggccaaggaatacggcatcacacgcgaggcgcaggat gagttcgccgtcggctcgcagaacaaggccgaagccgcgcagaaggcc ggcaagtttgacgaagagatcgtcccggtgctgatcccgcagcgcaag ggcgacccggtggccttcaagaccgacgagttcgtgcgccagggcgcc acgctggacagcatgtccggcctcaagcccgccttcgacaaggccggc acggtgaccgcggccaacgcctcgggcctgaacgacggcgccgccgcg gtggtggtgatgtcggcggccaaggccaaggaactgggcctgaccccg ctggccacgatcaagagctatgccaacgccggtgtcgatcccaaggtg atgggcatgggcccggtgccggcctccaagcgcgccctgtcgcgcgcc gagtggaccccgcaagacctggacctgatggagatcaacgaggcctt gccgcgcaggcgctggcggtgcaccagcagatgggctgggacacctcc aaggtcaatgtgaacggcggcgccatcgccatcggccacccgatcggc gcgtcgggctgccgtatcctggtgacgctgctgcacgagatgaagcgc cgtgacgcgaagaagggcctggcctcgctgtgcatcggcggcggcatg ggcgtggcgctggcagtcgagcgcaaataa (SEQ ID NO: 4)
MTDVVIVSAARTAVGKFGGSLAKIPAPELGAVVIKAALERAGVKPEQV

SEVIMGQVLTAGSGQNPARQAAIKAGLPAMVPAMTINKVCGSGLKAVM

LAANAIMAGDAEIVVAGGQENMSAAPHVLPGSRDGFRMGDAKLVDTMI

VDGLWDVYNQYHMGITAENVAKEYGITREAQDEFAVGSQNKAEAAQKA

GKFDEEIVPVLIPQRKGDPVAFKTDEFVRQGATLDSMSGLKPAFDKAG

TVTAANASGLNDGAAAVVVMSAAKAKELGLTPLATIKSYANAGVDPKV

MGMGPVPASKRALSRAEWTPQDLDLMEINEAFAAQALAVHQQMGWDTS

KVNVNGGAIAIGHPIGASGCRILVTLLHEMKRRDAKKGLASLCIGGGM

GVALAVERK (SEQ ID NO: 5)
atgagagatgtagtaatagtaagtgctgtaagaactgcaataggagca tatggaaaaacattaaaggatgtacctgcaacagagttaggagctata gtaataaaggaagctgtaagaagagctaatataaatccaaatgagatt aatgaagttattttggaaatgtacttcaagctggattaggccaaaac ccagcaagacaagcagcagtaaaagcaggattaccttagaaacacct gcgtttacaatcaataaggtttgtggttcaggtttaagatctataagt ttagcagctcaaattataaaagctggagatgctgataccattgtagta ggtggtatggaaaatatgtctagatcaccatatttgattaacaatcag agatggggtcaaagaatgggagatagtgaattagttgatgaaatgata aaggatggtttgtgggatgcatttaatggatatcatatgggagtaact gcagaaaatattgcagaacaatggaatataacaagagaagagcaagat gaattttcacttatgtcacaacaaaaagctgaaaaagccattaaaaat ggagaatttaaggatgaaatagttcctgtattaataaagactaaaaaa ggtgaaatagtctttgatcaagatgaatttcctagattcggaaacact attgaagcattaagaaaacttaaacctattttcaaggaaaatggtact gttacagcaggtaatgcatccggattaaatgatggagctgcagcacta gtaataatgagcgctgataaagctaacgctctcggaataaaaccacttt gctaagattacttcttacggatcatatggggtagatccatcaataatg ggatatggagctttttatgcaactaaagctgccttagataaaattaat ttaaaacctgaagacttagatttaattgaagctaacgaggcatatgct tctcaaagtatagcagtaactagagatttaaatttagatatgagtaaa -continued

```
gttaatgttaatggtggagctatagcacttggacatccaataggtgca tctggtgcacgtattttagtaacattactatacgctatgcaaaaaaga gattcaaaaaaaggtcttgctactctatgtattggtggaggtcaggga acagctctcgtagttgaaagagactaa
```

(SEQ ID NO: 6)
MRDVVIVSAVRTAIGAYGKTLKDVPATELGAIVIKEAVRRANINPNEI

NEVIFGNVLQAGLGQNPARQAAVKAGLPLETPAFTINKVCGSGLRSIS

LAAQIIKAGDADTIVVGGMENMSRSPYLINNQRWGQRMGDSELVDEMI

KDGLWDAFNGYHMGVTAENIAEQWNITREEQDEFSLMSQQKAEKAIKN

GEFKDEIVPVLIKTKKGEIVFDQDEFPRFGNTIEALRKLKPIFKENGT

VTAGNASGLNDGAAALVIMSADKANALGIKPLAKITSYGSYGVDPSIM

GYGAFYATKAALDKINLKPEDLDLIEANEAYASQSIAVTRDLNLDMSK

VNVNGGAIALGHPIGASGARILVTLLYAMQKRDSKKGLATLCIGGGQG

TALVVERD

Figure 7A:
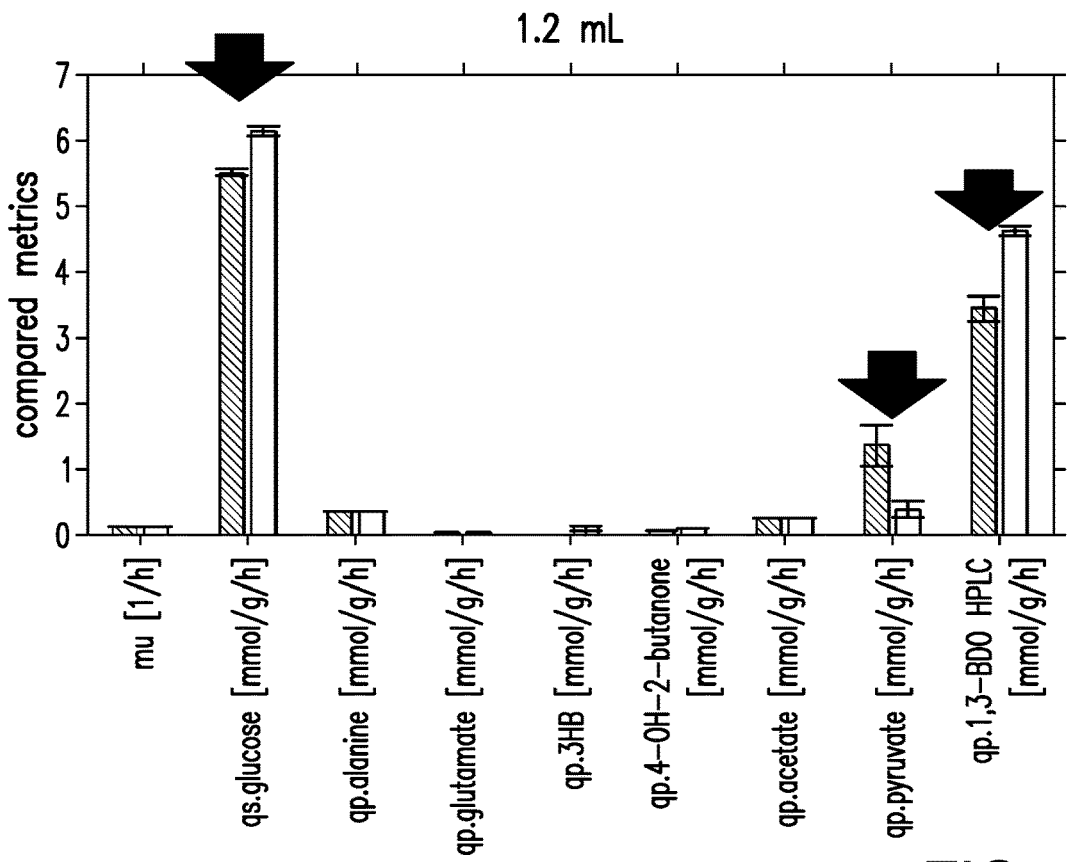
FIGS. 7A-C illustrate example results for two strains across multiple metrics for each of three culture volumes.
Figure 7B:
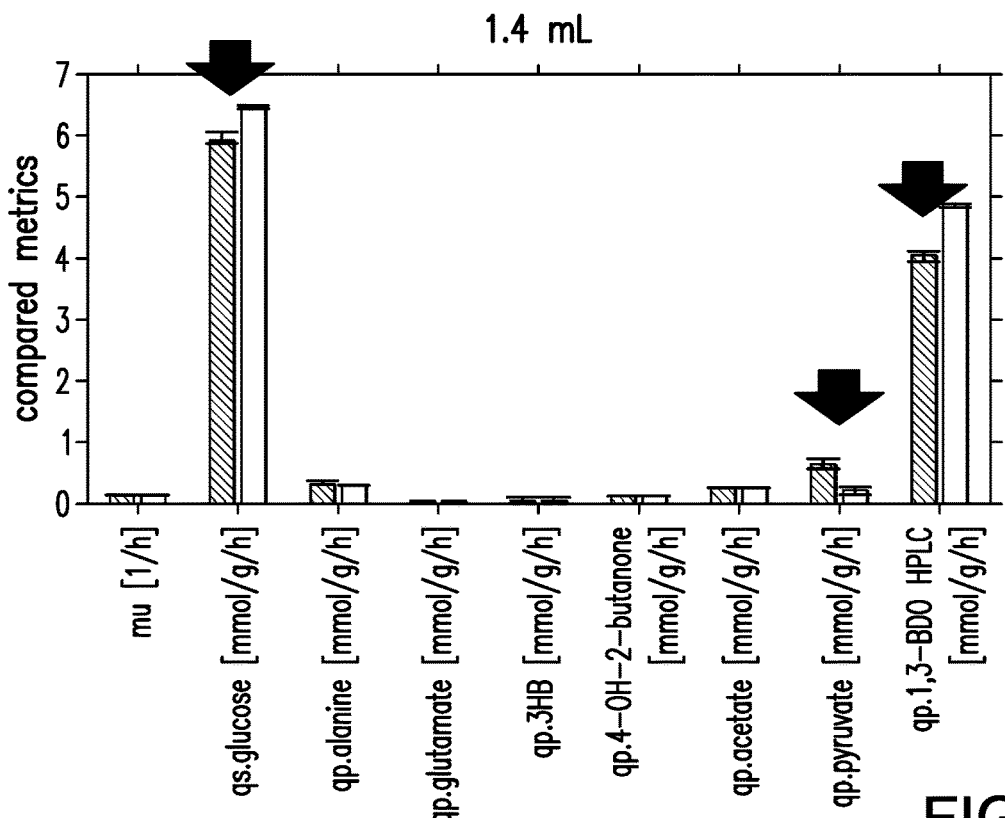
Figure 7C:
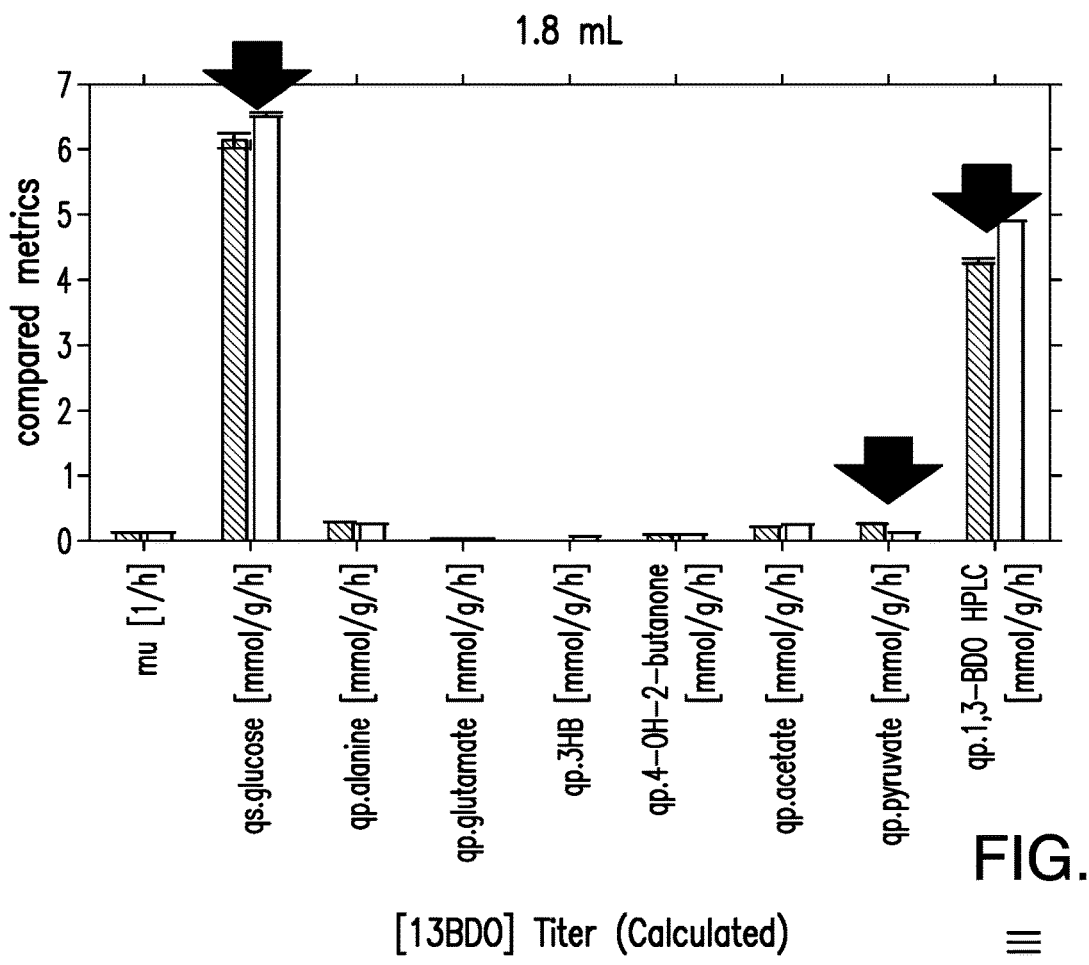

An *E. coli* strain having a 1,3-BDO pathway was engineered to express either Re-thiolase ("Strain 1" in this example) or Ca-thiolase ("Strain 2" in this example). The strains were cultured under microaerobic conditions at three different culture volumes. FIGS. 7A-C illustrate results for the two strains across multiple metrics for each of the three culture volumes. In each pair of bars, results for the strain with the Ca-thiolase are on the left, and results for the strain with the Re-thiolase are on the right. Results indicated that Strain 1 produced significantly less pyruvate and more 1,3-BDO than Strain 2.

Example 5: Improved Thiolase at Different Aeration Levels

Figure 8A:
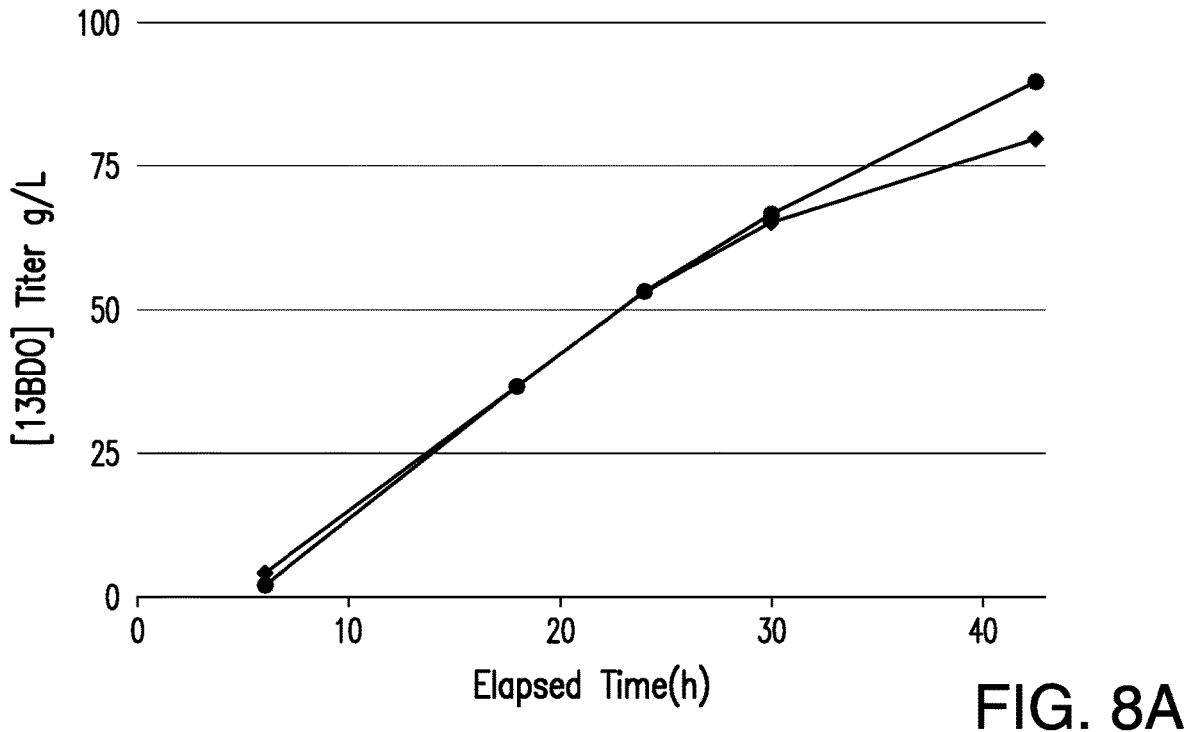
FIGS. 8A-F illustrate examples of 1,3-BDO titer, productivity, and yield for wOUR 25 (FIGS. 8A-C) and wOUR 30 (FIGS. 8D-F).
Figure 8B:
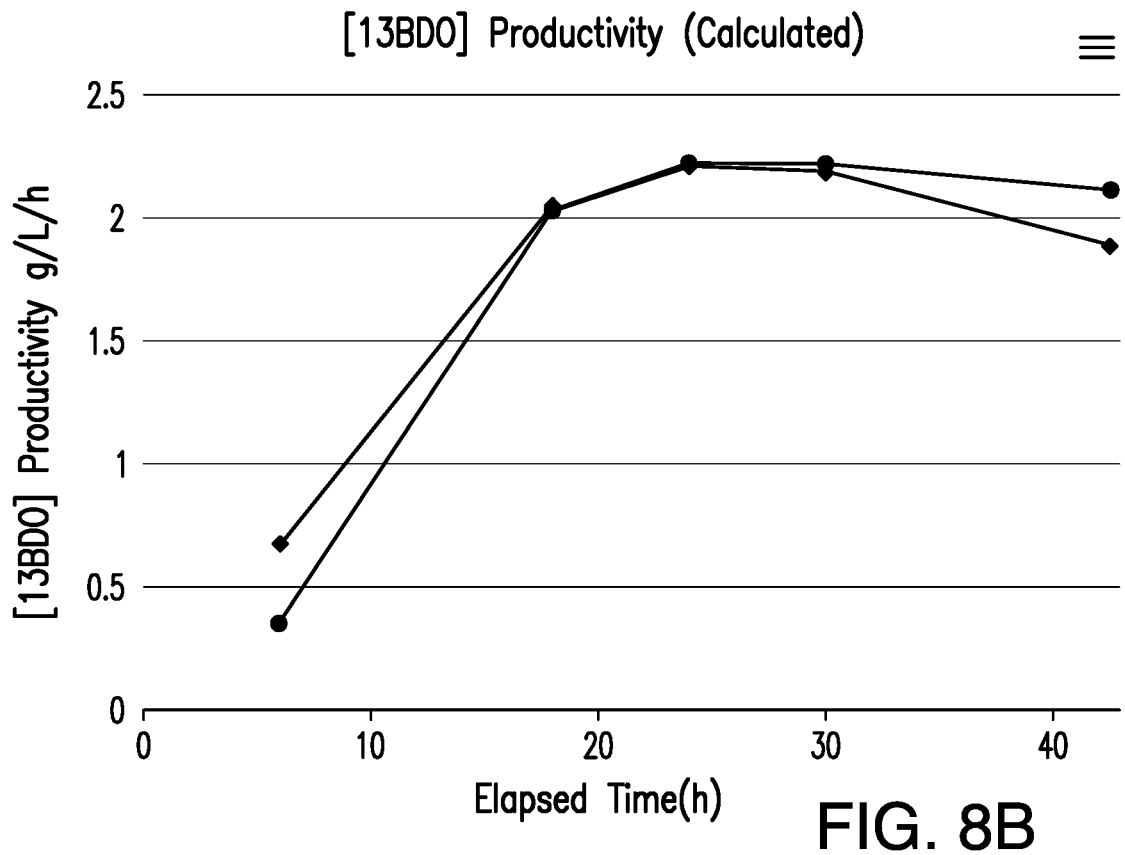
Figure 8C:
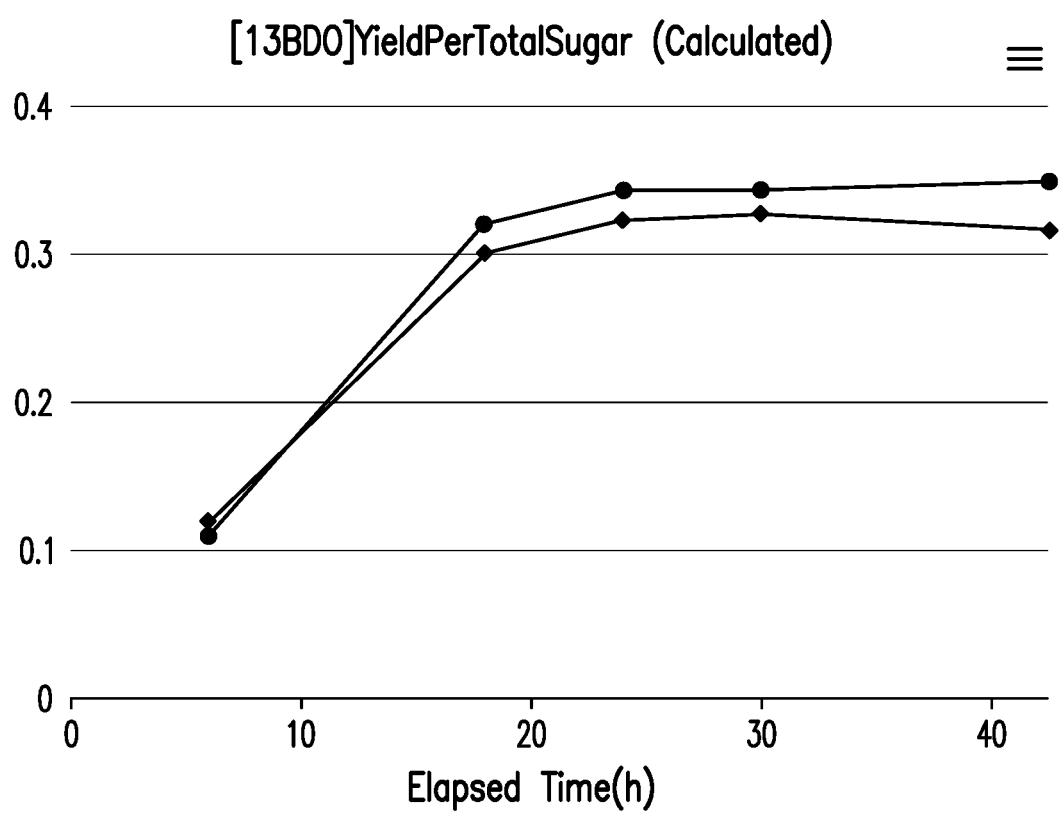
Figure 8D:
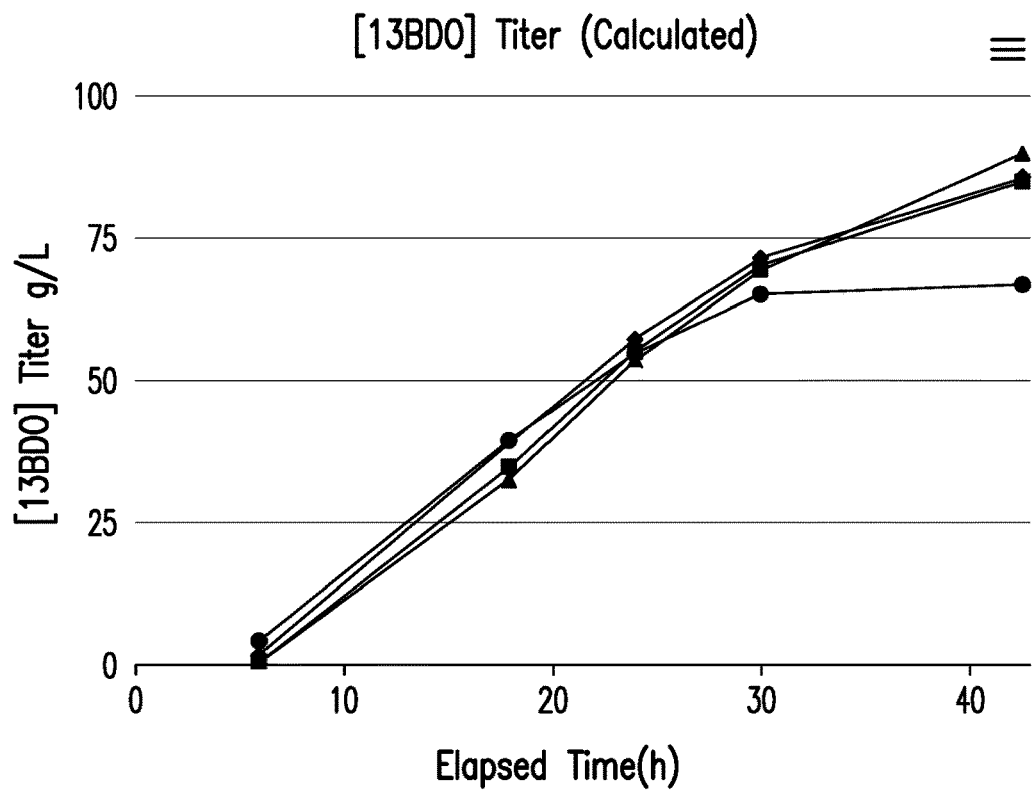
Figure 8E:
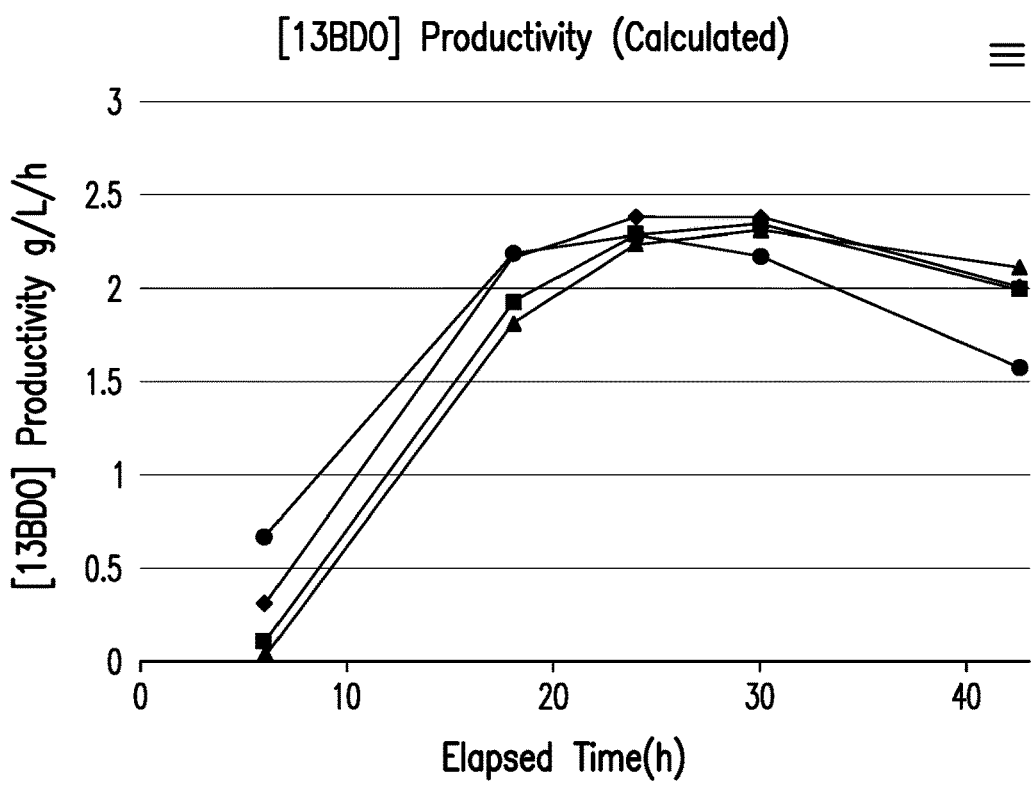
Figure 8F:
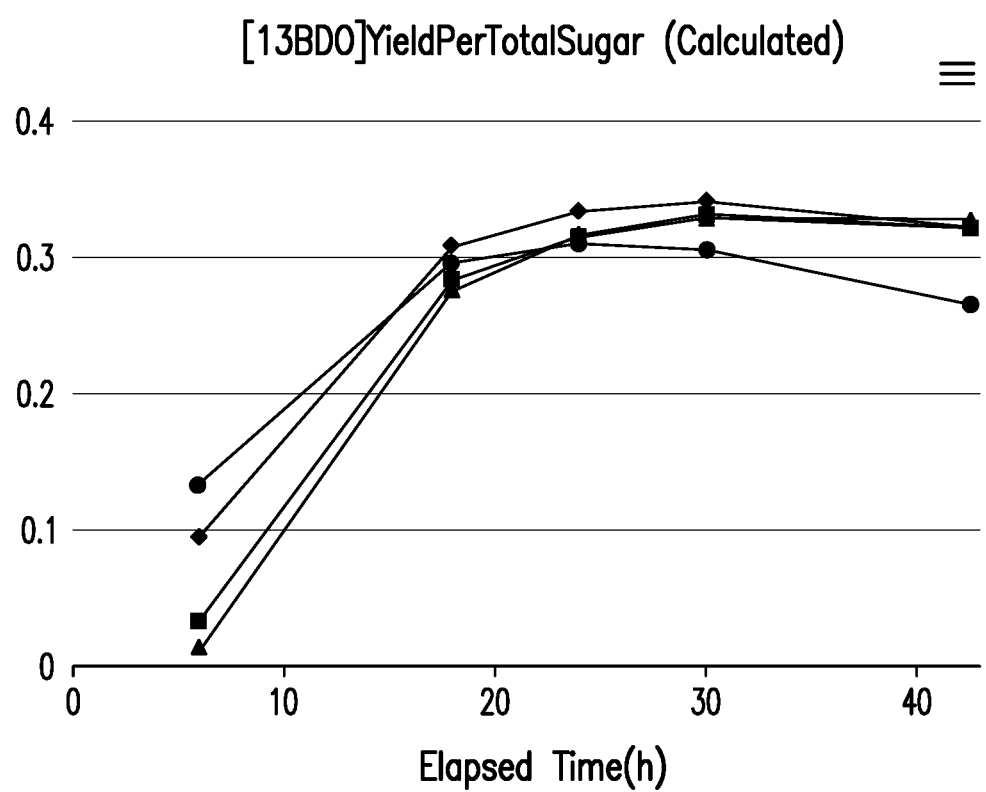

Strain 1 and Strain 2 from Example 4 were cultured under two different aeration conditions, wOUR 30 (higher aearation) and wOUR 25 (lower aeration), and were characterized with respect to the effects of Re-thiolase on metabolite profiles, as compared to Ca-thiolase. FIGS. 8A-C illustrate results for the wOUR 25 condition, with 1,3-BDO titer (g/L), 1,3-BDO productivity (g/L/hour), and 1,3-BDO yield per total sugar plotted over elapsed time (in hours), respectively. FIGS. 8D-F illustrate results for the wOUR 30 condition. In all six plots, the line with the lowest data point after 40 hours corresponds to Strain 2, while the other lines correspond to Strain 1. Strain 1 performed better on all three of these metrics under both aeration conditions.

Figure 9A:
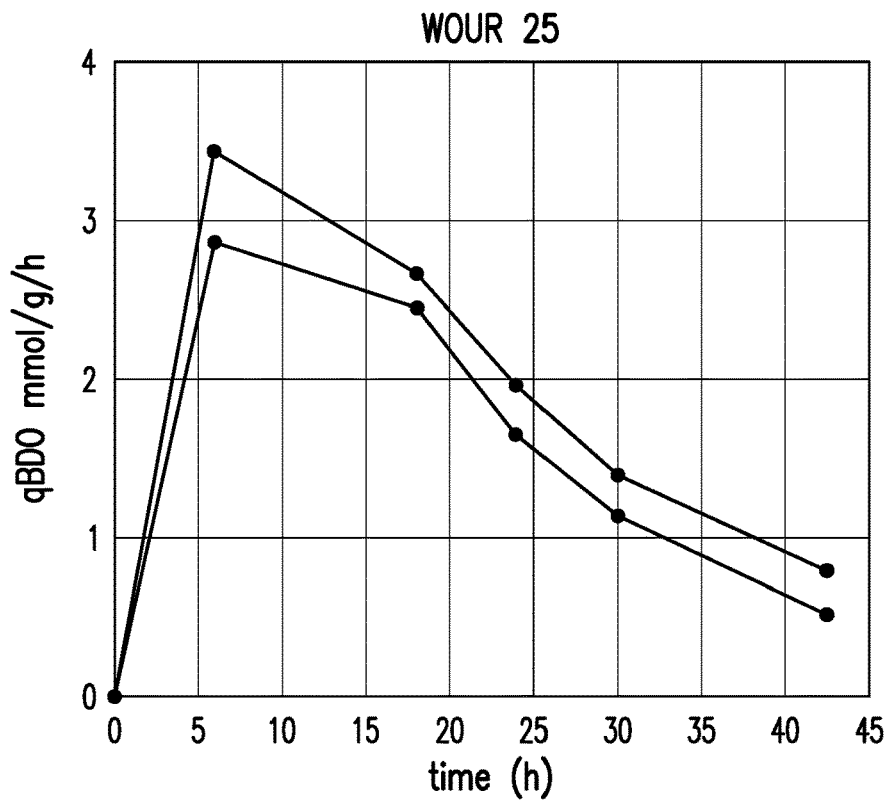
FIGS. 9A-B illustrate example 1,3-BDO production rates over time for wOUR 25 and wOUR 30, respectively.
Figure 9B:
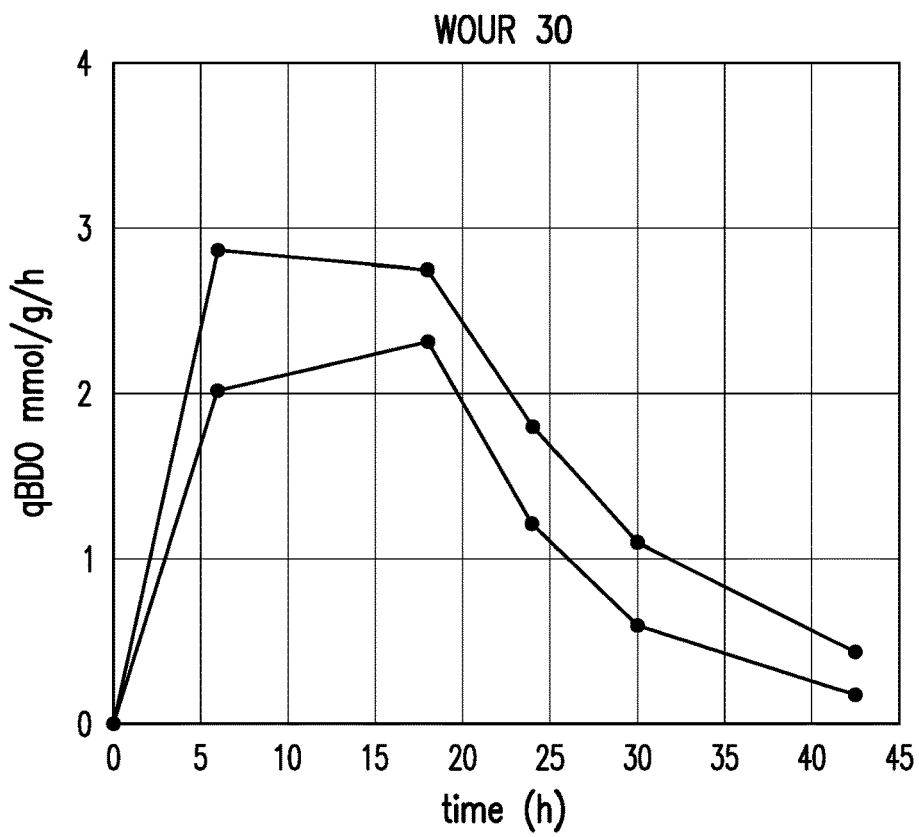

Rates of 1,3-BDO over time were also determined for both strains under both aearation conditions. Illustrative results for wOUR 25 and wOUR 30 are illustrated in FIG. 9A and FIG. 9B, respectively. In both graphs, the top curve corresponds to Strain 1, indicating an improved 1,3-BDO production rate at all time points for Re-thiolase relative to Ca-thiolase under both aeration conditions.

Figure 10A:
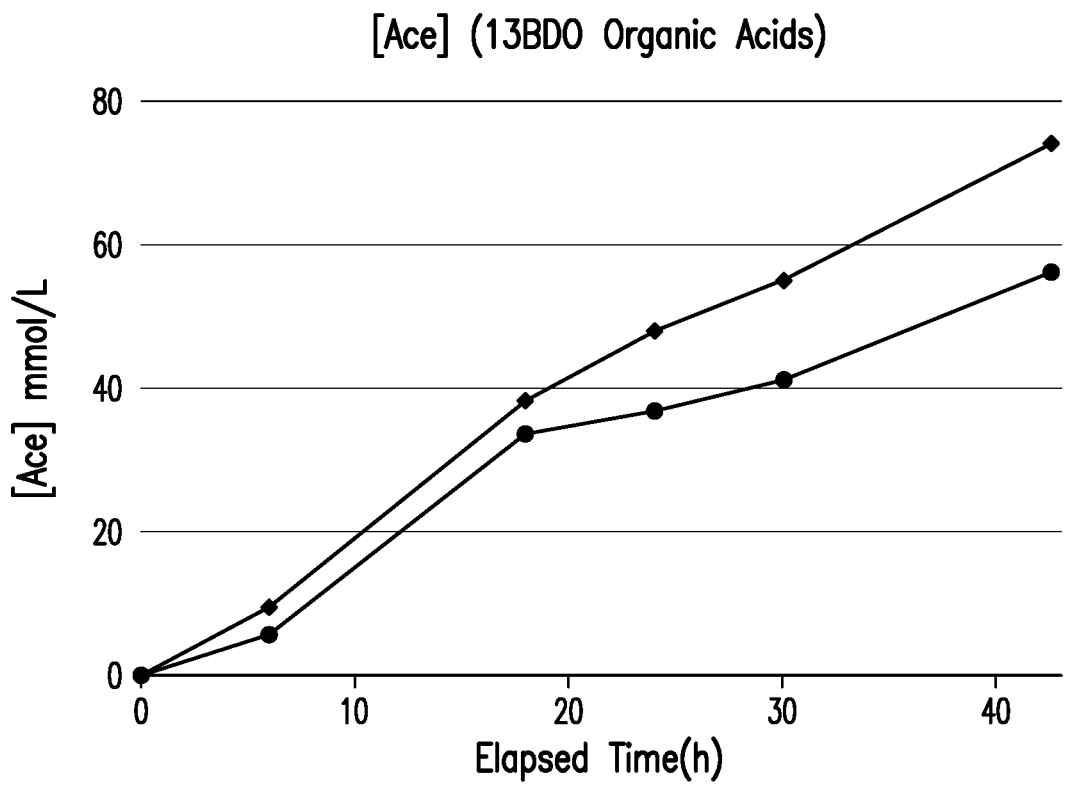
FIGS. 10A-H illustrate example concentrations of various byproducts at wOUR 25 (A and B) and wOUR 30 (C and D), and TCA cycle metabolites at wOUR 25 (E and F) and wOUR 30 (G and H).
Figure 10A:
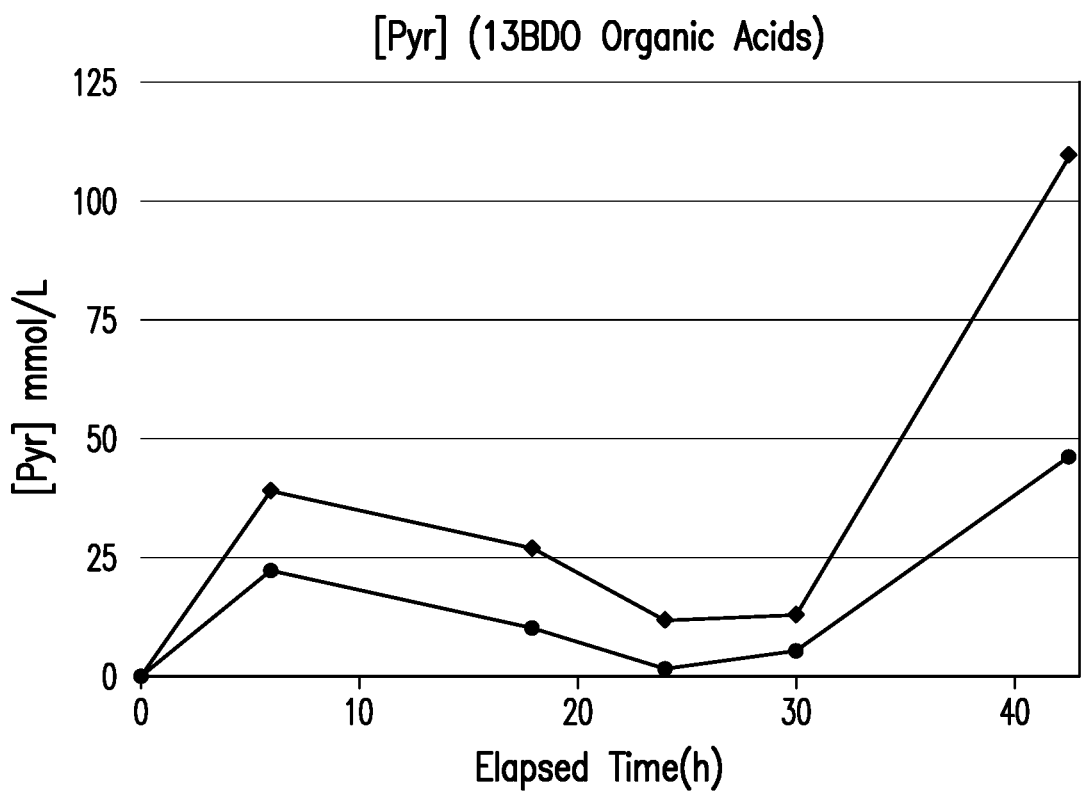
Figure 10B:
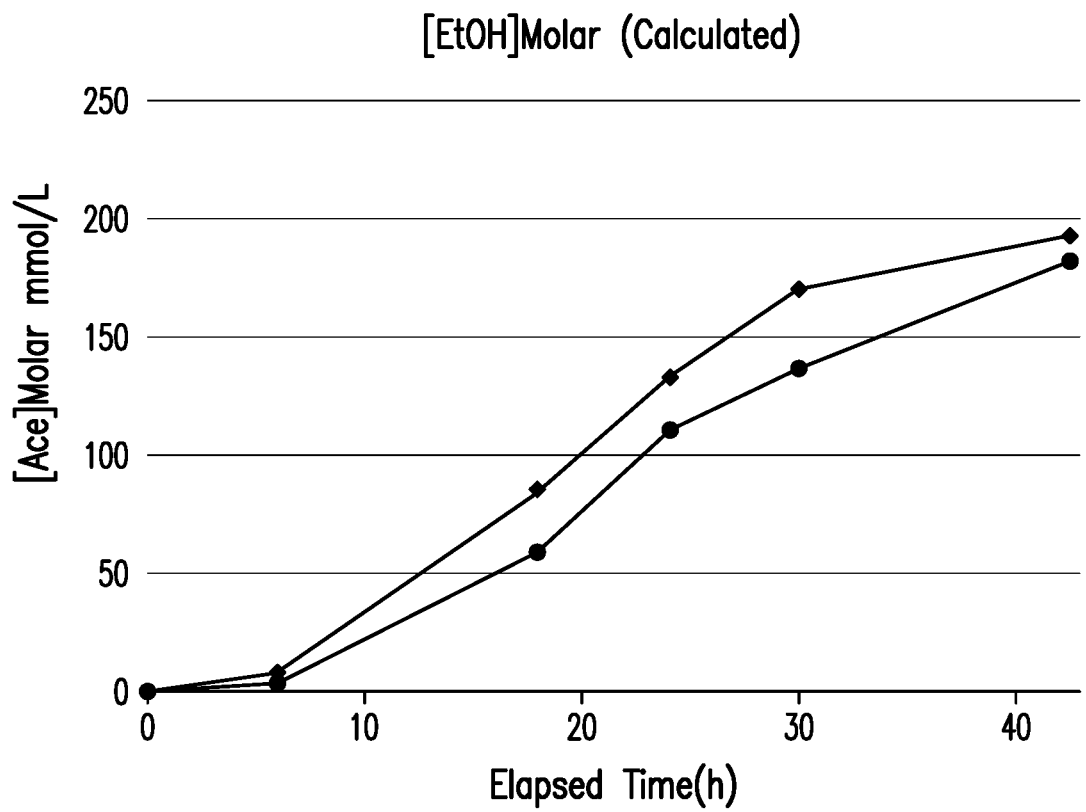
Figure 10B:
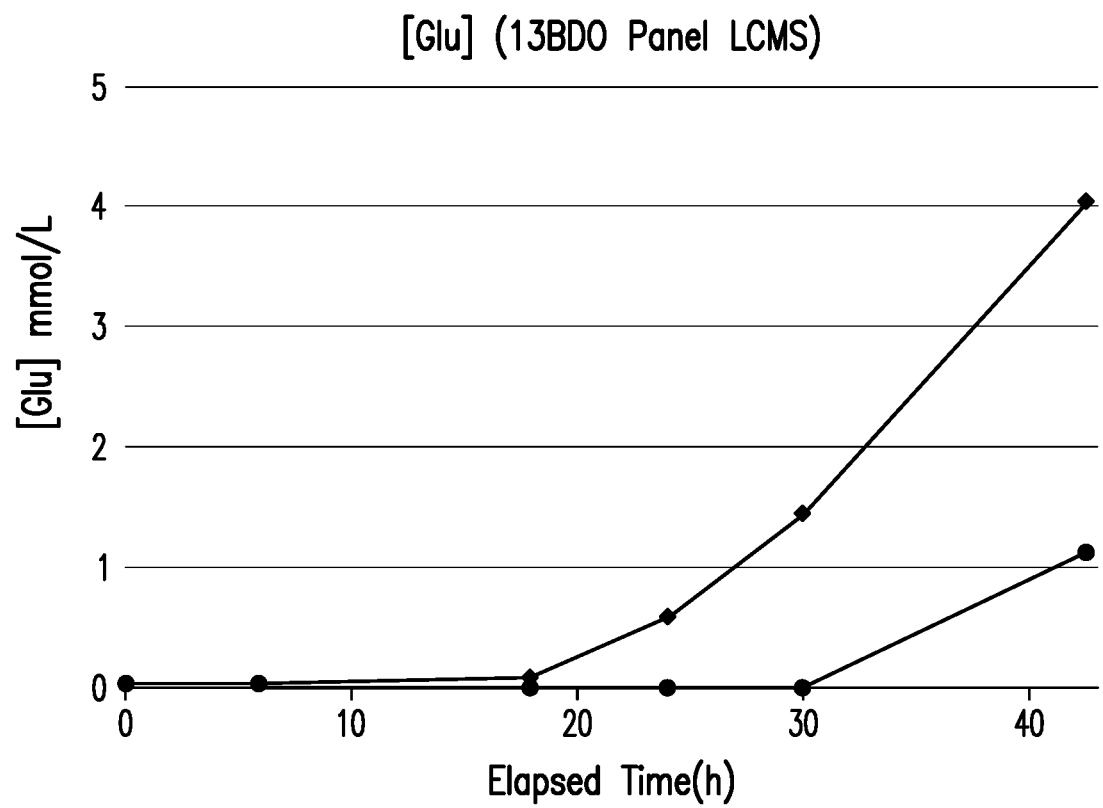
Figure 10C:
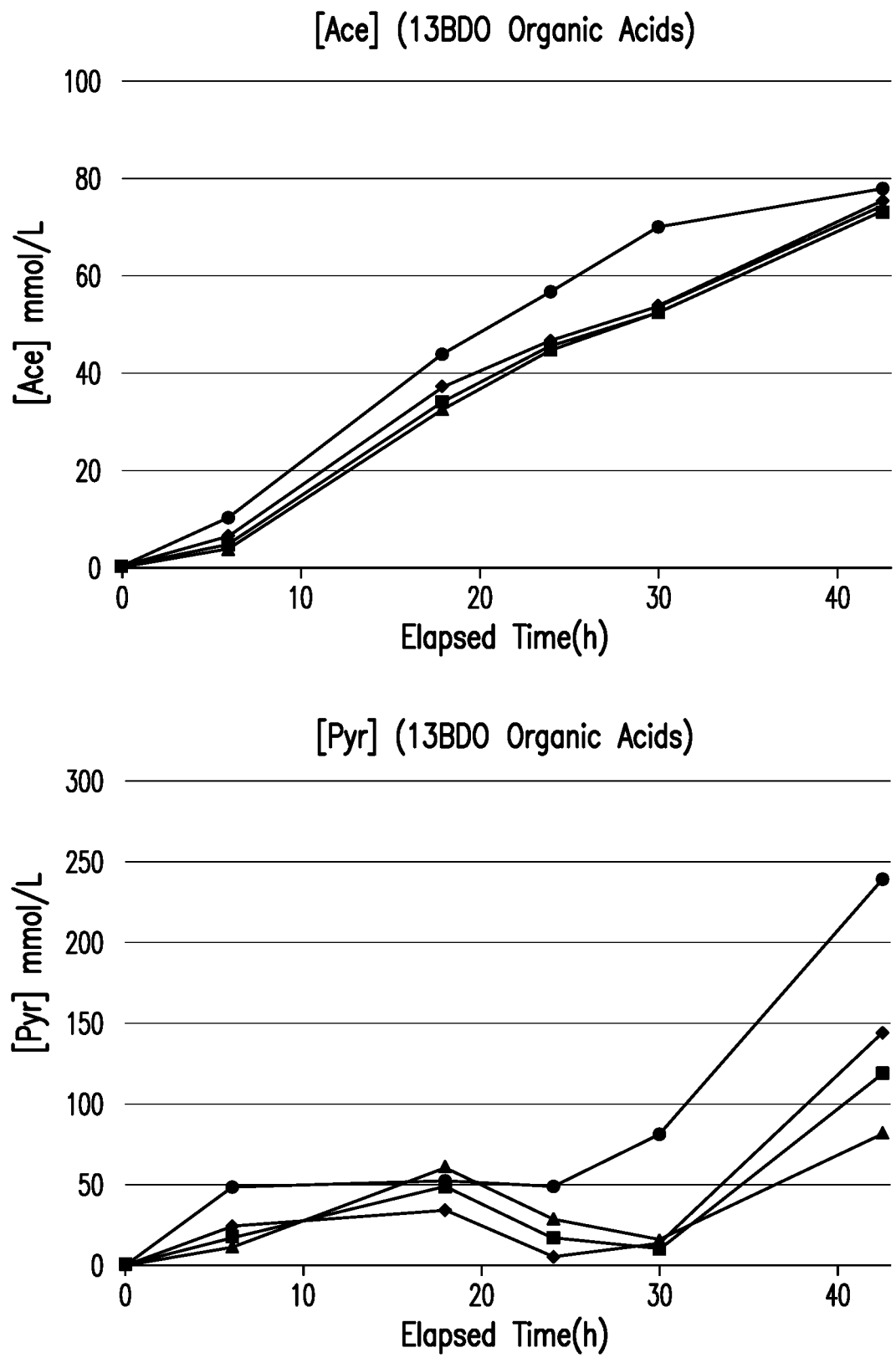
Figure 10D:
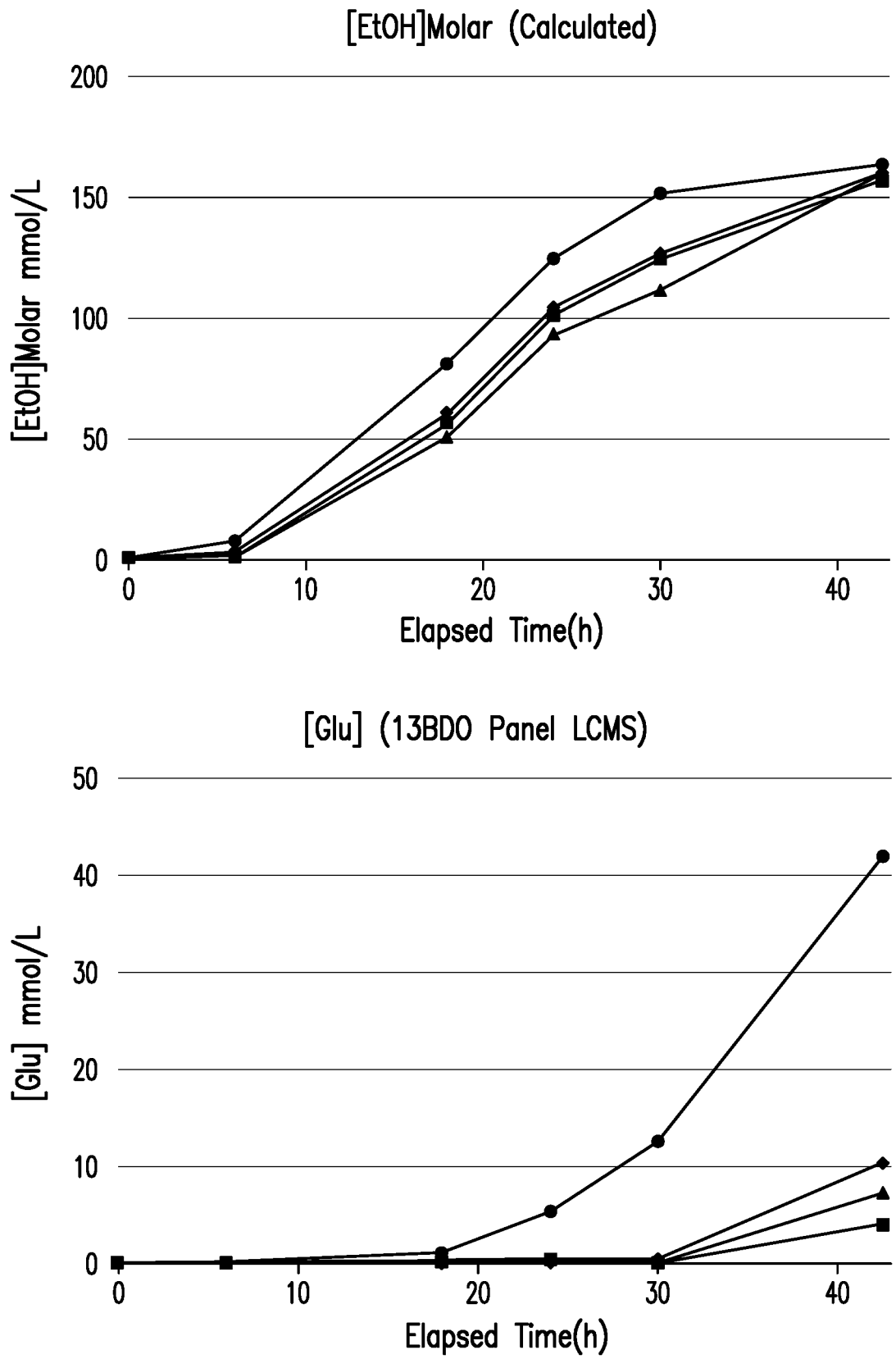
Figure 10E:
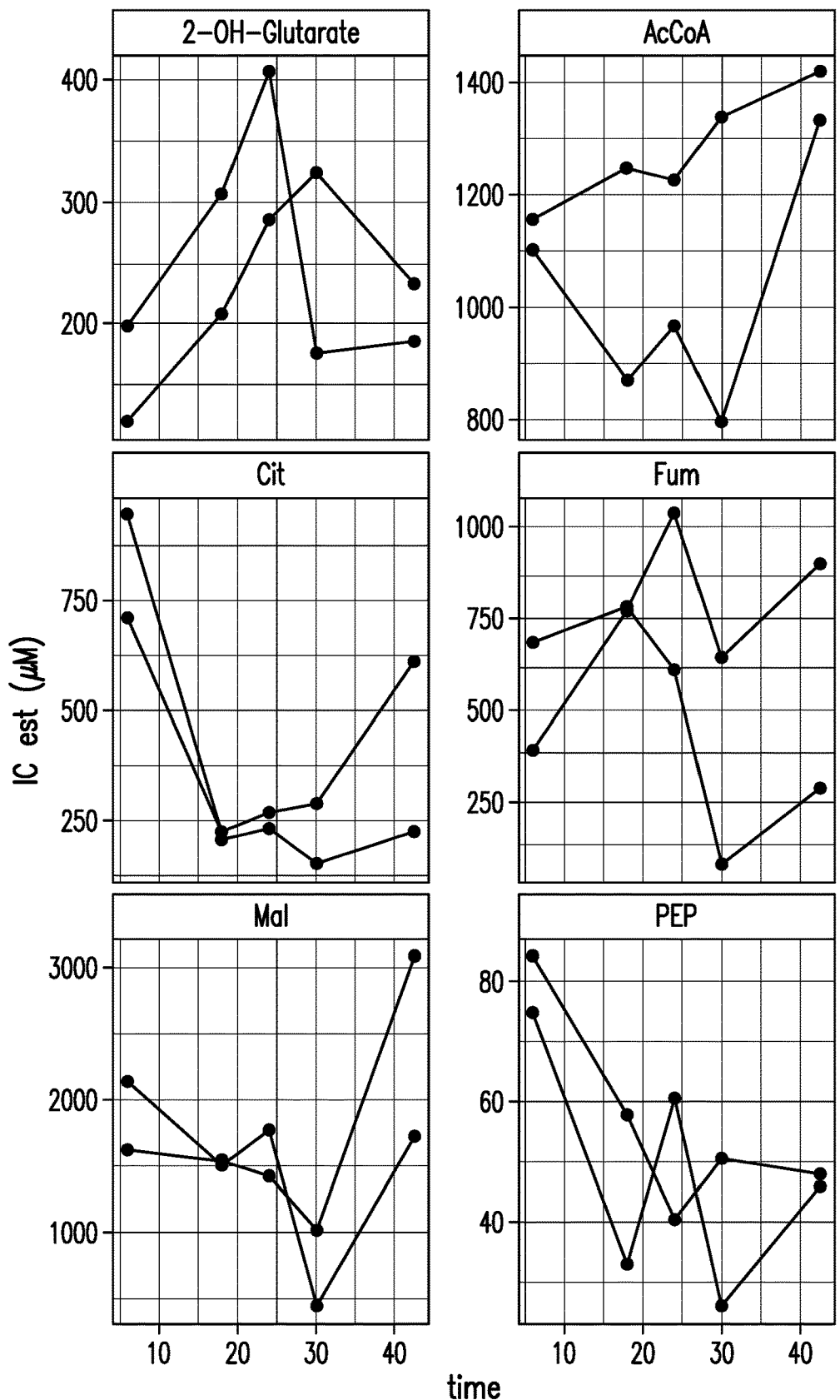
Figure 10F:
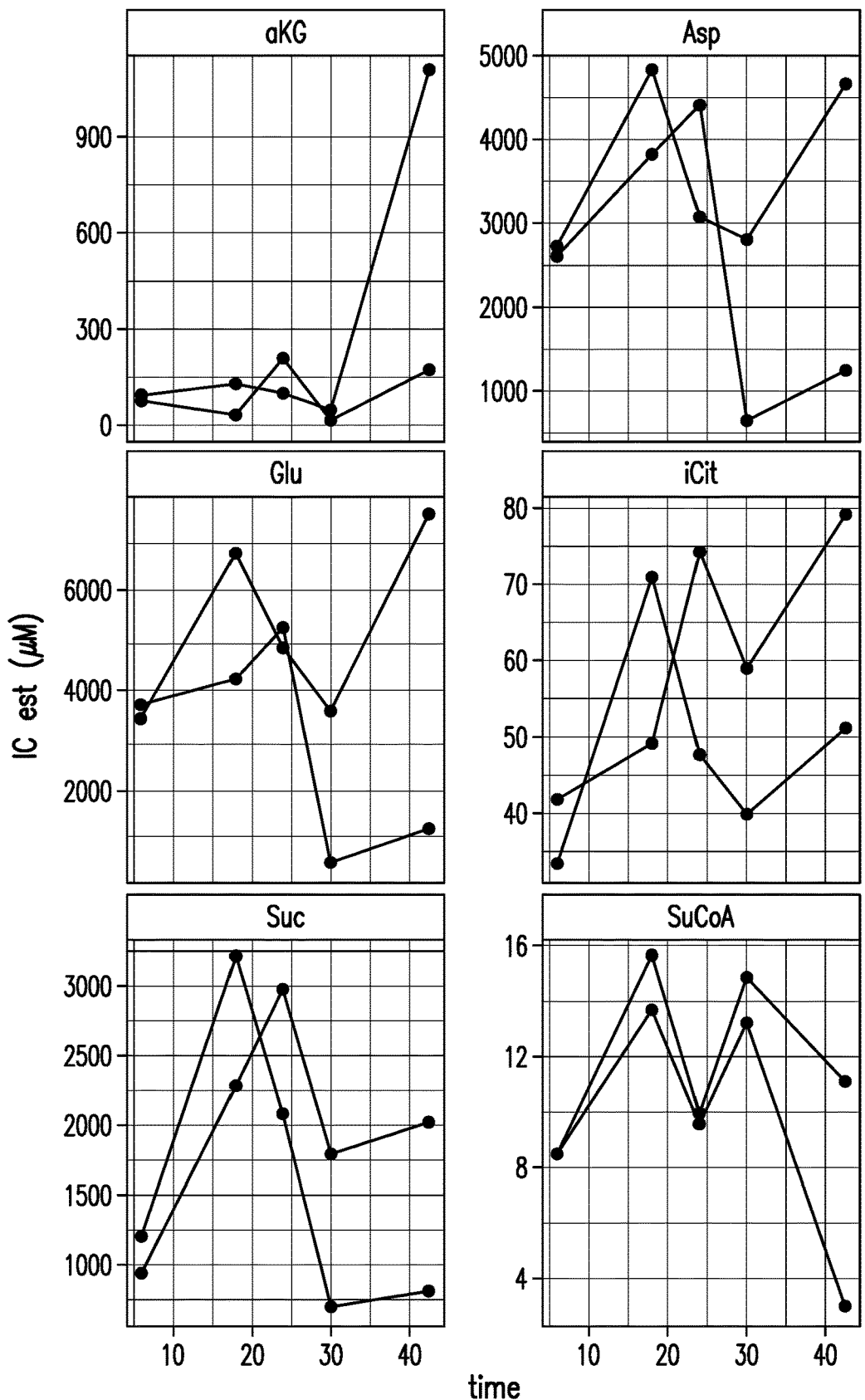
Figure 10G:
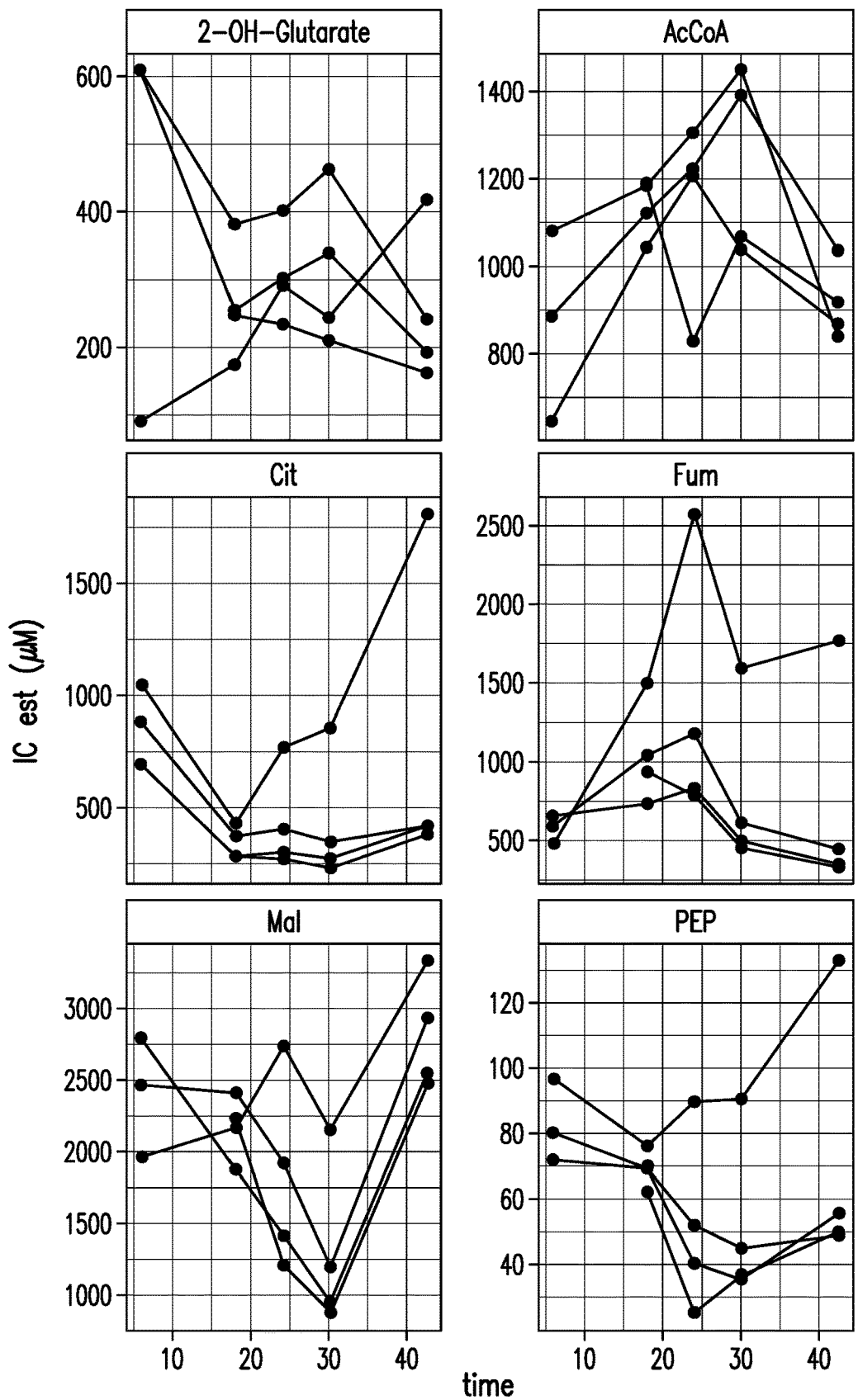
Figure 10H:
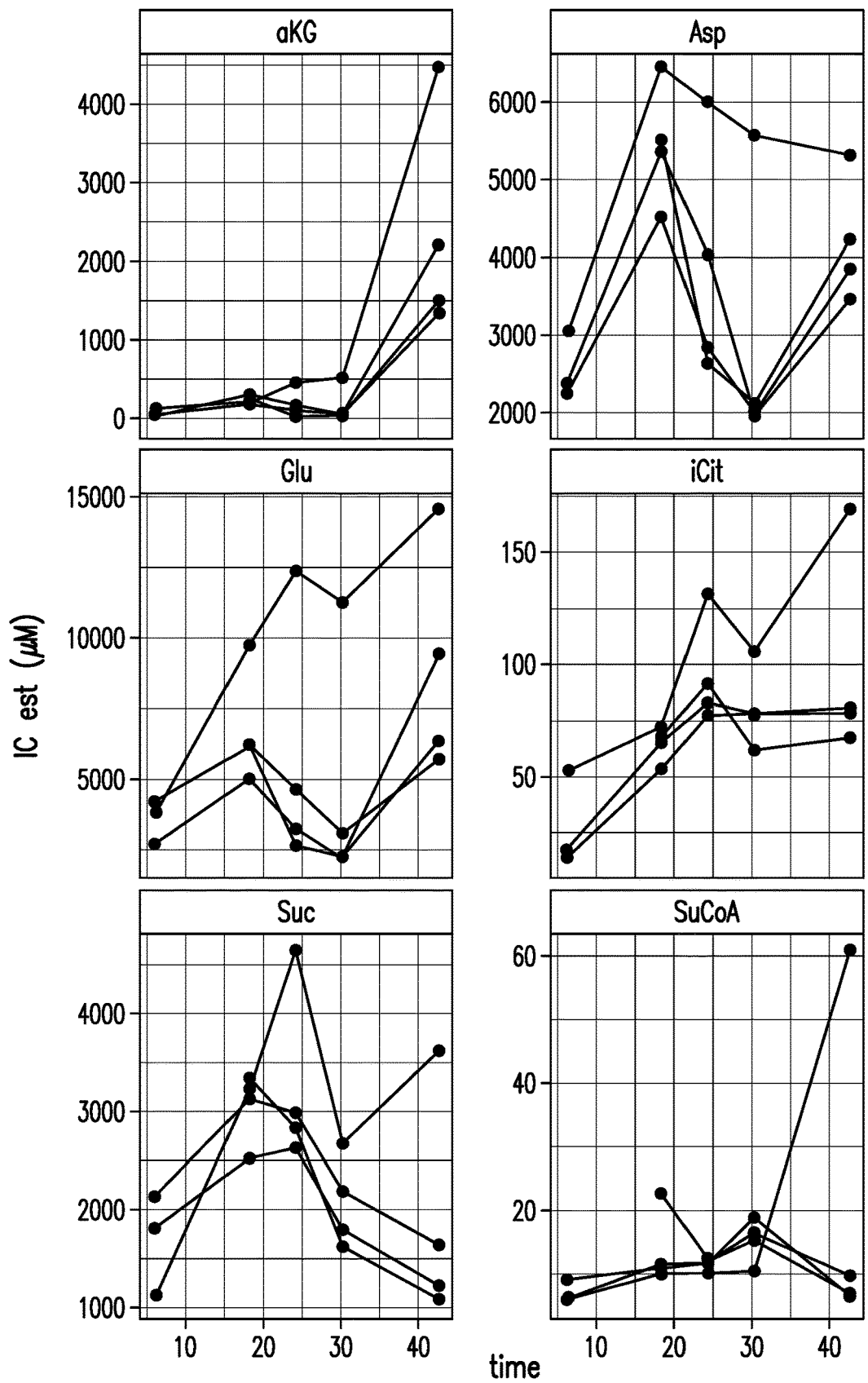
Figure 11:
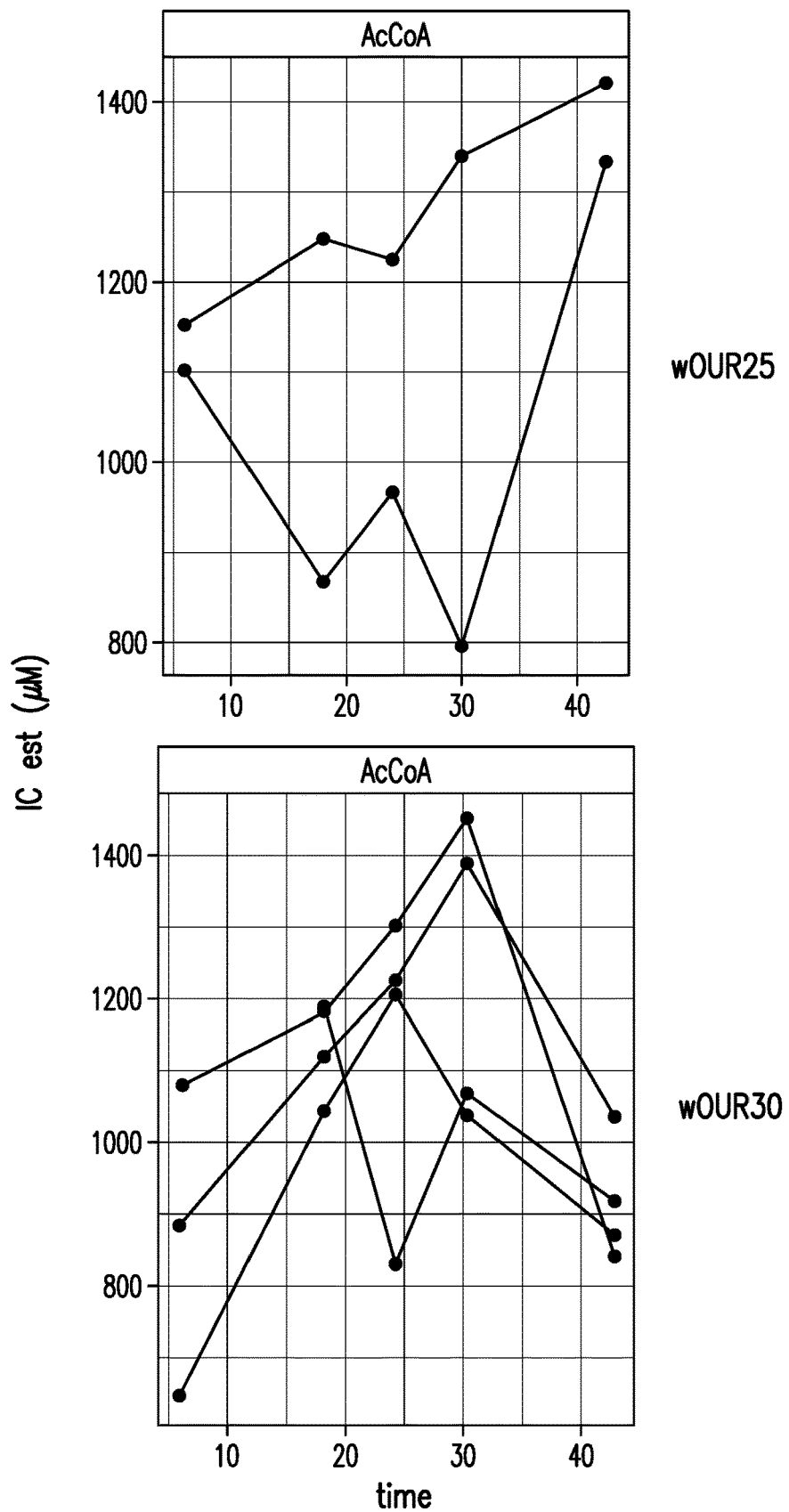
FIG. 11 illustrates example plots of acetyl-CoA for cultures at wOUR 25 and wOUR 30.

The concentration (in mmol/L) of the byproducts acetate ([Ace]), pyruvate ([Pyr]), ethanol ([EtOH]), and glutamate ([Glu]) were measured over time (in hours) for both Strain 1 and Strain 2 under both wOUR 25 and wOUR 30 aeration conditions. Illustrative results for the wOUR 25 condition are illustrated in FIGS. 10A-B, and illustrative results for the wOUR 30 condition are illustrated in FIGS. 10C-D. In all plots, the top line corresponds to Strain 2, while the other lines correspond to Strain 1. Results indicated that use of Re-thiolase reduced production of the byproducts under both conditions relative to Ca-thiolase. There were also significant reductions of TCA cycle metabolites (FIG. 10E-F for wOUR 25, and FIG. 10G-H for wOUR 30) and of acetyl-CoA (FIG. 11) with Strain 1 relative to Strain 2 under both conditions, indicating improved flux through the pathway. Measurements of redox metabolites indicated no significant difference between the strains.

Example 6: Thiolase and 3-hydroxybutyryl-CoA Dehydrogenase Variant Combination

Figure 12:
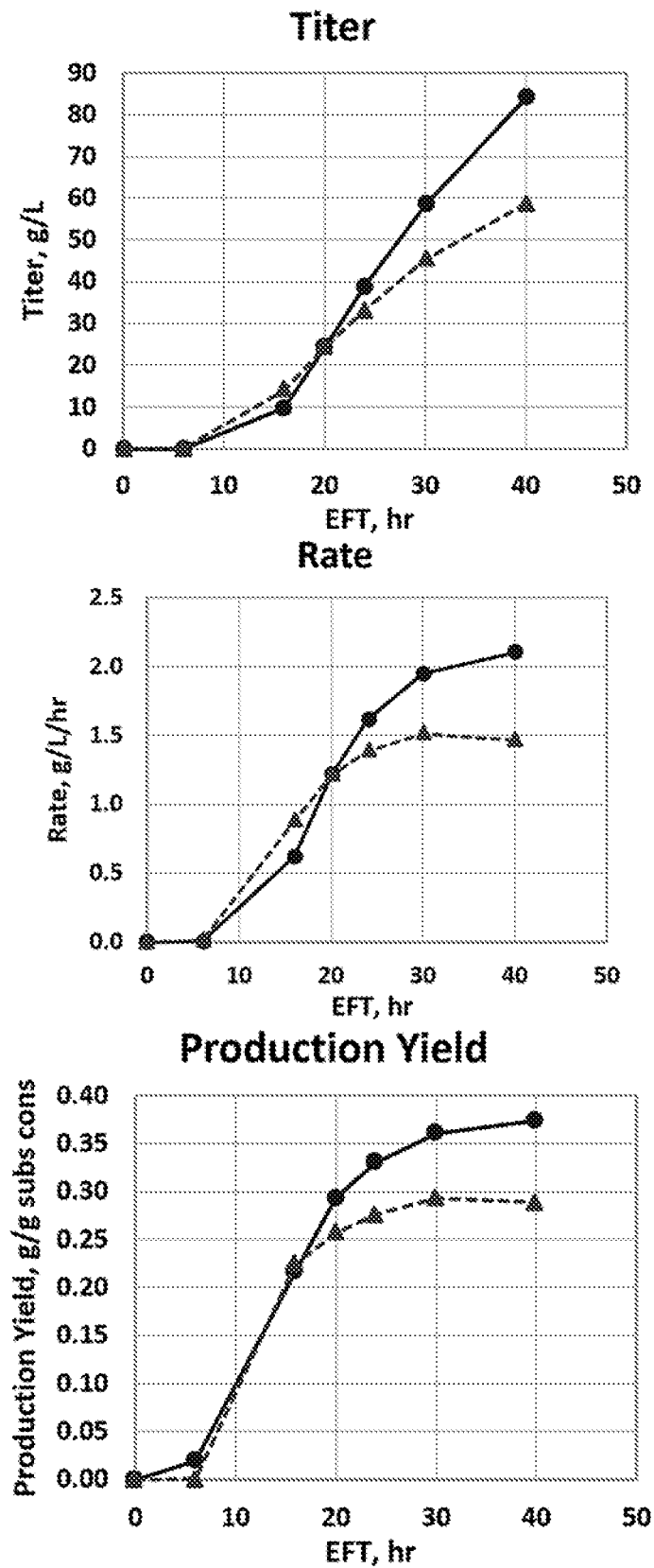
FIG. 12 illustrates examples of, from top to bottom, 1,3-BDO titer (g/L), 1,3-BDO production rate (g/L/hour), and 1,3-BDO yield per total sugar plotted over elapsed time (in hours).

The combined effect of Re-thiolase and an example 3-hydroxybutyryl-CoA dehydrogenase variant was evaluated using two strains. Strain 3 was engineered to express Re thiolase and wild-type 3-hydroxybutyryl-CoA dehydrogenase. Strain 4 was equivalent to Strain 3, except that the 3-hydroxybutyryl-CoA dehydrogenase was replaced with variant 1500AL. Each strain was grown in a tube culture, scaled up through three flask cultures, then cultured in a bioreactor at a pH of about 6.95, wOUR 30, and an initial $OD_{600}$ of 0.5. FIG. 12 illustrates, from top to bottom, 1,3-BDO titer (g/L), 1,3-BDO production rate (g/L/hour), and 1,3-BDO yield per total sugar (g/g) plotted over elapsed time (in hours). Each graph illustrates results for Strain 3 (dashed line, triangles), and Strain 4 (solid line, circles). Strain 4, combining Re-thiolase and the 1500AL variant exhibited the highest yield.

Figure 13:
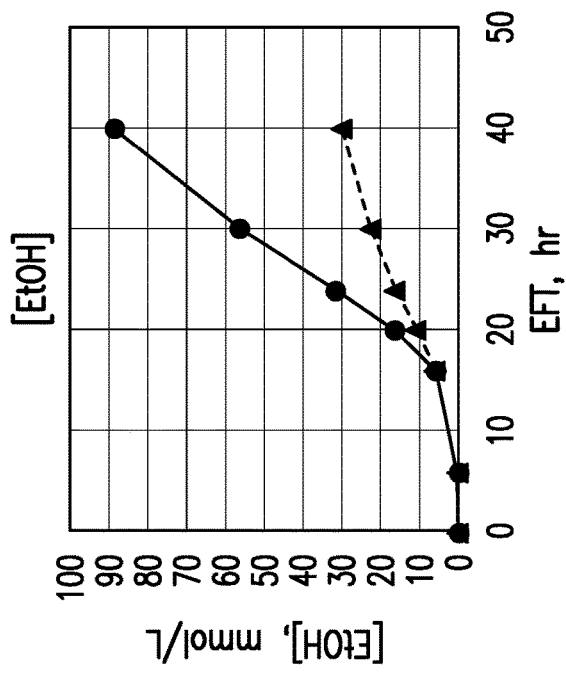
FIG. 13 illustrates example concentrations of the byproducts pyruvate ([Pyr]), ethanol ([EtOh]), 3-HB ([3HB]), and 4-hydroxy-2-butanone ([4OH2B]) over time.
Figure 13:
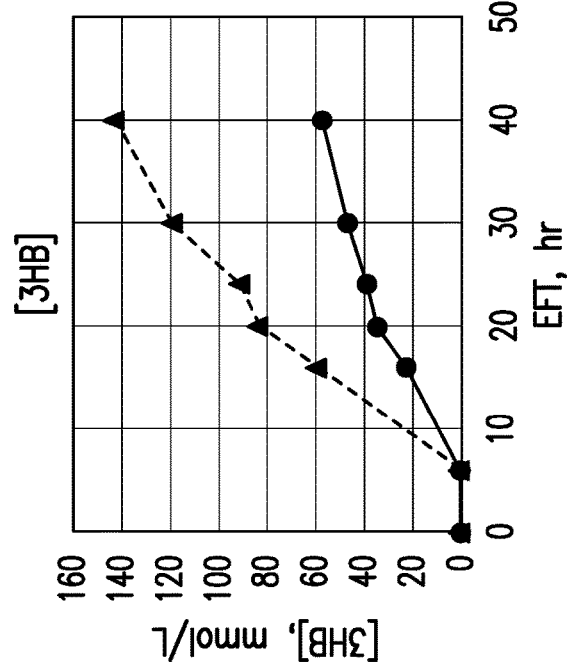
Figure 13:
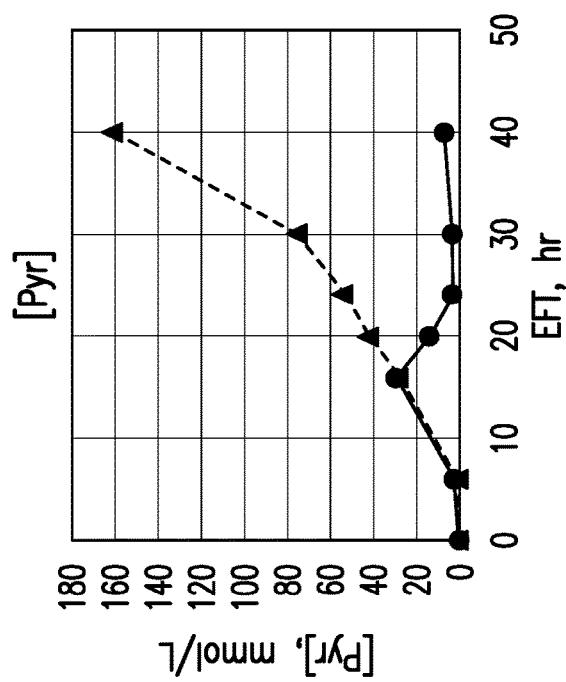
Figure 13:
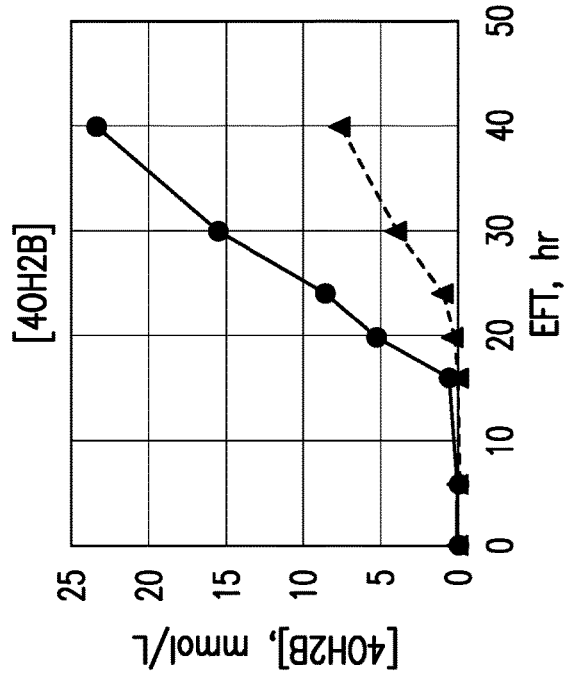

The concentrations of the byproducts pyruvate ([Pyr]), ethanol ([EtOh]), 3-HB ([3HB]), and 4-hydroxy-2-butanone ([4OH2B]) were also measured over time. Illustrative results for Strain 3 (dashed line, triangles), and Strain 4 (solid line, circles) are shown in FIG. 13.

Figure 14:
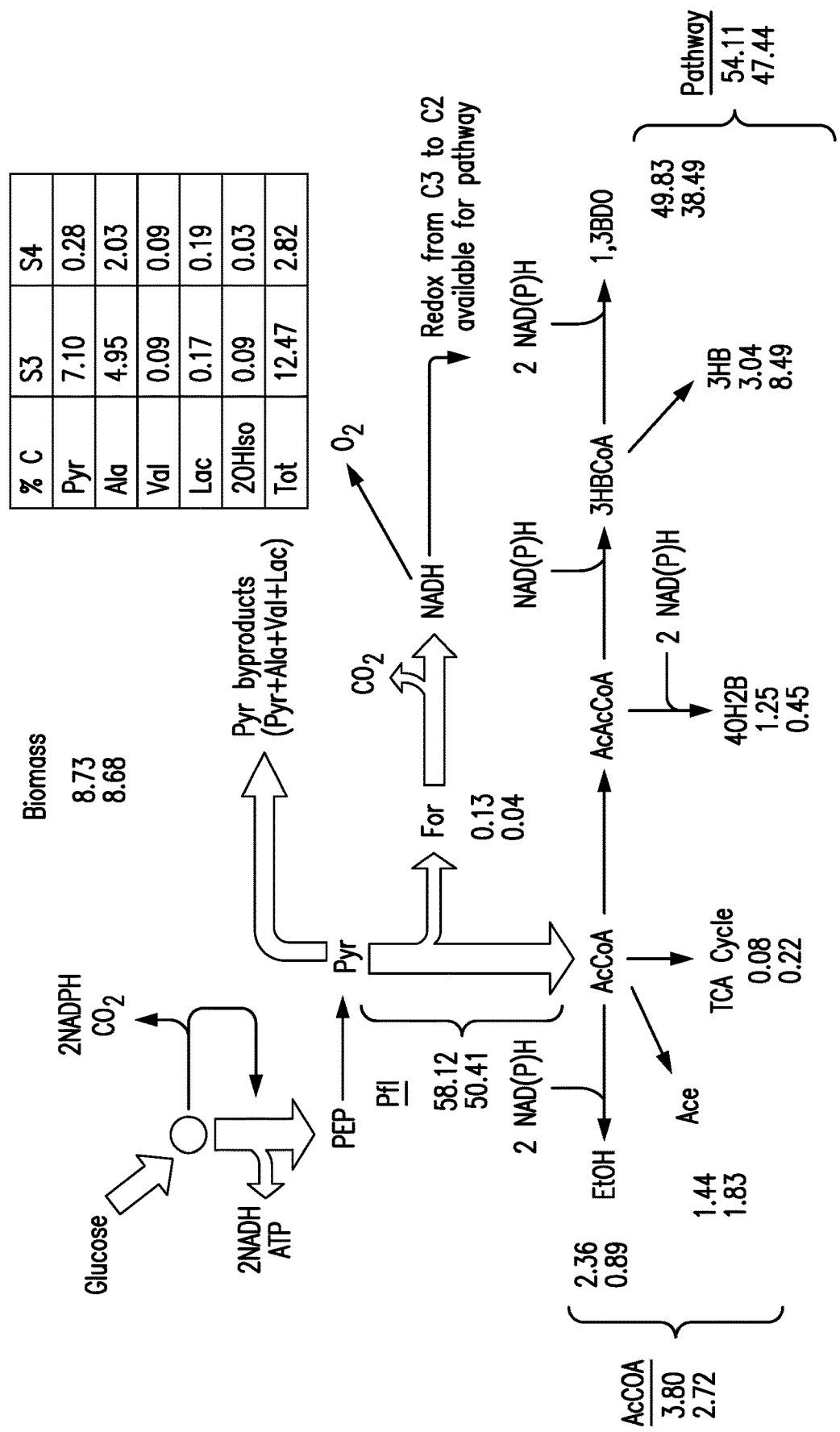
FIGS. 14 and 15A-B illustrate example percent carbon (% C) distributions among 1,3-BDO, various byproducts, and various intermediates after 40 hours of culture under the wOUR 30 aeration condition.
Figure 15A:
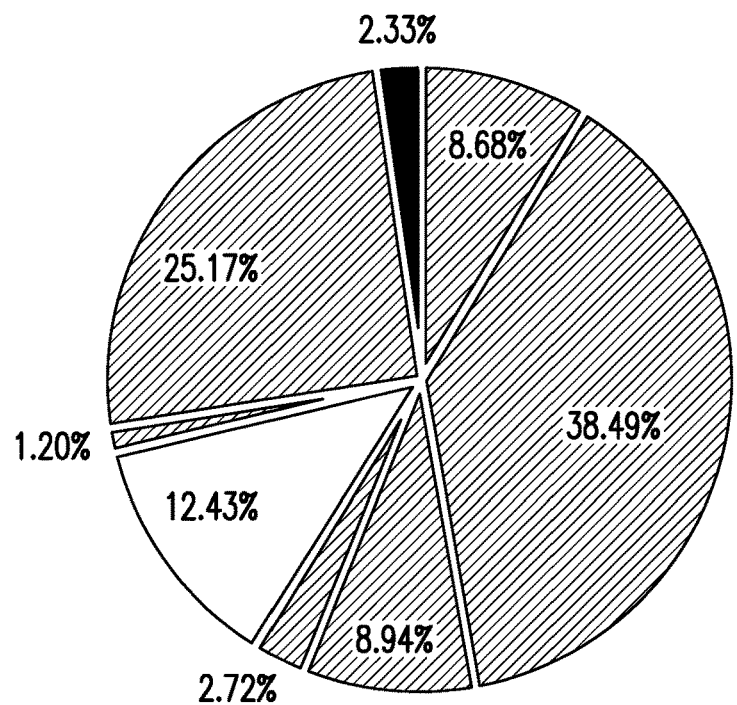
Figure 15A:
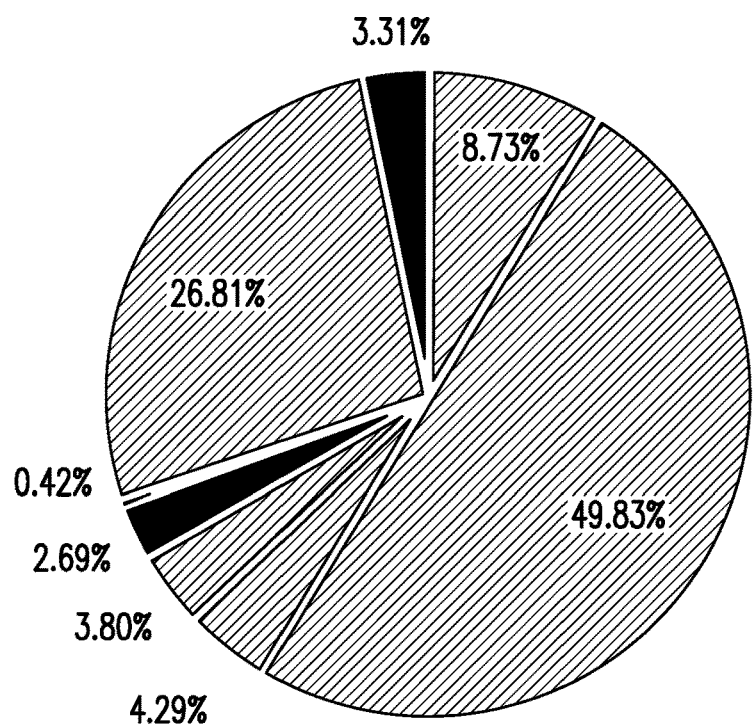
Figure 15B:
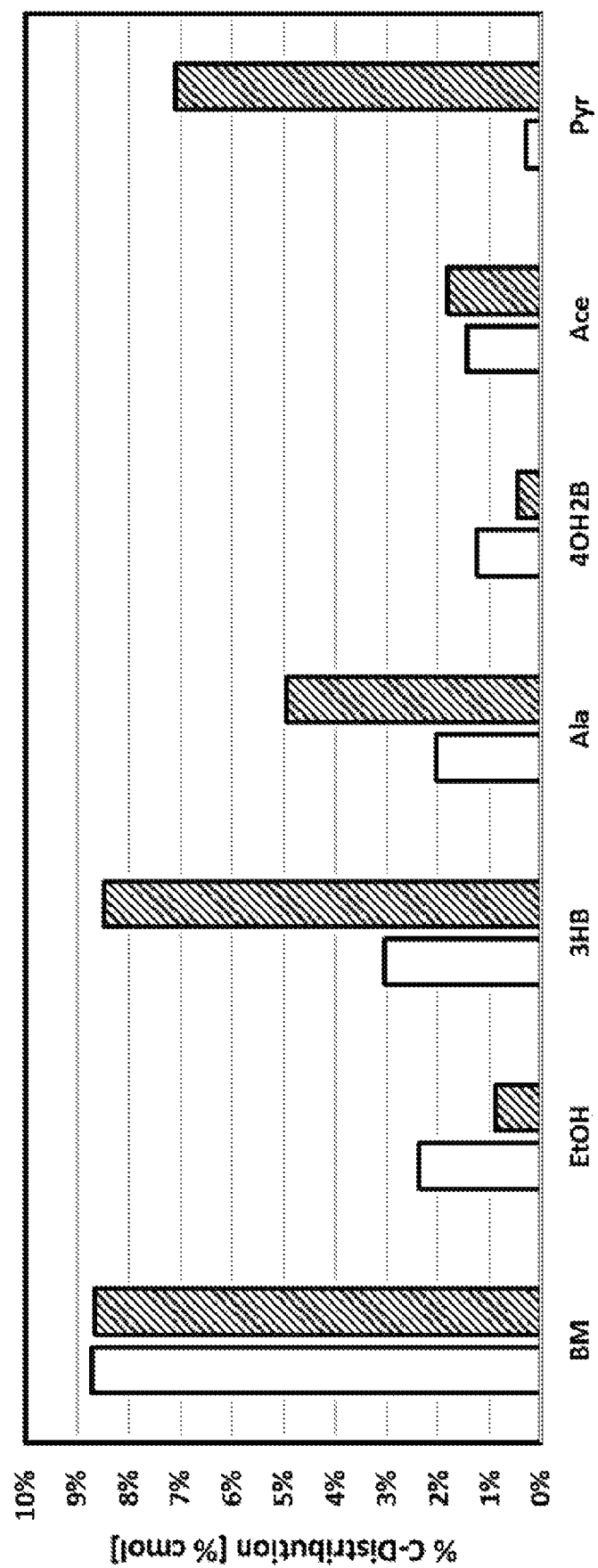

The percent carbon (% C) distribution among 1,3-BDO, various byproducts, and various intermediates after 40 hours of culture under the wOUR 30 aeration condition is summarized in FIG. 14. The table for pyruvate and related byproducts lists distributions for Strain 3 (S3) and Strain 4 (S4). Each pair of numbers lists, from top to bottom, values for Strain 4 and Strain 3. Totals under "AcCOA" combine values for ethanol (EtOH) and acetate (Ace). Totals under "Pathway" combine values for 4-hydroxy-2-butanone (4OH2B), 3-HB (3HB), and 1,3-BDO (1,3BDO). Totals under "Pfl" combine "Pathway" and "AcCOA" with values under TCA cycle and formate ("For"). FIG. 15A present carbon distribution data in the form of pie graphs. Beginning with the largest and moving clockwise, the sections of the pie graphs represent 1,3-BDO, other pathway products, AcCoA byproducts, pyruvate byproducts, TCA cycle byproducts, $CO_2$, unknown, and biomass. FIG. 15B illustrates selected portions of the carbon distribution results as a bar graph, with each pair of bars representing, from left to right, Strain 4, and Strain 3 ("BM" represents biomass).

Strain 4, with the combination of Re-thiolase and the 1500AL variant exhibited significantly reduced byproducts (e.g., alanine and pyruvate), as well as increased overall pathway flux and higher 1,3-BDO yield, relative to Strain 3.

Throughout this application various publications have been referenced. The disclosures of these publications in their entireties, including GenBank accession.version designations and/or GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. An isolated nucleic acid molecule encoding a variant 3-hydroxybutyryl-CoA dehydrogenase selected from:
   (a) a first nucleic acid molecule encoding a first variant of a reference 3-hydroxybutyryl-CoA dehydrogenase, wherein (i) the reference 3-hydroxybutyryl-CoA dehydrogenase has the amino acid sequence of SEQ ID NO: 2, (ii) the first variant comprises one or more amino acid substitutions, but less than 20 amino acid substitutions, relative to SEQ ID NO: 2, and (iii) the one or more amino acid substitutions relative to SEQ ID NO: 2 comprises a substitution at position G35 selected from G35A, G35C, G35D, G35E, G35H, G35K, G35L, G35M, G35P, G35S, G35T, G35V, and G35Y;
   (b) a second nucleic acid molecule encoding a second variant of the reference 3-hydroxybutyryl-CoA dehydrogenase, wherein the second variant (i) comprises one or more amino acid substitutions relative to SEQ ID NO: 2, wherein the one or more amino acid substitutions relative to SEQ ID NO: 2 comprises a substitution at position G35 selected from G35A, G35C, G35D, G35E, G35H, G35K, G35L, G35M, G35P, G35S, G35T, G35V, and G35Y, and (ii) has, other than the substitution at position G35, at least 85% sequence identity to SEQ ID NO: 2, while retaining the substitution at position G35;
   (c) a third nucleic acid molecule that hybridizes to the first or second nucleic acid molecule of part (a) or (b), respectively, under highly stringent hybridization conditions and comprises a nucleic acid sequence that encodes the one or more amino acid substitutions relative to SEQ ID NO: 2; and
   (d) a fourth nucleic acid molecule that is fully complementary to the first nucleic acid molecule of part (a), the second nucleic acid molecule of part (b), or the third nucleic acid molecule of part (c);
   wherein the first nucleic acid molecule, the second nucleic acid molecule, the third nucleic acid molecule, and the fourth nucleic acid molecule are not naturally occurring, and wherein the first variant and the second variant comprise 3-hydroxybutyryl-CoA dehydrogenase enzyme activity.

2. The isolated nucleic acid molecule of claim 1, wherein (a) the isolated nucleic acid molecule is the second nucleic acid molecule of part (b), and (b) the second variant has, other than the substitution at position G35, at least 90% sequence identity to SEQ ID NO: 2, while retaining the substitution at position G35.

3. A vector containing the nucleic acid molecule of claim 1.

4. A cell comprising the nucleic acid molecule of claim 1.

5. A culture medium comprising the cell of claim 4.

6. A method for constructing a host strain, the method comprising introducing the vector of claim 3 into a cell that is capable of fermentation.

7. The isolated nucleic acid molecule of claim 1, wherein the nucleic acid molecule is the first nucleic acid molecule of claim 1, part (a).

8. The isolated nucleic acid molecule of claim 1, wherein the nucleic acid molecule is the second nucleic acid molecule of claim 1, part (b).

9. The isolated nucleic acid molecule of claim 1, wherein the nucleic acid molecule is the third nucleic acid molecule of claim 1, part (c).

10. The isolated nucleic acid molecule of claim 1, wherein the nucleic acid molecule is the fourth nucleic acid molecule of claim 1, part (d).

11. The isolated nucleic acid molecule of claim 1, wherein the variant is a 3-hydroxybutyryl-CoA dehydrogenase having an increased ability to utilize NADH as a cofactor in a reaction converting acetoacetyl-CoA to 3-hydroxybutyryl-CoA, relative to a reference 3-hydroxybutyryl-CoA dehydrogenase consisting of amino acid sequence SEQ ID NO: 2.

12. The isolated nucleic acid molecule of claim 11, wherein the ability of the variant to use NADH as a cofactor is between 1.2-fold to 10-fold higher as compared to the reference 3-hydroxybutyryl-CoA dehydrogenase.

13. The isolated nucleic acid molecule of claim 1, wherein (a) the isolated nucleic acid molecule is the second nucleic acid molecule, and (b) the second variant has, other than the substitution at position G35, at least 95% sequence identity to SEQ ID NO: 2, while retaining the substitution at position G35.

14. The vector of claim 3, wherein the vector is an expression vector.

15. The cell of claim 4, wherein the nucleic acid molecule is integrated into a chromosome of the cell.

16. The cell of claim 4, wherein the cell is a microbial organism selected from a bacterium, a yeast, or a fungus.

17. The cell of claim 4, wherein the cell comprises a pathway that produces 3-hydroxybutyryl-CoA, 3-hydroxybutyraldehyde (3HBal), 3-hydroxybutyrate (3-HB), 1,3-butanediol (1,3-BDO), and/or an ester or amide thereof.

18. The cell of claim 17, wherein the cell comprises a polynucleotide encoding a thiolase with at least 85% amino acid sequence identity to SEQ ID NO: 4.

19. The cell of claim 18, wherein the cell produces one or more of the following:
(a) an increased amount of 1,3-BDO when cultured for at least 30 or 40 hours under conditions comprising a peak weight-based oxygen uptake rate of 50 mmol $O_2$/kg/hr, 40 mmol $O_2$/kg/hr, 30 mmol $O_2$/kg/hr, 25 mmol $O_2$/kg/hr, or lower, as compared to a cell in which the thiolase instead comprises the amino acid sequence of SEQ ID NO: 6;
(b) a decreased amount of pyruvate when cultured for at least 30 or 40 hours under conditions comprising a peak weight-based oxygen uptake rate of 50 mmol $O_2$/kg/hr, 40 mmol $O_2$/kg/hr, 30 mmol $O_2$/kg/hr, 25 mmol $O_2$/kg/hr, or lower, as compared to a cell in which the thiolase instead comprises the amino acid sequence of SEQ ID NO: 6; and/or
(c) 1,3-BDO and pyruvate at an increased ratio of 1,3-BDO to pyruvate when cultured for at least 30 or 40 hours under conditions comprising a peak weight-based oxygen uptake rate of 50 mmol $O_2$/kg/hr, 40 mmol $O_2$/kg/hr, 30 mmol $O_2$/kg/hr, 25 mmol $O_2$/kg/hr, or lower, as compared to a cell in which the thiolase instead comprises the amino acid sequence of SEQ ID NO: 6.

20. The cell of claim 19, wherein the increased amount of 1,3-BDO is an increase of at least 5%.

21. The cell of claim 19, wherein the decreased amount of pyruvate is a decrease of at least 5%.

22. The cell of claim 19, wherein the increased ratio is increased by at least 2-fold.

23. The cell of claim 19, wherein the 1,3-BDO is at least 75% R-1,3-butanediol (R-1,3-BDO).

24. The isolated nucleic acid molecule of claim 1, wherein the substitution at position G35 is G35A.

25. The isolated nucleic acid molecule of claim 1, wherein the substitution at position G35 is G35C.

26. The isolated nucleic acid molecule of claim 1, wherein the substitution at position G35 is G35D.

27. The isolated nucleic acid molecule of claim 1, wherein the substitution at position G35 is G35E.

28. The isolated nucleic acid molecule of claim 1, wherein the substitution at position G35 is G35H.

29. The isolated nucleic acid molecule of claim 1, wherein the substitution at position G35 is G35K.

30. The isolated nucleic acid molecule of claim 1, wherein the substitution at position G35 is G35L.

31. The isolated nucleic acid molecule of claim 1, wherein the substitution at position G35 is G35M.

32. The isolated nucleic acid molecule of claim 1, wherein the substitution at position G35 is G35P.

33. The isolated nucleic acid molecule of claim 1, wherein the substitution at position G35 is G35S.

34. The isolated nucleic acid molecule of claim 1, wherein the substitution at position G35 is G35T.

35. The isolated nucleic acid molecule of claim 1, wherein the substitution at position G35 is G35V.

36. The isolated nucleic acid molecule of claim 1, wherein the substitution at position G35 is G35Y.

37. The isolated nucleic acid molecule of claim 7, wherein the first variant comprises one or more amino acid substitutions, but less than 10 amino acid substitutions, relative to SEQ ID NO: 2.

38. The isolated nucleic acid molecule of claim 7, wherein the first variant comprises one or more amino acid substitutions, but less than 5 amino acid substitutions, relative to SEQ ID NO: 2.

39. The isolated nucleic acid molecule of claim 7, wherein the first variant comprises one or more amino acid substitutions, but less than 4 amino acid substitutions, relative to SEQ ID NO: 2.

40. The isolated nucleic acid molecule of claim 7, wherein the first variant comprises one or more amino acid substitutions, but less than 3 amino acid substitutions, relative to SEQ ID NO: 2.

41. A method for producing 3-hydroxybutyryl-CoA (3-HB-CoA), 3-hydroxybutyraldehyde (3-HBal), 3-hydroxybutyrate (3-HB), and/or 1,3-butanediol (1,3-BDO), the method comprising culturing the cell of claim 4, wherein the culturing is under conditions and for a sufficient period of time to produce 3-HB-CoA, 3-HBal, 3-HB, and/or 1,3-BDO.

42. The method of claim 41, wherein said cell is in a substantially anaerobic culture medium.

43. The method of claim 41, wherein the method further comprises isolating or purifying the 3-HB-CoA, 3-HBal, 3-HB, 1,3-BDO, and/or an ester or amide thereof.

44. The method of claim 43, wherein the isolating or purifying comprising distillation.

45. The method of claim 41, wherein the method produces 1,3-BDO.

46. A method for producing 3-hydroxybutyryl-CoA (3-HB-CoA), 3-hydroxybutyraldehyde (3-HBal), 3-hydroxybutyrate (3-HB), and/or 1,3-butanediol (1,3-BDO), the method comprising incubating a lysate of the cell of claim 4 to produce the 3-HB-CoA, 3-HBal, 3-HB, and/or 1,3-BDO.

47. The method of claim 45, wherein the 1,3-BDO is at least 75% R-1,3-butanediol (R-1,3-BDO).

48. The method of claim 45, wherein the 1,3-BDO is at least 80% R-1,3-butanediol (R-1,3-BDO).

49. The method of claim 45, wherein the 1,3-BDO is at least 90% R-1,3-butanediol (R-1,3-BDO).

50. The method of claim 45, wherein the 1,3-BDO is at least 95% R-1,3-butanediol (R-1,3-BDO).

51. The method of claim 45, wherein the 1,3-BDO is at least 98% R-1,3-butanediol (R-1,3-BDO).

52. The method of claim 46, wherein (a) the cell lysate is mixed with a second cell lysate, and (b) the second cell lysate comprises an enzymatic activity to produce a substrate of the variant, or a downstream product of 3-HB-CoA, 3-HBal, 3-HB, and/or 1,3-BDO.

53. The method of claim 46, wherein the method produces 1,3-BDO.

54. The method of claim 53, wherein the 1,3-BDO is at least 75% R-1,3-butanediol (R-1,3-BDO).

* * * * *